(12) United States Patent
Nakatuka et al.

(10) Patent No.: US 6,620,861 B1
(45) Date of Patent: Sep. 16, 2003

(54) DENTAL FILLERS

(75) Inventors: Toshiyuki Nakatuka, Kyoto (JP);
Yasuhisa Yasuda, Kyoto (JP); Katsuya Kimoto, Kyoto (JP); Mitsuharu Mizuno, Kyoto (JP); Noriyuki Negoro, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 56 days.

(21) Appl. No.: 09/714,876

(22) Filed: Nov. 17, 2000

(30) Foreign Application Priority Data

| Nov. 17, 1999 | (JP) | 11-327409 |
| Nov. 17, 1999 | (JP) | 11-327516 |
| Oct. 17, 2000 | (JP) | 2000-316440 |
| Sep. 26, 2000 | (JP) | 2000-292150 |
| Sep. 26, 2000 | (JP) | 2000-292167 |

(51) Int. Cl.⁷ .............................. C08K 9/06; A61K 6/08; A61K 6/093

(52) U.S. Cl. .................. 523/212; 523/115; 523/116; 523/118; 523/200; 523/201; 523/204; 523/205; 523/207; 523/209; 523/213; 523/214; 523/216; 523/217; 524/492; 524/493; 524/494; 524/588; 524/779; 524/789; 524/847; 524/858; 524/860

(58) Field of Search ................. 523/115, 116, 523/118, 200, 201, 204, 212, 213, 214, 216, 217, 205, 207, 209; 524/588, 492, 493, 494, 779, 789, 847, 858, 860

(56) References Cited

U.S. PATENT DOCUMENTS

| 3,971,754 A | | 7/1976 | Jurecic |
| 4,215,033 A | | 7/1980 | Bowen |
| 4,563,153 A | | 1/1986 | Schaefer |
| 4,629,746 A | | 12/1986 | Michl et al. |
| 4,714,734 A | * | 12/1987 | Hashimoto et al. ......... 152/525 |
| 4,758,612 A | | 7/1988 | Wilson et al. |
| 4,814,362 A | | 3/1989 | Billington et al. |
| 4,900,697 A | | 2/1990 | Akahane et al. |
| 4,920,082 A | | 4/1990 | Danielson |
| 5,055,497 A | | 10/1991 | Okada et al. |
| 5,304,586 A | | 4/1994 | Hammesfahr et al. |
| 5,356,951 A | | 10/1994 | Yearn et al. |
| 5,389,714 A | * | 2/1995 | Ohtomo et al. ............. 523/212 |
| 5,543,173 A | * | 8/1996 | Horn et al. .................. 264/109 |
| 5,641,347 A | | 6/1997 | Grabowski et al. |
| 5,679,710 A | | 10/1997 | Davy et al. |
| 5,733,644 A | | 3/1998 | Tanaka et al. |
| 5,780,668 A | | 7/1998 | Rheinberger et al. |
| 5,908,879 A | | 6/1999 | Kawashima et al. |
| 5,942,559 A | | 8/1999 | Voser et al. |
| 5,952,399 A | * | 9/1999 | Rentsch ....................... 423/306 |
| 5,973,030 A | * | 10/1999 | Matsushita et al. ......... 523/203 |
| 6,069,201 A | * | 5/2000 | Okinoshima et al. ....... 523/212 |
| 6,140,393 A | * | 10/2000 | Bomal et al. ............... 523/212 |
| 6,239,194 B1 | * | 5/2001 | Standke et al. ............. 427/212 |

FOREIGN PATENT DOCUMENTS

| EP | 1316129 | 5/1973 |
| EP | 0399148 | 11/1990 |
| JP | 5024328 | 8/1975 |
| JP | 54107187 | 8/1979 |
| JP | 57500150 | 1/1982 |
| JP | 5782303 | 5/1982 |
| JP | 5821887 | 5/1983 |
| JP | 59101409 | 6/1984 |
| JP | 59110606 | 6/1984 |
| JP | 61127717 | 6/1986 |
| JP | 61148109 | 7/1986 |
| JP | 61152715 | 7/1986 |
| JP | 61215234 | 9/1986 |
| JP | 61241303 | 10/1986 |
| JP | 62113749 | 5/1987 |
| JP | 63088110 | 4/1988 |
| JP | 63182238 | 7/1988 |
| JP | 63201038 | 8/1988 |
| JP | 1186807 | 7/1989 |
| JP | 2008203 | 1/1990 |

(List continued on next page.)

OTHER PUBLICATIONS

JP 07213876 A, Aug. 1995, Japan, Nago et al. English Abstract.*
Properties of 4–META/MMA–TBB Opaque Resin with PMMA–coated Titanium Dioxide, Shikazairyo—Kikai vol. 7, No. 1, p. 27–32 (1988).

*Primary Examiner*—Robert Dawson
*Assistant Examiner*—Jeffrey B. Robertson
(74) *Attorney, Agent, or Firm*—Stevens, Davis, Miller & Mosher, L.L.P.

(57) ABSTRACT

There are provided an inorganic filler, multi-functional filler, an organic compound filler, a modified filler, and a dental coloring filler suitable in use as a filler in a dental composition, compositions having a resin matrix of an organic polymer material, as well as a process for producing the same. Disclosed are an inorganic filler which comprises an inorganic fine particle, wherein the surface of the inorganic fine particle is covered with polysiloxane. Also disclosed is a multi-functional filler which comprises an inorganic fine particle containing an acid reactive element, wherein a cement reactive phase is formed on the surface of the inorganic fine particle, and the cement reactive phase is further covered with polysiloxane. Also disclosed is an organic compound filler which comprises an organic-inorganic polymer particle or an organic polymer particle, wherein the surface of the organic-inorganic polymer particle or an organic polymer particle is covered with an inorganic film. Also disclosed is a modified filler which comprises an inorganic fine particle, wherein the surface of the inorganic fine particle is covered with polyorganosiloxane. Also disclosed is a dental col ring filler, which comprises an inorganic particle and a coloring particle, wherein the inorganic particle and the coloring particle are unifoy mixed and dispersed, the surfaces of these particles are covered with poly(organo)siloxane. Further disclosed are dental compositions containing above fillers, and processes for producing above fillers.

50 Claims, 2 Drawing Sheets

FOREIGN PATENT DOCUMENTS

| | | |
|---|---|---|
| JP | 2206628 | 8/1990 |
| JP | 2225302 | 9/1990 |
| JP | 2248315 | 10/1990 |
| JP | 3007770 | 1/1991 |
| JP | 317803 | 3/1991 |
| JP | 3065506 | 3/1991 |
| JP | 3070778 | 3/1991 |
| JP | 3109307 | 5/1991 |
| JP | 5194135 | 8/1993 |
| JP | 733476 | 2/1995 |
| JP | 7196428 | 8/1995 |
| JP | 7196429 | 8/1995 |
| JP | 7196430 | 8/1995 |
| JP | 7196431 | 8/1995 |
| JP | 7331112 | 12/1995 |
| JP | 8143747 | 6/1996 |
| JP | 8157742 | 6/1996 |
| JP | 8208417 | 8/1996 |
| JP | 8225423 | 9/1996 |
| JP | 9169613 | 6/1997 |
| JP | 9194674 | 7/1997 |
| JP | 9255516 | 9/1997 |
| JP | 1036116 | 2/1998 |
| JP | 1094552 | 4/1998 |
| JP | 2807641 | 7/1998 |
| JP | 11100305 | 4/1999 |
| JP | 2925155 | 5/1999 |
| JP | 11209213 | 8/1999 |
| JP | 2000 500484 | 1/2000 |
| JP | 2000 500486 | 1/2000 |
| JP | 2000 143430 | 5/2000 |
| WO | 8102254 | 8/1981 |
| WO | 9718791 | 5/1997 |
| WO | 9718792 | 5/1997 |

\* cited by examiner (a)

(b)

DENTAL FILLERS

FIELD OF THE INVENTION

The present invention relates to an inorganic filler, particularly relates to a composition containing an organic polymer material as a matrix, particularly to an inorganic filler which is suitable for using as a filler in a dental composition, and a process for producing the same.

In addition, the present invention relates a multi-functional filler, particularly relates to a composition containing an organic polymer material as a matrix, particularly to an inorganic filler which is suitable for using as a filler in a dental composition, and a process for producing the same.

In addition, the present invention relates to a composition having a resin matrix of an organic polymer material, in particular, an organic compound filler which is suitable for using as a filler in a dental composition, as well as a process for producing the same.

Furthermore, the present invention relates to a composition having a resin matrix of an organic polymer material, in particular, a modified filler which is suitable for using as a filler in a dental composition, as well as a process for producing the same.

Furthermore, the present invention relates to a dental coloring filler which can be used in the dental field such as a crown and bridge material, a filling material, a prosthetic material and an adhesive material, light-shielding material (an opaque material), and a process for producing the same, as well as a dental composition containing the same.

BACKGROUND OF THE INVENTION

A composite restorative material which is widely used in the dental field in recent years is required to have the following properties. As such there are certain mechanical properties such as the mechanical strength which can stand a high gliding occlusal pressure upon mastication, the durability under severe conditions, the thermal expansion coefficient having the similar magnitude to that of a teeth substance and the low polymerization shrinkage for preventing stripping from a teeth substance upon curing and the like, the optical properties such as the color tone and the transparency adapted to a natural teeth and the surface smoothness and glossiness observed after polishing and the like. In addition to the bio-compatibility such as the non-toxicity, the insolubility and the low water absorbing property and the like. Moreover, particularly recently, the properties such as the sustained fluoride releasability for reinforcing a teeth substance to prevent dental caries and the radiopacity for confirming the recurrence situation of secondary caries after the treatment and for being capable of distinguishing from an enamel of a teeth substance have been required.

Composite restorative materials composed of a polymerizable monomer, a polymerization initiator, and a filler such as an inorganic material, an organic material and an organic-inorganic compound material and the like have hitherto been used for all restoration, such as filling and repairing, of a dentinal defective-part, prosthesis, artificial fang and other uses. Among these components, many have hitherto been reported on a filler. This is because the properties of a filler are thought to have the influence on the properties of a composite restorative material since the filler accounts for a large proportion of the composite restorative material.

Fillers which have used in a composite restorative material at the early stage are mainly a ground-type filler prepared by grinding a large mass such as a α-quartz and a variety of glasses having an average particle size of a few microns to a few hundreds microns. When these fillers are used, they can impart various properties such as the suitable viscosity and the handling, the mechanical strength, the low polymerization shrinkage, the thermal expansion coefficient similar to that of a teeth substance to a composite restorative material.

However, such fillers have unacceptable polishability because of a large average particle size and, in particular, they have the shortcomings such as the inferior surface smoothness and the surface glossiness after polishing. In order to overcome this problem, an attempt has been tried to make an average particle size as small as possible but has not been sufficient yet.

In order to overcome this shortcoming, there has been proposed a composite restorative material using, as a filler, a ultrafme particle having an average particle size of 0.01~0.1 $\mu$m synthesized by a pyrolytic process or a a vapor phase process, for example, spray-pyrolized silica and fumed silica, and these have been used widely as a general abbreviation of MFR. This composite restorative material has the better polishability and is excellent in the surface smoothness and the surface glossiness. However, when the ultrafine particle is dispersed in a polymerizable monomer, the viscosity of the resulting paste is highly increased due to a large specific surface area and, for this reason, an amount of a filler content must be considerably suppressed. For this reason, the mechanical property of a composite restorative material, particularly, the bending strength becomes inferior. In addition, they have also a problem that the polymerization shrinkage upon the curing of a paste is relatively large and, additionally, the thermal expansion coefficient of a cured material becomes very large.

As the other filler, there are silica and silica composite oxide which are synthesized by a solution reaction such as a sol-gel process starting with an organometal compound, are narrow in the particle size distribution, are spherical and have an average particle size of 0.1 $\mu$m to a few microns. These fillers are disclosed in JP-A 59-101409 and the like. Since these fillers cause aggregation at a drying step, the surface treatment of a filler can not be performed uniformly and there is a problem on the mechanical strength and the durability such as deterioration of a material due to water absorption.

In addition, in the light of impartation of the favorable nature of each filler, there are provided hybrid-type composite materials in which an ultrafine particle of silica and a relatively large inorganic filler are combined.

For example, they are disclosed in JP-A 57-82303, J-A 57-50150, JP-A 61-148108 and the like. However, although these hybrid types improve the mechanical properties sufficiently, there is a problem that the operability is bad due to a viscous paste and they lack the smoothness after finish polishing as compared with MFR.

Then, for the purpose of satisfying the various properties necessary for a composite restorative material, many attempts have been hitherto reported to perform high density packing by fine-grinding and aggregating techniques and surface treating techniques. For example, a process of obtaining an aggregate from a solution of a metal compound and a silica sol is described in JP-A 7-196428 and a process of aggregating a metal oxide having an average particle size of not smaller than 0.05 $\mu$m and not greater than 1 $\mu$m is described in JP-A 7-196431. Although these improve the polishability, a surface treating agent such as a silane coupling agent does not act on aggregated parts, which causes a decrease in the durability due to water absorption.

According to the results of the present inventor's study, in order to obtain a sufficient polishability and mechanical properties such as the durability and the mechanical strength, it was found that the selection of a raw material of an inorganic filler, the fine-grinding and the surface treatment are a very important factor, but a variety of problems resulted. As a process of fine-grinding which has been previously performed, there is a dry-grinding process by a mechanical process with an ocsillating mill, a ball mill, a jet mill and the like. According to this process, it is difficult to obtain a particle having an average particle size of 3 $\mu$m or less and, since the particle size distribution is large, a complicated step such as separation becomes necessary. In addition, although in wet-grinding using the facility therefor, grinding can be performed to an extent of an average particle size of 1 $\mu$m or less, the aggregation of particles occurs at a drying step. Even when this aggregate was tried to be disintegrated using a suitable disintegrating equipment, it was impossible to disintegrate to primary particles. As another fine-grinding process, there is preparation of fine particles from the solution state using the sol-gel process techniques. However, since a drying step is also necessary for this process, aggregates are produced. It was also found that, since these aggregates do not undergo the uniform surface treatment, when they are used as a filler in a composite restorative material, the durability is problematic. In addition, silica has mainly been used previously as a raw material for an inorganic filler. However, it has problems on the polishability and wear of opposing teeth due to its hardness. For that reason, a variety of raw materials have begun to be used from a viewpoint of the necessity of imparting many properties to an inorganic filler. To the contrary, it was found that the effect of a silane coupling agent, which is generally used, becomes poor and it has the influence on the mechanical strength. In addition, it is contemplated that although the polishability and surface smoothness and glossiness can be improved by fine-grinding, the high density packing into a composite restorative material becomes difficult due to increased specific surface area and the influence on the mechanical strength.

From the foregoing, in order to satisfy the properties required for a composite restorative material, it is an important theme to maintain the particle size control and the uniform monodispersion without any agregation, and it is necessary that the surface is treated uniformly with a surface treating agent.

In general, in the dental field, a silane coupling agent is known as the known surface treating agent. However, this treating agent does not necessarily act effectively on all inorganic fillers. It is effective for an inorganicfiller to have many OH groups on the surface such as silica, but when an amount of OH groups is decreased, its effect is decreased. JP-B 5-67656 describes a polymerizable aromatic carboxylic acid compound for treating the surface of alumina, Japanese Patent No. 2695479 describes a dicarboxylic acid compound as an agent for treating the surface of an inorganic filler, and Japanese Patent No. 2925155 describes an organic phosphorus compound as an agent for treating the surface of an inorganic filler. Like this, since an amount of OH groups on the surface is different depending upon an inorganic filler used, it was necessary to use a variety of surface treating agents depending upon a kind of an inorganic filler to be treated. For this reason, the wettability with a resin is different depending upon a surface treating agent, used for treating the surface of a particle, it may have the adverse influence on the various properties, such as a change in not only the properties of the resulting composite restorative material but also the nature and the handling of a paste before the curing. In addition, JP-B 6-99136 describes two kinds of silane coupling agents, long chain or short chain, and Japanese Patent No. 2690364 describes the surface treatment using a silane coupling agent having a large hydrophobic group, and objects of which are both to improve the surface treatment effect. However, there has not been obtained an inorganic filler which has the sufficient polishability and durability and satisfies other various properties, and which has no aggregate, is monodispersed and has the uniformly treated surface.

Recently, some fillers are proposed, which focus on their optical properties such as the polishability and surface smoothness and glossiness and the like, for example, including a filler which is generally called as an organic-inorganic compound filler or a compound filler. These are made by pre-mixing an inorganic particle with a polymerizable monomer to polymerize once to give a polymer, which is then ground to obtain a compound filler. Although JP-A 54-107187 discloses a compound filler using a ultrafine particle as an inorganic particle, it has a defect that, for example, since the ultrafine particle has a large specific surface area, its proportion in the compound filler is small so that the surface hardness of a composite restorative material containing this compound filler is low and its thermal expansion coefficient becomes high. In addition, composite restorative materials containing: as an inorganic particle, a compound inorganic oxide composed of silica and another element which can bind with the silica which has an average particle size of 0.1~1.0 $\mu$m and is spherical in JP-A 3-12043; as an inorganic particle, a compound oxide composed of silica dioxide and an element of Group II~IV in the Periodic Table having an average particle size of 0.01–0.1 $\mu$m in JP-A 8-143747; and as an inorganic particle, a glass powder having an average particle size of 0.1~5.0 $\mu$m in JP-A 5-194135 are disclosed, respectively. Although they can solve the problems in the surface hardness and the thermal expansion coefficient by increasing a proportion of the content of inorganic components in the filler, there is almost no improvement in the mechanical properties. Further, a compound filler having the surface on which double bonds are left by using a trifunctional or difunctional polymerizable monomer in JP-B 6-62687; and a compound filler containing an aggregate obtained by aggregating an inorganic particle having an average particle size not greater than 1.0 $\mu$m, and heat-treating in JP-A 7-196430, are disclosed, respectively. However, they are aiming at improving their mechanical properties, but the effect is insufficient. Then, for the purpose of improving the mechanical properties, composite restorative materials using a compound filler and another inorganic filler therein are disclosed. JP-B 7-91170 discloses a glass filler, an a ultrafine silica particle and a compound filler, and JP-A 9-194674 discloses a composite restorative material containing a compound filler and an aggregated inorganic oxide particle. However, since these had a shortcoming resulted from the use of inorganic fillers, they were not necessarily satisfactory in all properties required for composite restorative materials.

As mentioned above, the compound filler has the excellent optical properties after polishing, such as the surface smoothness and glossiness and the like, but the effect of the surface treatment on the compound filler is insufficient, and the wettability with a resin component becomes poorer and, therefore, it has a big problem in the mechanical properties or handling. Almost all the components on the surface of the compound filler are organic components and a little amount of inorganic components are present there. In addition, although inorganic components are exposed there, the surfaces of the inorganic particles are already treated by using a silane coupling agent and the like, when the compound filler is produced. Therefore, it is considered that the effect of the surface treatment on the compound filler is not exhibited sufficiently, and the mechanical properties can not be achieved. Further, when the surface treatment is not done uniformly and effectively, the handling of a paste thereof, which is a state before curing, and the durability of the composite restorative material containing the compound filler after curing, and the like are affected. Almost all of the previous surface treatments on a compound filler were within the physical adsorption of a surface treating agent. In the handling of the paste, the wettability between the surface of a filler and a resin matrix is an important factor and, in the case of the physical adsorption, since the surface treating agent is removed from the filler surface with time, the wettability changes, that is, the handling tends to become worse. Additionally, in the cured material thereof, minute gaps are generated in the interface between the filler surface and the resin matrix, and the permeation of water into the gaps makes a problem in the durability and the like. There is no organic compound filler having the excellent polishability, particularly the surface smoothness and glossiness after polishing, which are the conventional features of a compound filler as the above fillers have, and in which the surface treating agent can act effectively to impart the excellent mechanical properties, the durability, and the stable handling.

In the dental field, the effect of fluoride to prevent dental caries is well known. As fluoride-releasing dental materials which have been previously used, there are cement materials known as a glass ionomer cement or a glass polyalkenoate cement. However, since these materials are have poor durability, there are problems on the quality of the materials themselves, such as a change in the color tone and the breakage in a shorter period as short as one year, regardless of their advantage in the ability of the sustained fluoride release. In addition, although the incorporation of a metal fluoride compound such as sodium fluoride to dental materials (JP-A 2-258602) has been attempted, such an attempt had shortcomings that a large amount of fluoride is dissolved out in a shorter period and are not sustained fluoride release, and the mechanical strength of the materials themselves is decreased. Although the incorporation of a polymer comprising an acid fluoride component of acrylic acid or methacrylic acid into a composite restorative material was reported (JP-A 57-8.8106, JP-A 62-12706 and Japanese Patent No. 2678108), there were shortcomings that although fluoride is released at a small quantity over a longer period of time, it can not be applied to sites where a high load is applied, and the effect of fluoride ions can not be expected because it has a low fluoride content due to a little proportion of a resin component in the composite restorative material. JP-A 11-209213 and JP-A 10-36116 report a metal fluoride compound covered with polysiloxane. This is aimed at controlling the release of fluoride by controlling the solubility of metal fluoride, but the metal fluoride can not be incorporated into materials for which the mechanical strength is required, such as composite restorative materials.

In addition, JP-A 7-206470 and JP-A 11-268929 report the release of fluoride from glass materials without the acid treatment, however, this means that the glass itself dissolves in water, resulting in a problem regarding the long term durability. WO94/23687 describes a fluoride sustained release pre-formed glass ionomer filler which is formed from a powder-form reaction product of a polyalkenoic acid and a fluoride-containing glass. This is characterized by the sustained fluoride release without accompanied by no dissolution disintegration. However, since the glass surface of this filler reacts with the polyalkenoic acid, the effect of the surface treatment is not sufficient and there are problems in the mechanical properties and the durability. Moreover, there is no description with respect to the light-diffusion of the transmitted light or the polishability. In addition, recently, a "compomer" is focused on as an in-between material of a glass ionomer cement and a composite resin. This is a one-paste type composition comprising a glass used for a glass ionomer cement and an acidic group-containing monomer, and exhibits the high fluoride releasability, but its mechanical strength is decreased by contact with water for a longer period of time. Thus, dental restorative materials are desired which have the fluoride releasability, and have the stability in water for a longer period of time as well as the mechanical properties to stand a high occlusion pressure.

Amalgams have been previously used for a filling restoration after the treatment of dental caries and gold alloys have been used for crown restoration. In recent years, composite materials have become rapidly prevalent because it is not expensive and is relatively easy to achieve the color tone and the transparency close to those of natural teeth by using them. Now, composite restorative materials are used not only for restoration and prosthesis of odontic defects, but also for applications in an adhesive material, a sealant, an artificial fang and the like. Recently, among various properties of the composite restorative materials, the aesthetic properties such as the polishability, the surface smoothness and glossiness after polishing, the transparency, and the color tone are required at a high level by clinician's needs. Many reports are proposed on the great contribution of the components of the composite restorative materials to a variety of properties of the material for expressing the aestheticism of the composite restorative materials.

For example, JP-A 11-100305 proposes that the same color tone and texture as those of natural teeth can be obtained by controlling a particle size and a refractive index of a colloidal silica and a refractive index of a polymerizable monomer. In addition, JP-B 745373 proposed that a change in color tones between before and after polymerization can be rendered smaller by inclusion, in a composite material, of both a filler having a refractive index lower than an average value of refractive indexes of a matrix before and after polymerization, and a filler having a refractive index higher than the average value. Further, JP-A 9-255516 proposes that a composite material containing an aggregate of an inorganic filler having the difference in a refractive index from a resin matrix after polymerization of 0.06 or less and having an average particle size of 0.01~1.0 μm, and an inorganic filler having the difference in a refractive index from a resin matrix after polymerization of more than 0.06 and having an average particle size of 1.0 μm or more is excellent in the color tone compatibility and the mechanical properties due to possession of a certain light-diffusion.

In addition, processes for evaluating aesthetic properties of a composite restorative material are reported and, for example, JP-A 7-196429 describes that the transparency of a composite restorative material is evaluated by a contrast ratio, and a site to be applied is decided with the ratio so that an aesthetic and convenient cavity restoration can be carried out.

However, it is insufficient to evaluate the aestheticism only by the above factors. For example, a problem occurred that since the light transmission of the cured product becomes very strong as a filler becomes finer, when natural teeth are restored, the incongruity becomes very strong depending upon the background color, a material and a direction of the observation.

JP-A 9-169613 proposes that as evaluation of the optical properties close to those of natural teeth, from the distribution state of the light having transmitted through a composite restorative material, the distribution of transmitted light is numerically processed by using the diffusion factor (D).

Additionally, the dental compositions using the previous filler exhibited the unsatisfactory results, since when such the dental composition was filled as a restorative material or a prosthetic material, the unevenness of the diffusion light intensity due to the poor light diffusivity of a filler resulted in that, for example, the color tone varies depending upon a direction of observation and, consequently, the effect of color matching exhibited insufficiently.

In order to endow a composite restorative material with the excellent aestheticism, technical factors are in deed required, such as, control of refractive indices of a filler and a polymerizable monomer aiming at endowing with the transparency close to that of natural teeth, the fine-grinding of a filler aiming at endowing with the properties such as the polishability, the surface smoothrness glossiness after polishing, the impartation of the transmittance and the diffusion of the light in the interior of a composite restorative material aiming at reducing the effect of the background color and the dependency of the color tone on an observation angle, and the like. However, it is insufficient to evaluate the aestheticism only with these properties, and it is also essentially an important factor for expressing the aestheticism that the composite restorative-material has the color tone very close to that of natural teeth.

In the dental field, the impartation of the color tone to a dental composition such as a crown and bridge material, a filling material, a prosthetic material, an adhesive material, and a light-shielding material (opaque material), that is, the toning has hitherto been carried out by using a process of adding a pigment as it is or a process of diluting a pigment with components of a dental composition such as a polymerizable monomer and a filler to prepare a diluted pigment, then adding the diluted pigment (a master batch process). The former has better workability than the latter because the former does not include a step of preparing a diluted pigment. However, since in the toning of a dental composition, an amount of a pigment to be used is so small and there are a wide variety of color tone systems and colors, it is very difficult to finely adjust amounts of pigments. Moreover, a dispersibility is different depending upon, for example, a kind of a pigment and, therefore, the intended color can not be realized. On the other hand, the latter, comparing to the former, has problems in the workability and the cost because a diluted pigment obtained by diluting a pigment is used, and a step of preparing a diluted pigment is added, although a fine adjustment of an amount of a pigment to be added is possible. Moreover, the dispersibility of a pigment is better than the former, but not satisfactory. These toning processes are performed in the final step of preparing any dental compositions, and only mixing the pigments as mentioned above cannot produce the stable color tone and may affect other properties of a dental composition. This is because a pigment particle generally tends to aggregate easily due to a so small particle size and a large specific surface area, and because it is difficult to disperse uniformly due to the different surface characteristic in the compatibility of a pigment from those of components for a dental composition such as a polymerizable monomer and a filler, and the like. In addition, since the wettability with a polymerizable monomer and the like varies dependingupon a kind of a pigment to be used, a mixing ratio of a pigment to be used has the effect on characteristics of a dental composition paste. When the toning of a dental composition is actually performed, a polynerizable monomer, a filler, a pigment and the like are kneaded or stirred uniformly, but it is frequently observed that the color tone of the resulting dental composition changes depending upon a kind of a machine used and conditions such as a time for kneading or stirring. This is caused by the uneven dispersion of a pigment or the aggregation of a pigment or the like.

Further, a dental composition containing a large amount of a pigment is used in the dental field, and this is generally referred to as a light-shielding material (opaque material). This composition contains a large amount of a pigment having the strong light-shielding property, such as titanium white or carbon black and, in the case where a crown part of a tooth is defected by dental caries, it is used to remove a metallic color between a metal and a crown material (resin for crown and bridge material), when the defected part of the crown is compensated with a prosthetic crown (crown) combining the metal and the crown material (resin for crown and bridge material). Such a light-shielding material (opaque material) is, for example, a thermal polymerization type comprising a radical polymerizable monomer, an inorganic filler and a peroxide, which is disclosed in JP-A 61-127717 and JP-A 61-152715, and a cold curing type containing tributylborane, which is disclosed in *J. J Dent. Mater.*, vol.7, No.1 (p27–32, 1988). However, in these light-shielding materials (opaque materials), since a special equipment is required to heat, an available time for a work to apply on the metal surface is limited, and it takes a time to cure, clinical needs have shifted to a photopolymerization type. JP-A 59-110606 proposes a dental base material comprising a pigment such as zirconium dioxide, tungsten trioxide and titanium dioxide, a polymerizable monomer and a photocatalyst is described, and German Patent No. 3332179C2 proposes a photopolymerizable dental opacifying agent containing a photocatalyst and a mixture of zirconium dioxide and titanium dioxide as a pigment. These light-shielding materials (opaque materials) should have some fluidity and high opacifying effect in order to be applied on the metal surface in an even thickness. Since such materials have a pigment at a high content and the wettability between a pigment and a polymerizable monomer is poor, it is impossible to retain the initial dispersibility simply by mixing with a pigment, resulting in reaggregation. As the result, various problems arise that in the handling, for example, it can not be applied in an even thickness because the fluidity is decreased with time, and that in the physical properties, for example, it can not be polymerized well towards the deep parts because the light transmittance is decreased. In addition, since a pigment particle is small in a particle size, and a specific surface area is large and, therefore, the surface is very active, it is very difficult to disperse uniformly and stabilize such a pigment particle in a dental composition. However, in order to maintain the properties of a dental composition, the uniform dispersion of a pigment is an important factor.

Japanese Patent No. 2661708 proposes a photocurable light-shielding composition containing a pigment having the surface covered with a polymer, Japanese Patent No. 2812508 proposes a light-shielding composition containing a pigment having the surface treated with a titanate coupling agent, and JP-A 10-94552 proposes a dental photocurable opacifying agent containing a cross-linked bead-like polymer incorporating a color pigment. In all of them, aggregation between pigments is prevented to improve the dispersibility of a pigment by treating or covering the surface of the pigment with a polymer or a surface treating agent, or by incorporating a pigment in a bead-like polymer. In addition, since the above modification of the pigment surface does not contact the active surface of a pigment directly withia polymerizable monomer in a composite restorative material, an improvement is made regarding the characteristics of a paste and the polymerizability of a polymerizable monomer. However, even in these modified pigments, the dispersion state is not still insufficient in a dental composition, and the wettability with a polymerizable monomer is poor.

Further, even when the surfaces of these pigments are treated with, for example, a silane coupling agent which is known in the dental field to improve the compatibility with a polymerizable monomer, since the pigment surface is treated or covered with an organic compound, a surface treating agent does not act effectively and, thus, the sufficient surface treatment effect can not be obtained. When these pigments are used in a dental composition, the stable color tone can not be obtained in a toning step and, furthermore, problems arise in the mechanical properties because defects are produced in the vicinity of the interface between a pigment and a matrix in which a polymerizable monomer is cured.

As mentioned above, there is not a pigment which can be used in a step of endowing various dental compositions in the dental field with the color tone and can impart the excellent dispersibility and the stable color developing property thereto. In addition, a pigment has hitherto been used aiming at endowing a dental composition with the color tone, and there is no pigment which contributes to the stability of a paste, the mechanical properties and the optical properties.

An object of the present invention is to provide a inorganic filler which can be utilized in a dental composition such as a crown and bridge material, a filling material, a prosthetic material, an adhesive material and the like in the dental field, and which can impart the excellent wear resistance and the excellent glossiness after polishing to a dental composition without deteriorating properties such as the mechanical strength and the hardness which are required as a dental composition, as well as a process for producing the same.

Another object of the present invention is to provide a multi-functional filler which can be used in a dental composition such as crown and bridge material, a filling material, a prosthetic material, an adhesive material and the like in the dental field, and which can provide a dental compositon with the excellent color adaptation based on the diffusivity to the incident light and the excellent sustained fluoride releasablity without deteriorating the properties required for a dental material, such as the mechanical strength and the hardness, and a process for producing the same.

Another object of the present invention is to provide an organic compound filler which is usable in a dental composition in the dental field such as a crown and bridge material, a filling material, a prosthetic material, an adhesive material and the like, and which can impart the excellent mechanical strength, the excellent durability and the excellent stable handling as a paste without deteriorating properties such as the polishability, the surface smoothness and glossiness after polishing required as filling material, and a process for producing the same.

Another object of the present invention is to provide a modified filler which can be employed for a dental composition such as a crown and bridge material, a filling material, a prosthesis material, an adhesive material and the like in the dental field, and which maintains the excellent polishability and the excellent optical property such as the surface smoothness and glossiness required as a filling material and, at the same time, can impart the mechanical strength, the wear resistance and the coloring resistance as well as a process for producing the same.

Another object of the present invention is to provide a coloring filler which have so excellent properties in dispersion and color development as to impart the color tone to a dental composition such as a crown and bridge material, a filling material, a prosthetic material, an adhesive material, a light-shielding material (an opaquematerial) and the like in the dental field, and which can impart the excellent paste stability, the excellent mechanical properties and the excellent optical properties thereto.

Further object of the present invention is to provide a process for producing a coloring filler and a dental composition containing the same.

SUMMARY OF THE INVENTION

In the first aspect, the present invention relates to an inorganic filler which comprises an inorganic fine particle having an average particle size of 0.01~5 μm, the inorganic fine particle having the surface covered with polysiloxane.

Also, the present invention relates to a process for producing the aforementioned inorganic filler, which comprises:

(1) a wet-grinding step of fine-grinding a raw material inorganic particle into inorganic fine particles having an average particle size of 0.01~5 μm; and (2) a step of forming a polysiloxane film on the surface of the resulting inorganic fine particle.

More particularly, the present invention relates to a process for producing the aforementioned inorganic filler, wherein said step of forming a polysiloxane film comprises:

(2-1) a step of hydrolyzing or partially hydrolyzing a silane compound represented by the general formula (I):

wherein, Z is RO— or OCN—, X is halogen, Y is —OH, R is an organic group having a carbon number of 8 or less, and n, m and L are an integer of 0 to 4, provided that n+m+L=4, (a combination of two or more of said silane compound may be used) in the presence of the inorganic fine particle dispersed in an aqueous medium, then condensing the resulting silanol compound;

(2-2) a step of drying the resulting aqueous dispersion; and (2-3) a step of disintegrating the dried material to an average particle size of 0.01~5 μm.

In addition, the present invention relates to a dental composition comprising the aforementioned inorganic filler in the state in which the surface thereof has been treated with an organosilane compound.

According to the first aspect of the present invention, the following various effects are exerted:

(1) A fine and uniform inorganic filler can be obtained and, since the filler has been covered with polysiloxane without any aggregation, it can be dispersed in a composition in the state of a fine particle having a particle size of 0.01~5 μm without any secondary aggregation and, thereby, the excellent optical properties and polishability which are characteristic of the fine particle filler can be retained.

(2) Since an inorganic filler is covered with polysiloxane, the conventional silane coupling agent can effectively act on the inorganic filler, and the inorganic filler can be uniformly dispersed in a matrix composed mainly of an organic polymer material. For this reason, in spite of a filler having a fine particle size, the strength and the wear resistance of a composition can be improved.

In the second aspect, the present invention relates to a multi-functional filler, comprising an inorganic particle containing an acid reactive element, wherein a cement reactive phase is formed on the surface of the inorganic particle, and the cement reactive phase is further covered with polysiloxane.

The present invention also relates to a multi-flnctional filler wherein the inorganic particle is a glass.

The present invention further relates to a multi-functional filler wherein the inorganic particle is a fluoride-containing glass.

The present invention additionally relates to a process for producing the above multi-functional filler, which comprises: reacting an acidic polymer with an acid reactive element-containing inorganic fine particle covered with polysiloxane (hereinafter abbreviated to as "a polysiloxane-covered inorganic fine particle").

More specifically, the present invention relates to a process for producing the above multi-functional filler, wherein an acid reactive element-containing inorganic fine particle covered with polysiloxane is obtained by hydrolyzing or partially hydrolyzing, in an aqueous dispersion containing the acid reactive element-containing inorganic fine particle, a silane compound represented by the general formula (I):

(I)

wherein Z is RO— or OCN—, X is halogen, Y is —OH, R is an organic group having a carbon number of 8 or less, and n, m and L are an integer of 0 to 4, provided that n+m+L=4, and then condensing the obtained silanol compound.

Further, the present invention relates to a process for producing the above multi-functional filler, wherein an acid reactive element-containing inorganic particle covered with polysiloxane is obtained by condensing a low-condensed silane compound obtained by partially hydrolyzing, in an aqueous dispersion containing the acid reactive element-containing inorganic fine particle, a silane compound represented by the general formula (I):

(I)

wherein Z is RO— or OCN—, X is halogen, Y is —OH, R is an organic group having a carbon number of 8 or less, and n, m and L are an integer of 0 to 4, provided that n+m+L=4, followed by partial condensation.

Still further, the present invention relates to a dental composition comprising any of the above multi-functional fillers in the state where the surface is treated with an organosilane compound represented by the general formula. (II):

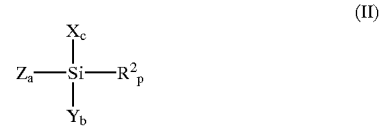

(II)

wherein Z is $R^1O$— or OCN—, X is halogen, Y is —OH, $R^1$ is an organic group having a carbon number of 8 or less, $R^2$ is an organic group, p is an integer of 1~ to 3, and a, b and c are an integer of 0 to 3, provided that a+b+c+p=4.

Particularly, the present invention relates to a dental composition comprising (a) any of the above multi-functional fillers, (b) a polymerizable monomer, and (c) a polymerization initiator.

According to the second aspect of the present invention, the following effects are exerted:

(1) The multi-functional filler of the present invention is characterized in that the light hittered against the present filler is diffused in a wide range of an angle because the filler has a three-layered structure in which the cement reactive phase is formed on the surface of the core inorganic fine particle, and the outside thereof is further covered with polysiloxane. Thus, in a dental composition having the present multi-functional filler incorporated therein, since the incident light can uniformly diffuse towards any direction, the dependency of the colortone on an observation angle is small and, consequently, the same color intended can be observed in any direction after the dental composition is filled in teeth; and (2) Since the cement reactive phase of the present multi-functional filler is porous, the sustained fluoride releasability can be imparted to a dental composition comprising the multi-functional filler of the present invention by using a fluoride-containing glass as an inorganic fine particle constituting the core.

In order to accomplish the above object, the present inventors studied intensively, and as a result, solved the above problem by providing an organic compound filler comprising an organic-inorganic polymer particle or an organic polymer particle having the surface covered with an inorganic film. That is, the inventors provide the following inventions in this application.

In the third aspect, the present invention provides an organic compound filler, which comprises an organic-inorganic polymer particle or an organic polymer particle, wherein the surface of the organic-inorganic polymer particle or the organic polymer particle is covered with an inorganic film, wherein the inorganic film is a condensate obtained by hydrolyzing or partially hydrolyzing a silane compound represented by the general formula (I):

(I)

wherein Z is RO— or OCN—, X is halogen, Y is OH —OH, R is an organic group having a carbon number of 8 or less, and n, m and L are an integer of 0~ to 4, provided that n+m+L=4, and/or a low-condensate of the silane compound.

The present invention also provides an organic compound filler, wherein the inorganic film is a co-condensate obtained by hydrolyzing or partially hydrolyzing a silane compound represented by the general formula (I) and/or the low-condensate of the silane compound in the presence of an organosilane compound represented by the general formula (II):

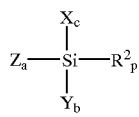

(II)

wherein Z is $R^1O$— or OCN—, X is halogen, Y is —OH, $R^1$ is an organic group having a carbon number of 8 or less, $R^2$ is an organic group, a, b and c are an integer of 0~ to 3, and p is an integer of 1~ to 3, provided that a+b+c+p=4, and/or a low-condensate of the organosilane compound.

In addition, the present invention provides an organic compound filler, wherein the inorganic film is a co-condensate obtained by hydrolyzing or partially hydrolyzing the silane compound represented by the general formula (I) and/or the low-condensate of the silane compound in the presence of a metal compound.

Further, the present invention provides an organic compound filler, wherein the inorganic film is a co-condensate obtained by hydrolyzing or partially hydrolyzing the silane comrpound represented by the general formula (I) and/or the low-condensate of the silane compound in the presence of the organosilane compound represented by the general formula (II) and/or the low-condensate of the organosilane compound and a metal compound.

Still further, the present invention provides a process for producing the above organic compound filler, which comprises: a step of preparing a dispersion by dispersing an organic-inorganic polymer particle or an organic polymer particle in an aqueous medium, a step of forming an inorganic film on the surface of the particle in the resulting dispersion, a step of separating and/or heat-treating the particle having the inorganic film formed thereon, and a step of disintegrating the heat-treated granule to primary particles.

More specifically, the present invention provides a process for producing the organic compound filler, wherein the step of forming an inorganic film comprises: hydrolyzing or partially hydrolyzing a silane compound represented by the general formula (I):

(I)

wherein Z is RO— or OCN—, X is halogen, Y is —OH, R is an organic group having a carbon number of 8 or less, and n, im and L are an integer of 0~ to 4, provided that n+m+L=4, and/or a low-condensate of the silane compound in the presence of an organic-inorganic polymer particle or an organic polymer particle dispersed in an aqueous medium, followed by condensing; or hydrolyzing or partially hydrolyzing the silane compound represented by the general formula (I) and/or the low-condensate of the silane compound in the presence of at least one of an organosilane compound represented bythe general formula (II):

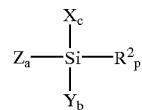

(II)

wherein Z is $R^1O$— or OCN—, X is halogen, Y is —OH, $R^1$ is an organic group having a carbon number of 8 or less, $R^2$ is an organic group, a, b and c are an integer of 0~ to 3, and p is an integer of 1~ to 3, provided that a+b+c+p=4, a low-condensate of the organosilane compound and a metal compound, followed by co-condensing.

Finally, the present invention provides a dental composition comprising (a) an organic compound filler of the present invention, (b) a polymerizable monomer, and (c) a polymerization initiator.

According to the third aspect of the present invention, the following effects are exerted by covering the surface of the organic-inorganic polymer particle or an organic polymer particle with an inorganic film.

(1) Since the surface of the conventional organic-inorganic polymer particle or organic polymer particle has a little amount of an inorganic component and almost all components on the surface is an organic component, a surface treating agent such as a silane coupling agent can not act effectively and, to the contrary, since the present organic compound filler is covered with an inorganic film, a surface treating agent such as a silane coupling agent can act effectively to disperse uniformly in a resin matrix.

(2) When the organic compound filler of the present invention is used in a dental composition as a filler, it can impart the excellent polishability, particularly the surface smootlness and glossiness after polishing, as well as the excellent mechanical properties and the excellent durability, and the excellent stable paste handling.

(3) In addition, by incorporating a heavy metal element into the covering inorganic film, the radiopacity can be additionally impartred.

In order to accomplish the above object, the present inventors studied intensively and, as a result, solved the problems by providing a modified filler in which the surface of an inorganic fine particle having an average particle size of 0.01~5 μm is covered with polyorganosiloxane. That is, the present inventors provide the following invention in this application.

In the fourth aspect, the present invention provides a modified filler which comprises an inorganic fine particle having an average particle size of 0.01~5 μm and having the surface covered with polyorganosiloxane, said polyorganosiloxane is a co-condensate -obtained by hydrolyzing or partially hydrolyzing a silane compound represented by the general formula (I):

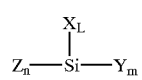

(I)

wherein Z is RO— or OCN—, X is halogen, Y is —OH, R is an organic group having a carbon number of 8 or less, and n, m and L are all an integer of 0~ to 4, provided that m+n+L=4, and/or a low-condensate of the silane compound and an organosilane compound represented by the general formula (II):

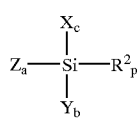
(II)

wherein Z is R¹O— or OCN—, X is halogen, Y is —OH, R¹ is an organic group having a carbon number of 8 or less, R² is an organic group, p is an integer of 1 to 3, and a, b and c are all an integer of 0~ to 3, provided that a+b+c+p=4, and/or a low-condensate of the organosilane compound.

Further, the present invention provides a modified filler in which the polyorganosiloxane is a co-condensate obtained by hydrolyzing or partially hydrolyzing a silane compound represented by the general formula (I) and/or a low-condensate of the silane compound and an organosilane compound represented by the general formula (II) and/or a low-condensate of the organosilane compound in the presence of a metal compound.

In addition, the present invention provides a process for producing the above-mentioned modified filler which comprises (1) a wet-grinding step of fine-grinding a raw material inorganic particle into inorganic particles having an average particle size of 0.01~5 μm, or a wet-dispersion step of disintegrating an aggregated inorganic particle into primary particles, the primary particle having an average particle size of 0.01~5 μm, and (2) a step of forming a polyorganosiloxane film on the surface of the resulting inorganic fine particle.

More particularly, the present invention provides a process for producing the above-mentioned modified filler in which the step of forming a polyorganosiloxane film comprises (2-1) a step of hydrolyzing or partially hydrolyzing a silane compound represented by the general formula (I):

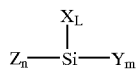
(I)

wherein Z is RO— or OCN—, X is halogen, Y is —OH, R is an organic group having a carbon number of 8 or less, and n, m and L are an integer of 0~ to 4, provided that n+m+L=4, and/or a low co-condensate of the silane compound and an organosilane compound represented by the general formula (II):

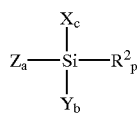
(II)

wherein Z is R¹O— or OCN—, X is halogen, Y is —OH, R¹ is an organic group having a carbon number of 8 or less, R² is an organic group, p is an integer of 1μ to 3, and a, b and c are all an integer of 0~ to 3, provided that a+b+c+p=4, and/or a low co-condensate of the organosilane compound, and co-condensing the resulting silanol compound, or a step of hydrolyzing or partially hydrolyzing a silane compound represented by the general formula (I) and/or a low-condensate of the silane compound and an organosilane compound represented by the general formula (II) and/or a low-condensate of the organosilane compound in the presence of a metal compound and, then, co-condensing the silanol compound, (2-2) a step of heat-treating the resulting aqueous dispersion, and (2-3) a step of disintegrating the heat-treated solidified material to an average particle size of 0.01~5 μm.

Furthermore, the present invention provides a dental composition which comprises (a) the aforementioned modified filler, (b) a polymerizable monomer, and (c) a polymerization initiator.

According to the fourth aspect of the aforementioned present inventions, the following effects are exerted.

(1) By forming a polyorganosiloxane film on the surface of an inorganic fine particle which was fine-ground by fine-grinding or dispersion techniques, a modified filler can be obtained in the state of a fine particle of 0.01~5 μm without secondary aggregation.

(2) The resulting fine and uniform modified filler can be dispersed in a dental composition in the state of a primary particle without secondary aggregation and the optical properties such as the excellent polishability and the surface smoothness of a fine particle filler are retained. In addition, this polyorganosiloxane film reforms only the surface of an inorganic fine particle and the properties originally harbored by an inorganic fine particle are maintained.

(3) Since a modified filler is covered with polyorganosiloxane, an organosilane compound such as a silane coupling agent which has previously been used can effectively exert its action irrespective of a kind of an inorganic fine particle and the wettability with a resin matrix can be further improved. Such a modified filler is dispersed in a dental composition more uniformly and, together with the effect of formation of a polyorganosiloxane film, the mechanical strength and the wear resistance can be improved in spite of a fine filler.

In order to accomplish the above object, the present inventors studied intensively and, as a result, found that by covering the surfaces of an inorganic particle and a coloring particle with poly(organo)siloxane in the state where both particles were mixed and dispersed uniformly, a coloring filler in which a coloring particle is fixed in the state of a primary particle and is uniformly dispersed can be provided, which resulted in the solution of the above problems.

That is, we provide the following inventions in this application.

In the fifth aspect, the present invention provides a dental coloring filler, which comprises an inorganic particle and a coloring particle, wherein the inorganic particle and the coloring particle are uniformly mixed and dispersed, the surfaces of these particles are covered with poly(organo)siloxane, and poly(organo)siloxane is a condensate obtained by hydrolyzing or partially hydrolyzing a silane compound represented by the general formula (I):

(I)

wherein Z is RO— or OCN—, X is halogen, Y is —OH, R is an organic group having a carbon number of 8 or less, and n, m and L are an integer of 0~ to 4; provided that n+m+L=4, and/or a low-condensate of the silane compound.

The present invention also provides a dental coloring filler, wherein poly(organo)siloxane is a co-condensate obtained by hydrolyzing or partially hydrolyzing a silane compound represented by the general formula (I) and/or a low-condensate of the silane compound in the presence of an organosilane compound represented by the general formula (II):

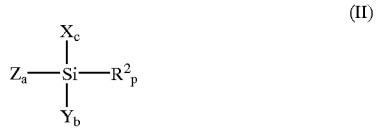

wherein Z is R¹O— or OCN—, X is halogen, Y is —OH, R¹ is an organic group having a carbon number of 8 or less, R² is an organic group, p is an integer of 1~ to 3, and a, b and c are an integer of 0~ to 3, provided that a+b+c+p=4, and/or a low-condensate of the organosilane compound.

In addition, the present invention provides a dental coloring filler, wherein poly(organo)siloxane is a co-condensate obtained by hydrolyzing or partially hydrolyzing the silane compound represented by the general formula (I) and/or the low-condensate of the silane compound in the presence of a metal compound.

Further, the present invention provides a dental coloring filler, wherein poly(organo)siloxane is a co-condensate obtained by hydrolyzing or partially hydrolyzing the silane compound represented by the general formula (I) and/or the low-condensate of the silane compound in the presence of the organosilane compound represented by the general formula (II) and/or the low-condensate of the organosilane compound and a metal compound.

Still further, the present invention provides a process for producing the above dental coloring filler, which comprises (1) a step of preparing a mixed particle by uniformly mixing and dispersing an inorganic particle and a coloring particle, and (2) a step of forming a poly(organo)siloxane film on the surface of the resulting mixed particle.

More specifically, the present invention provides a process for producing a dental coloring filler, wherein the step of forming a poly(organo)siloxane film comprises:

in the presence of a mixed particle which is uniformly niixed and dispersed, hydrolyzing or partially hydrolyzing a silane compound represented by the general formula (I):

wherein Z is RO— or OCN—, X is halogen, Y is —OH, R is an organic group having a carbon number of 8 or less, and n, m and L are an integer of 0~ to 4, provided that n+m+L=4, and/or a low-condensate of the silane compound, followed by condensing; or in the presence of a mixed particle which is uniformly mixed and dispersed, hydrolyzing or partially hydrolyzing the silane compound represented by the general formula (I) and/or the low-condensate of the silane compound in the presence of at least one of an organosilane compound represented by the general formula (II):

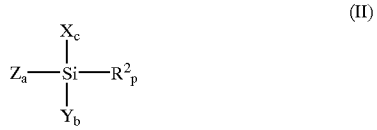

wherein Z is R¹O— or OCN—, X is halogen, Y is —OH, R¹ is an organic group having a carbon number of 8 or less, R² is an organic group, p is an integer of 1~ to 3, and a, b and c are an integer of 0µ to 3, provided that a+b+c+p=4, a low-condensate of the organosilane compound and a metal compound, followed by co-condensing.

Finally, the present invention provides a dental composition, which comprises (a) a dental coloring filler of the present invention, (b) a polynernzable monomer and (c) a polymerization initiator.

Furthermore, the present invention provides a dental composition further comprising (d) a filler.

According to the fifth aspect of the present invention, following effects are exerted.

(1) In the coloring filler of the present invention, an inorganic particle and a coloring particle are mixed and dispersed uniformly, and the surfaces of these particles are covered with poly(organo)siloxane. Since the coloring particle is fixed in the state of a primary particle by the poly(organ)siloxane film, it does not aggregate and, therefore, it is excellent in color development as well as in dispersibility in a dental composition.

(2) Generally, a dental composition is endowed with the color tone by using a diluted pigment in which a pigment is diluted in advance. However, since in the present coloring filler, an inorganic particle and a coloring particle have been already dispersed uniformly, a step of preparing a diluted pigment is not required and, further, the pigment concentration can be freely adjusted. The toning by using the present coloring filler allows for clear and abundant colors as requested by clinicians.

(3) Since an inorganic particle and a coloring particle in the present coloring filler are covered with poly(organo) siloxane, a surface treating agent such as a silane coupling agent which has hitherto been used is possible to act effectively, and the wettability with a resin matrix in a dental composition can be further improved. Such coloring filler can be dispersed more uniformly in a dental composition and, by combining with the effect of forming a poly(organo) siloxane film, the coloring filler endows a dental composition with the color tone and, additionally, can contributes to, for example, the mechanical properties, the optical properties and the stability of the paste characteristics.

DETAILED DESCRIPTION OF THE INVENTION

Figure 1:
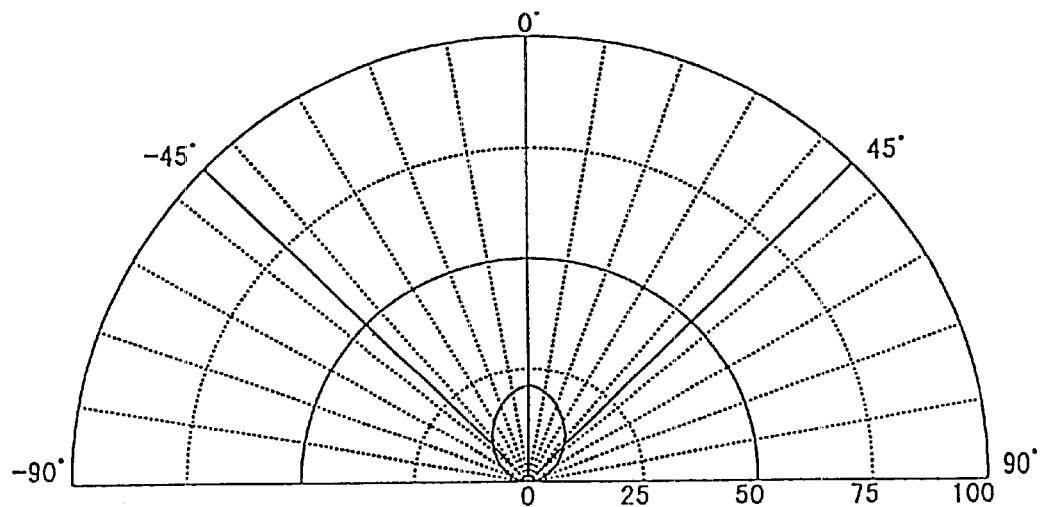
FIG. 1 is a view showing a measured angular distribution of the transmitted light intensity: (a) the present invention (Example B-3), (b) Comparative Example B-1.
Figure 1:
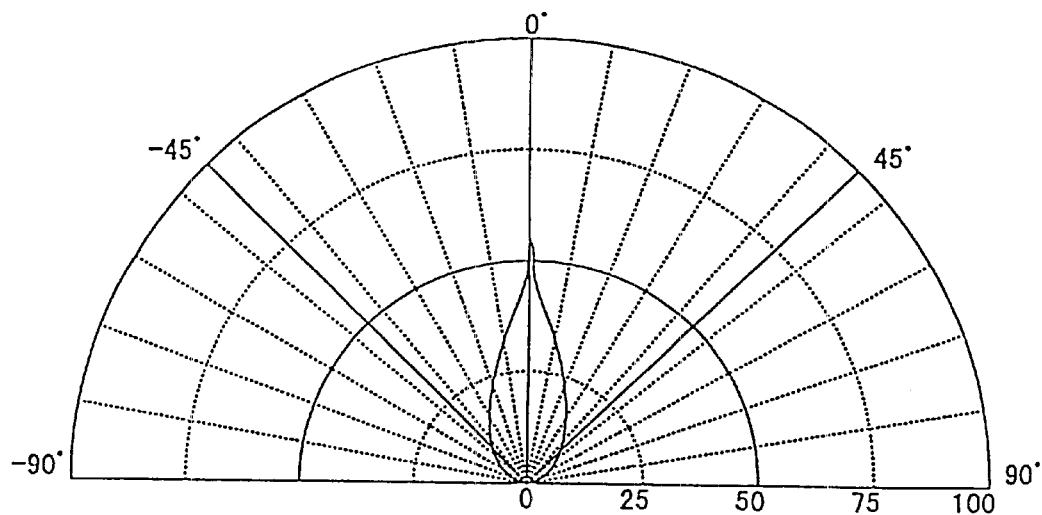

The inorganic filler of the first aspect of the present invention comprises an inorganic fine particle having an average particle size of 0.01~5 µm, the surface of which is covered with polysiloxane. Since the inorganic filler has such a small particle size and is a monodisperse particle having the narrow particle size distribution, a dental composition such as a dental restorative material, comprising the inorganic filler of the present invention, has the smoothness which can manifest the excellent glossiness on the polished surface after curing. Also, although in the case where such the fine particle filler is contained, a dental composition is apt to wear and is inferior in the durability, a dental composition comprising the inorganic filler of the present invention has the excellent wear resistance since the inorganic filler is uniformly and strongly adhered to a matrix in the composition without any aggregation.

The inorganic fine particle having an average particle size of 0.01~5 μm to be used in the present invention is not particularly limited to, but includes, for example, quartz, amorphous silica, aluminium silicate, aluminium oxide, titanium oxide, zirconium oxide, various glasses (including a glass prepared by a melting process, a synthetic glass prepared by a sol-gel process, a glass produced by a vapor phase process), calcium carbonate, talc, kaolin, clay, mica, Mluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite and the like. Particularly preferred are glasses. Glasses are preferred in that they can impart the necessary functions as a dental composition since they have the lower hardness as compared with that of a silica compound, are superior in optical transmission property, and can contain elements shutting off the X-ray or fluoride. Most preferred are an aluminosilicate glass, a borosilicate glass, an aluminoborate glass and a boroaluminosilicate glass which contain fluoride and heavy metals such as strontium, barium and lanthanum. Provided that, since the inorganic fine particle having an average particle size of 0.01~5 μm to be used in the present invention is obtained through a wet-grinding step or a wet-dispersing step in water or an aqueous medium, a water-soluble inorganic fine particle, for example, of metal fluorides such as sodium fluoride, calcium fluoride and strontium fluoride is excluded.

This inorganic fine particle having an average particle size of 0.01~5 μm can be obtained by wet-grinding a commercially available raw material inorganic particle which is generally used as a filler or the like. Wet-grinding does not require any special procedure, and it can be conducted by taking the procedure generally used in the art. For example, a raw material inorganic particle may be fine-ground by using container-driven medium mills such as a ball mill and an oscillating mill or grinding medium-agitating mills such as an attritor, a sand grinder, an annealer mill and a tower mill in the presence of an aqueous medium. As an aqueous medium, water alone or a medium in which all or a part of water is substituted with an aqueous solvent such as alcohols, ketones such as acetone and the like or ethers and the like, as necessary may be used. In the case of using these aqueous solvents, the cohesive power of the solidified material after drying is weaken and, thereby, disintegration can be easily conducted. The conditions for wet-grinding including a grinding time may be arbitrarily selected depending upon the desired average particle size of an inorganic fine particle, although it varies depending upon the size, the hardness or an amount of a raw material inorganic particle to be added, an amount of water or an aqueous solvent to be added, or a kind of a grinding machine. In another process for producing an inorganic fine particle having an average particle size of 0.01~0.5 μm, it can be obtained by wet-dispersing an aggregate of inorganic fine particles of 0.01–5 μm as a primary particle in the presence of water or an aqueous medium. A wet-dispersing step does not require any special procedure, and it can be conducted by taking the procedure generally used in the art. For example, it may be conducted by dispersing aggregated inorganic fine particles using a wet-dispersing machine such as a dissolver and a homogenizer in the presence of an aqueous medium. The condition for dispersion such as a dispersing time, an agitator and a rotating speed may be arbitrarily selected depending upon the desired average particle size of an inorganic fine particle, although it varies depending upon the size, the hardness or an amount of aggregated inorganic fine particles to be added, an amount of water or an aqueous medium to be added, or a kind of a dispersing machine.

A polysiloxane film is formed on the surface of the resulting inorganic fine particle as follows. At a point when the particle is fine-ground or disintegrated to the desired average particle size, a silane compound represented by the general formula (I):

wherein Z is RO— or OCN—, X is halogen, Y is —OH, R is an organic group having a carbon number of 8 or less, and n, m and L are an integer of 0 to 4, provided that n+m+L=4, is mixed into an aqueous dispersion of the resulting inorganic fine particle, then the mixture is hydrolyzed or partially hydrolyzed in the system, which is then condensed via a silanol compound. Although, in the case of the above process for forming a polysiloxane film, hydrolysis and condensation of a silane compound and formation of a polysiloxane film on the surface of an inorganic fine particle are simultaneously proceeded in the same system, another process for forming a polysiloxane film in which hydrolysis and condensation of a silane compound are conducted to produce a low-condensed silane compound (oligomer) in the separated system and then the low-condensed silane compound is mixed into the aqueous dispersion of an inorganic fine particle. obtained by a wet-grinding step or a wet-dispersing step can more effectively form a polysiloxane film on the surface of an inorganic particle. More preferable is a process for forming a polysiloxane film by mixing a commercially available low-condensed silane compound (oligomer) without passing through a low-condensed compound production step. The reason why this process is preferable can be considered as follows. When a silane compound monomer is used, a polysiloxane film can not be uniformly formed on the surface of an inorganic fine particle because condensation is three-dimensionally caused and self-condensation is dominantly proceeded because of the presence of a large amount of water during a polysiloxane film forming step. On the other hand, when a low-condensed silane compound (oligomer) is used, it can be considered that a polysiloxane film may be uniformly formed on the surface of an inorganic fine particle in a unit having a polysiloxane main chain of a certain length. The structure of such the low-condensed silane compound (oligomer) is not particularly limited to, but the linear chain structure is more preferable than the three dimensional structure, and a degree of polymerization thereof is preferably in a range of 2~20, more preferably in a range of 2~6, since the condensation reactivity is lowered and formation of a polysiloxane film on the surface of an inorganic particle is deteriorated in a higher degree of polymerization. The above degree of polymerization corresponds to a molecular weight range of 500~600. In the case of preparation of a low-condensed silane compound (oligomer) having the straight chain structure in the separated system, it is necessary to conduct preparation with a small amount of water such that hydrolysis and condensation of a silane compound monomer are partially proceeded, and such the preparation can be conducted by using acids, alkalis or other catalysts used in a sol-gel process. Thereby, the system becomes the state where an inorganic fine particle having an average particle size of 0.01~5 μm is fine-dispersed, without any association, in an aqueous medium in which a condensed silane compound, that is, polysiloxane is dispersed.

The above hydrolysis or partial hydrolysis of a silane compound in an aqueous dispersion is conducted at a temperature in a range of room temperature to 100 C, preferably in a range of room temperature to 50 C for a few minutes to a few ten hours, preferably for 30 minutes to 4 hours, with stirring at a relatively low rotating speed. Stirring does not require any special procedure, and the equipment conventionally used in the art can be adopted. For example, a stirrer which can stir the slurry-like material such as a universal mixer and a planetary mixer may be used to stir. There is no problem when a stirring temperature is not greater than a boiling point of an aqueous medium. A stirring time should be adjusted since a gelling rate by condensation is influenced by a kind and an amount of a silane compound or a low-condensed silane compound, a kind, a particle size and a proportion in an aqueous dispersion of an inorganic fine particle, and a kind of an aqueous medium, and stirring should be continued until a gel is formed. Stirring should be conducted at a low speed since the gel structure is disintegrated and a uniform film is not formed at a too high speed. As used herein, the term "gel" means the creamy or gelatinous state in which condensation is grown to absorb an aqueous medium leading to swelling. As used herein the term "a gelling rate" means a speed at which such the state appears. Addition of the sol-gel catalysts such as an acid, an alkali, an organometallic compound, a metal alkoxide and a metal chelate compound for the purpose of accelerating a gelling rate is a preferred aspect in a sense of accelerating a gelling rate. The catalyst include, for example, inorganic acids such as hydrochloric acid, acetic acid, nitric acid, formic acid, sulfuric acid and phosphoric acid, organic acids such as para-toluenesulfonic acid, benzoic acid, phthalic acid and maleic acid, and alkali catalysts such as potassium hydroxide, sodium hydroxide and ammonia. The acid or alkali used as a catalyst is largely involved in not only adjustment of a gelling rate but also electrification of the surface of an inorganic fine particle as a pH adjusting agent to allow a uniform polysiloxane film to be formed. However, it is necessary that acids or alkalis are appropriately selected since they have the influence on a raw material of an inorganic fine particle. Also, addition of an alcohol to this step has the significant effect that aggregation of inorganic fine particles is decreased during a drying step and disintegration is enhanced. Preferred alcohols are of 2 to 10 carbon atoms, and alcohols of not less than 10 carbon atoms require a longer period of time for evaporating the solvent since they have a higher boiling point. Alcohols include, for example, ethyl alcohol, n-propyl alcohol, isopropyl alcohol, n-butyl alcohol, t-butyl alcohol, isobutyl alcohol, n-pentyl alcohol, isoamyl alcohol, n-hexyl alcohol, n-heptyl alcohol, n-octyl alcohol and n-dodecyl alcohol. More preferably, alcohols of 2 to 4 carbon atoms such as ethyl alcohol, n-propyl alcohol and isopropyl alcohol are suitably used.

An amount of the alcohol to be added is 5 to 100% by weight, preferably 5 to 20% by weight relative to water. Furthermore, this amount also contains an amount of an alcohol contained during the wet-grinding or wet-dispersing step. When the amount exceeds 100% by weight, problems such as the complication of the drying step arise. The content of an inorganic fine particle is in a range of 25~100% by weight, preferably in a range of 30~75% by weight relative to an aqueous medium. When the content exceeds 100% by weight, a gelling rate by condensation becomes larger, formation of a uniform polysiloxane film is difficult and, on the other hand, when the content is below 25% by weight, an inorganic fine particle settles under the stirring condition and phase separation occurs in an aqueous dispersion.

An amount of a silane compound to be added depends upon a particle size of an inorganic fine particle and is in a range of 0.1~100% by weight, preferably in a range of 0.1~4% by weight in terms of $SiO_2$ relative to an inorganic fine particle. When the amount is below 0.1% by weight, the effect of formation of a polysiloxane film is not manifested and particles can not be disintegrated to a primary particle and remain aggregated and, on the other hand, when the amount exceeds 10% by weight, the solidified material after drying becomes too hard to disintegrate.

Then, the system in such the gelated state is dried and an aqueous medium is removed to solidify. A drying step consists of two stages of aging and sintering, and the former stage is aimed at growing the gel structure and removing an aqueous medium, and the latter stage is aimed at reinforcing the gel structure. The former stage should be conducted by allowing to stand so as not to impart distortion to the gel structure and so as to remove an aqueous medium and therefore, it is preferably conducted in an equipment such as a box-type heat dryer. An aging temperature is in a range of room temperature to 100 C, preferably in a range of 40 to 80 C. When tile temperature is lower than the above range, then removal of an aqueous medium becomes insufficient and, on the other hand, when the temperature exceeds the above range, then an aqueous medium is rapidly evaporated and, thereby, there is a possibility that an imperfection is produced in the gel structure or the gel structure is peeled from the surface of an inorganic fine particle. An aging time may be any time as long as it is sufficient for removing an aqueous medium since it varies depending upon the ability of a dryer and the like. On the other hand, the sintering step consists of temperature rising and holding, and the former is preferably conducted by gradually rising a temperature to the desired temperature for a longer period of time, and there is a possibility that distortion may be produced in the gel structure by rapid temperature rising since the thermal conductivity of the gel dispersion is low. The latter is a sintering at a constant temperature, and atime therefor is 10 to 100 hours, more preferably 10 to 50 hours. Although the greater effect is obtained as this time is longer, no effect is observed above a certain time. A sintering temperature is in a range of 100 to 350 C, more preferably of 100 to 200 C. The temperature should be appropriately selected so as not to influence on a raw material of an inorganic fine particle and not to make the porous gel structure non-porous. In this way, an aqueous medium is removed from the gel by drying to obtain a constricted solidified material. Although the solidified material is in the state of aggregated inorganic fine particles, it is not a mere aggregate of inorganic fine particles, and a polysiloxane film formed by condensation intervenes on the boundary surface of individual fine particle. Accordingly, as the next step, when the solidified material is disintegrated to a size corresponding to that of an inorganic fine particle before forming a polysiloxane film, then the separated particle having the surface covered with a polysiloxane film, that is, an inorganic filler of the present invention can be obtained. As used herein, the term "disintegrated to a size corresponding to that of an inorganic fine particle before forming a polysiloxane film" means disintegration to an inorganic fine particle, and the difference from the original inorganic fine particle is that the separated, inorganic fine particle is covered with polysiloxane. Provided that, the secondary aggregate may be contained to a non-problematic degree. Disintegration of a solidified material may be easily conducted by applying it a shearing force or an impact force, and a disintegrating process may be conducted by using, for example, a Henschel mixer, a cross rotary mixer, a super mixer or the like.

In the compound represented by the general formula (I), Z represents an RO— or OCN— group which can produce a silanol group by hydrolysis, X represents halogen, Y represents an OH group. Specifically, for example, R represents an alkyl group or an alkyl derivative group such as methyl, ethyl, 2-chloroethyl, allyl, aminoethyl, propyl, isopentyl, hexyl, 2-methoxyethyl, phenyl, m-nitrophenyl and 2,4-dichlorophenyl, but preferably R is methyl or ethyl from a viewpoint of hydrolysis rate or a remaining carbon in a polysiloxane film, and halogen is chlorine or bromine, preferably is chlorine.

The silane compound represented by the general formula (I) includes, for example, tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydcoxysilane, diethoxydichlorosilane, tetraphenoxysilane, tetrachlorosilane, silicon hydroxide (silicon oxide hydrate), silane tetraisocyanate and silane ethoxytriisocyanate, preferably tetramethoxysilane and tetnaethoxysilane. A low-condensed compound of the silane compound represented by the general formula (I) is more preferable. An example thereof is a low-condensed silane compound which is prepared by partially hydrolyzing and then condensing tetramethoxysilane and tetraethoxysilane. These compounds may be used alone or in combinationthereof. An organosilane compound also may be added as a part of the silane compound represented by the general forrmula (I) upon formation of a polysiloxane film. Specifically, the organosilane compound include, for example, methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloxypropyltrimethoxysilane, γ-glycidoxypropylmethoxysilane, γ-mercaptopropyltrimethoxysilane, γ-amihopropyltriethoxysilane, 3-aminopropyltriethoxysilane, methyltrichlorosilane, phenyltrichlorosilane, trimethylsilyl isocyanate, vinylsilyl triisocyanate and phenylsilyl triisocyanate, most preferably methyltrimethoxysilane, ethyltrimethoxysilane, vinyltriethoxysilane and phenyltrichlorosilane. These compounds may be used alone or in combination thereof. However, there is a possibility that distortion may be produced upon formation of a polysiloxane film due to the presence of an organic group in a polysiloxane film and there may arise a problem on the mechanical strength. Accordingly, an organosilane compound should be added at a small amount. Alkoxide, halide, hydroxide, nitride or carbonate of the other metal may also be added as a part of a silane compound represented by the general formula (I) upon formation of a polysiloxane film.

The inorganic filler of the present invention thus obtained has an average particle size of 0.01~5 μm and the surface thereof is covered with polysiloxane. An average particle size and particle size distribution of an inorganic filler having the surface covered with polysiloxane can be confirmed by a laser diffraction particle size measuring machine. As the result, it was found that an average particle size and particle size distribution of an inorganic filler are the same as those measured when dispersed in an aqueous medium, and, therefore, it was recognized that an inorganic filler is in the form of a uniformily dispersed powder. On the other hand, in an an inorganic particle without polysiloxane film, an average particle size was shifted to the larger side and the polydisperse particle size distribution due to the presence of an aggregate was shown. These dispersion states can be confirmed also by observation with an electron microscope. Although a surface area of an inorganic filler can be measured using BET method, it may be determined by utilizing a specific surface area obtained upon measuring the fine pore distribution. From these measurements, although a specific surface area of an inorganic filler is increased by formation of a polysiloxane film, the fine pore distribution is not observed. In light of these matters, it is believed that the fine pore is not observed since a polysiloxane film formed on the surface of an inorganic fine particle is thin, although porous. It is believed that the fluidity and the dispersibility of the powder are better in spite of a number of hydroxyl groups on the film surface because the irregularity is formed on the film surface and contact between fine particles is a point contact. In light of the above matters, although the thickness of a polysiloxane film is influenced by an amount of a silane compound to be added, it is preferably not greater than 500 nm, more preferably not greater than 100 nm. In addition, it was observed that, when this inorganic filler is used in a dental composition, a resin component is penetrated into the irregular parts of the surface of a polysiloxane film and, the mechanical property is enhanced by the fitting effect. Also, it was observed that the polishability is simultaneously enhanced. However, a large amount of an inorganic filler of this could not be filled in a resin component due to the effect of a number of hydroxyl groups on the polysiloxane film.

In general, a low-filling composite material is used separately from a high-filling composite material in the clinical practice. Although the low-filling composite material has the better fluidity in the form of a paste since only a small amount of a filler is contained, it has the poor operability such as of disintegration of the shaped form. However, when this inorganic filer is filled at a small amount, unexpected effects are manifested such as retained shape of and no adhering to an instrument of a paste.

In addition, this inorganic filler can be filled at a large amount by further treating a polysiloxane film with an organosilane compound represented by the general formula (II):

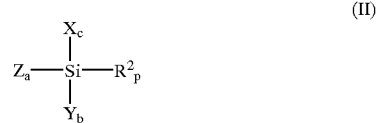

(II)

wherein Z is $R^1O$— or OCN—, X is halogen, Y is —OH, $R^1$ is an organic group having a carbon number of 8 or less, $R^2$ is an organic group, p is an integer of 1~ to 3, and a, b and c are an integer of 0 to 3, provided that a+b+c+p=4, and thus, it has become possible to satisfy the various properties required as a dental composition.

Examples of an organosilane compound represented+by the general formula (II) include methyltrimethoxysilane, ethyltri methoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloxypropyl-trimethoxysilane, γ-glycidoxypropyltrimethoxysilane, γ-mercaptopropyltrimethoxysilane, γ-aminopropyltriethoxysilane, 3-aminopropyltriethoxysilane, methyltrichlorosilane, phenyltrichlorosilane, trimethylsilyl isocyanate, vinylsilyl triisocyanate and phenylsilyl triisocyanate.

Among these organosilane compounds, vinyltrimethoxysilane, vinyl-triethoxysilane, vinyltrichlorosilane, vinyl(β-methoxyethoxy)silane, γ-methacryloxypropyltrimethoxysilane, γ-glycidoxypropyltrimethoxysilane, γ-mercaptopropyltrimethoxysilane and γ-aminopropyltrimethoxysilane which are the known compound as a silane coupling agent in the dental field are effective, and γ-methacryloxypropyltrimethoxysilane is more preferable. These organosilane compounds may be used alone or in combination thereof.

The compatibility with a resin component is enhanced by these organosilane compounds because an organosilane compound was effectively and uniformly treated by a reaction with a number of hydroxyl groups on a polysiloxane film.

The above inorganic filler of the present invention can be used as a characteristic filler in a matrix containing an organic polymer material as a main component. Particularly preferably, it can be used in a dental composition such as a dental restorative material to impart thereto the excellent properties.

An another aspect of the present invention is a dental composition containing the above inorganic filler of the present invention. Particularly, it is a dental composition comprising (a) the inorganic filler of the present invention, (b) a polymerizable monomer, and (c) a polymerization initiator.

In the composition, not only the inorganic filler of the present invention can be uniformly dispersed in the non-aggregated state in a matrix containing an organic polymer material as a main component due to the presence of a polysiloxane film on the surface thereof, but also it has the characteristic that a cured composition manifests the excellent physical property due to the high compatibility with an organic matrix. In addition, a cured dental composition containing an inorganic filler of the present invention as a filler has the excellent wear resistance in spite of such a fine filler, in addition to the excellent glossiness after polishing originally derived from fineness of a filler. It is believed that this excellent wear resistance is imparted by the fact that a filler interacts with a matrix with the strong compatibility, due to the action of a polysiloxane film on the surface of an inorganic filler and an organosilane compound which is added upon dispersion in a matrix.

A polymerizable monomer which can be used in a dental composition together with an inorganic filler of the present invention, can be used by selecting from the known monofunctional and multifunctional polymerizable monomers which are generally used as a dental composition.

Representative examples which are generally used suitably are polymerizable monomers having an acryloyl group and/or a methacryloyl group. In the present invention, (meth)acrylate or (meth)acryloyl represented inclusively both acryloyl group-containing polymerizable monomers and methacryloyl group-containing polymerizable monomers.

Embodiments thereof are as follows:

As polymerizable monomers having no acidic group, monofunctional monomer: (meth)acrylic acid esters such as methyl(meth)acrylate, ethyl (meth)acrylate, butyl(meth)acrylate, hexyl(meth)acrylate, tetrahydrofurfuryl(meth)acrylate, 2-hydroxyethyl(meth)acrylate, grycidyl(meth)acrylate, lauryl(meth)acrylate, cyclohexyl(meth)acrylate, allyl(meth)acrylate, 2-ethoxyethyl(meth)acrylate, methoxy polyethylene glycol(meth)acrylate, glycerol(meth)acrylate, isobonyl(meth)acrylate and the like, silane compounds such as γ-(meth)acryloyloxypropyltrimethoxysilane, γ-(meth)acryloyloxypropyltriethoxysilane and the like, nitrogen-containing compounds such as 2-(N,N-dimethylamino)ethyl (meth)acrylate, N-methylol(meth)acrylamide, diacetone (meth)acrylamide and the like, aromatic bifunctional monomer:
2,2-bis(4-(meth)acryloyloxyphenyl)propane,
2,2-bis(4-(3-(meth)acryloyloxy-2-hydroxypropoxy)phenyl)propane,
2,2-bis(4-(meth)acryloyloxyethoxyphenyl)propane,
2,2-bis(4-(meth)acryloyloxydiethoxyphenyl)propane,
2,2-bis(4-(meth)acryloyloxytetraethoxyphenyl)propane,
2,2-bis(4-(meth)acryloyloxypentathoxyphenyl)propane,
2,2-bis(4-(meth)acryloyloxydipropoxyphenyl)propane,
2,2-bis(4-(meth)acryloyloxyethoxyphenyt)-2-(4-(meth)acryloyloxydiethoxyphenyl)propane,
2-(4-(meth)acryloyloxydiethoxyphenyl)-2-(4-(meth)acryloyloxytriethoxyphenyl)propane,
2-(4-(meth)acryloyloxydipropoxyphenyl)-2-(4-(meth)acryloyloxytriethoxyphenyl)propane,
2,2-bis(4-(meth)acryloyloxypropoxyphenyl)propane,
2,2-bis(4-(meth)acryloyloxyisopropoxyphenyl)propane and the like, aliphatic bifunctional monomer:
2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol(meth)acrylate, 1,6-hexanediol (meth)acrylate, glycerin di(meth)acrylate and the like, trifunctional monomer:
trimethylolpropane tri(meth)acrylate, treimethylolethane tri(meth)acrylate, trimethylolmethane tri(meth)acrylate, pentaerythritol tri(meth)acrulate and the like, tetrafunctional monomer:
pentaerythritol tetra(meth)acrylate, ditrimethylolpropane tetra(meth)acrylate and the like.

In addition, embodiments of an urethane system polymerizable monomer are di(meth)acrylates having a bifunctional or trifunctional or more-functional urethane linkage which are derived from an adduct of a polymerizable monomer having a hydroxy group such as 2-hydroxyethyl(meth)acrylate, 2-hydroxypropyl(meth)acrylate and 3-chloro-2-hydroxypropyl(meth)acrylate and a diisocyanate compound such as methylcyclohexane diisocyanate, methylene bis(4-cyclohexyl isocyanate), isophorone diisocyanate, diisocyanate methylbenzene and, 4,4-diphenylmethane diisocyanate.

In addition to the aforementioned (meth)acrylate system polymerizable monomers, other polymerizable monomers, for example, a monomer, an oligomer or a polymer having at least one polymerizable group in the molecule may be used depending upon the purpose of a dental composition without any limitation. In addition, there is no problem that the polymerizable monomers have a substituent such as an acidic group, a fluoro group and the like.

In the present invention, a polymerizable monomer includes not only a single component but also a mixture of a plurality of polymerizable monomers.

In addition, when a polymerizable monomer has the extremely high viscosity at room temperature or when a polymerizable monomer is a solid at room temperature, it is preferably used as a mixture of polymerizable monomers by combining with a polymerizable monomer having a low viscosity. This combination may comprise not only two kinds but also three kinds or more.

In addition, since a polymer comprising only monofunctional polymerizable monomers has no cross-linking structure, it generally has a tendency to be inferior in the mechanical strength of a polymer.

For that reason, when a polymnerizable monomer is used, it is preferable that it is used with a polyfunctional polymerizable monomer. The most preferable combination of polymerizable monomers is a manner of combining an aromatic compound of a bifunctional polymerizable monomer as a main component with an aliphatic compound of a bifunctional polymerizable monomer.

More particularly, there is a combination of 2,2-bis(4-(3-methacryloyloxy-2-hydroxypropoxy)phenyl)propane (Bis-GMA) and triethylene glycol dimethacrylate (TEGDMA).

When a teeth substance and a nonprecious metal adhering property is imparted to a dental composition containing an inorganic filler of the present invention, it is effective to use a polymerizable monomer containing an acid group such as a phosphoric acid group, a carboxylic acid group, a sulfonic acid group or the like in the molecule as a part or the whole of a polymerizable monomer.

In addition, in order to enhance a precious metal adhering property, it is also effective to the present invention to use those polymerizable monomers containing a sulfur atom in the molecule. Embodiments of these polymerizable monomers having the adhering ability are as follows:

Carboxylic acid group-containing polymerizable monomer:

(meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 2-(meth)acryroyloxybenzoic acid, β-(meth)acryroyloxyethyl hydrogen succinate, β-(meth)acryroyloxyethyl hydrogen maleate, 11-(meth)acryloyloxy-1,1-undecanedicarboxylic acid, p-vinylbenzoic acid and the like, phosphate group-containing monomer:

2-(meth)acryloyloxyethyl dihydrogen phosphate, 3-(meth)acryloyloxypropyl dihydrogen phosphate, 10-(meth)acrylovloxydecyl dihydrogen phosphate, bis(2-(meth)acryloyloxyethyl)hydrogen phosphate, 2-(meth)acryloyloxyphenyl hydrogen phosphate and the like, Sulfonic group-containing monomer:

2-(meth)acrylamide-2-methylpropanesulfonic acid,
4-(meth)acryloyloxybenzenesulfonic acid,
3-(meth)acryloyloxypropanesulfonic acid and the like, Sulfur atom-containing monomer:

(meth)acrylate having a triazinethiol group, (meth)acrylate having a mercapto group, (meth)acrylate having a polysulfide group, (meth)acrylate having a thiophosphate group, (meth)acrylate having a disulfide group, (meth)acrylate having a mercaptodithiazole group, (meth)acrylate having a thiouracil group, (meth)acrylate having a thuirane group and the like.

These polymerizable monomers are used alone or as a mixture of two or more without any problem.

A polymerization initiator which can be used with an, inorganic filler of the present invention in a dental composition is not particularly limited and the known radical generator can be used without any limitation.

Polymerization initiators are generally classified into initiators which initiate polymerization by mixing prior to use (chemical polymerization initiator), initiators which initiate polymerization by heating or warming (thermal polymerization initiator, and initiators which initiate polymerization by light irradiation (photoinitiators).

As a chemical polymerizable initiator, there are polymerizable initiator systems of a redox type comprising an organic peroxide/an amine compound or an organic peroxide/an amine compound/a sulfinic acid salt, or an organic peroxide/an amine compound/a borate compound, and organometal type initiator system which initiates polymerization by a reaction with oxygen or water. Further, sulfinic acid salts and borate compounds can also initiate polymerization by a reaction with a polymerizable monomer having an acidic group.

Embodiments of the aforementioned organic peroxide are benzoylperoxide, parachlorobenzoylperoxide, 2,4-dichlorobenzoyl peroxide, 2,5-dihydroperoxy-2,5-dimethylhexane, methyl ethyl ketone peroxide, tertiary-butyl peroxide benzoate and the like.

As the aforementioned amine compound, a secondary or tertiary amine in which an amine group is bound to an aryl group is preferable and embodiments thereof are p-N,N-dimethyltoluidine, N,N-dimethylaniline, N-β-hydroxyethylamine, N,N-di(β-hydroxyethyl)aniline, p-N,N-di(β-hydroxyethyl)toluidine, N-methylaniline, p-N-methyltoluidine and the like.

Embodiments of the aforementioned sulfinic acid salt are sodium benzenesulfinate, lithium benzenesulfinate, sodium p-toluenesulfinate and the like.

As the aforementioned borate compound, there are trialkylphenylboron, and sodium salt, lithium salt, potassium salt, magnesium salt, tetrabutyl ammonium salt, tetramethyl ammonium salt of trialkyl (p-fluorophenyl)boron (wherein alkyl group is n-butyl group, n-octyl group, n-dodecyl group or the like). In addition, as the aforementioned organometal type polymerizable initiator, there. are organic boron compounds such as triphenylborane, tributylborane, partial oxide of tributylborane and the like. In addition, as a thermal polymerization initiator by heating or warming, azo compounds such as azobisisobutyronitrile, methyl azobisisobutyrate, azobiscyano valeric acid and the like are suitably used.

On the other hand, as a photoinitiator, there are a photoinitiator comprising a photosensitizer, a photosensitizer/a photopolymerization promotor and like.

Embodiments of the aforementioned photosensitizer are α-diketones such as benzil, camphorquinone, α-naphtil, acetonaphtone, p,p'-dimethoxybenzil, pentandione, 1,2-phenanthrenquinone, 1,4-phenanthrenquinone, 3,4-phenanthrenquinone, 9,10-phenanthrenquinone, naphthoquinone and the like benzoin alkyl ethers such as benzoin, benzoin methyl ether, benzoin ethyl ether and the like, thioxanthones such as thioxanthone, 2-chlorothioxanthone, 2-methylthioxanthone, 2-hydroxythioxanthone, 2,4-diethylthioxanthone, 2,4-diisopropylthioxanthone and the like, benzophenones such as benzophenone, p-chlorobenzophenone, p-methoxybenzophenone and the like, acylphosphineoxides such as 2,4,6-trimethylbenzoyl diphenyiphosphineoxide, bis(2,6-dimethoxybenzoyl)-2,4,4-trimethylpentylphosphineoxide and the like, α-aminoacetophenones such as 2-benzyldimethylamino-1-(4-morpholinophenyl)butanone-1,2-benzyl-diethylamino-1-(4-morpholinophenyl)propanone-1 and the like, ketals such as benzyldimethylketal, benzyldiethylketal, benzyl(2-methoxyethylketal) and the like, titanocenes such as bis(cyclopentadienyl)-bis[2,6-difluoro-3-(1-pyrolyl)phenyl]titanium, bis(cyclopentadienyl)-bis(pentanefluorophenyl)titanium, bis(cyclopentadienyl)-bis(2,3,5,6-tetrafluoro-4-disiloxyphenyl)-titanium and the like.

Embodiments of the aforementioned photopolymerization promoters are tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 2-dimethylaminopyridine, N,N-dimethyl-a-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, 2,2'-(n-butylimino)diethanol and the like, secondary amines such as N-phenylglycine and the like, barbituric acid such as 5-butylbarbituric acid, 1-benzyl-5-phenylbarbituric acid and the like, tin compounds such as dibutyltin diacetate, dibutyltin dilaurate, dioctyltin dilaurate, dioctyltin diperacetate, dioctyltin bis(mercaptoacetic acid isooctyl ester) salt, tetramethyl-1,3-diacetoxydistannoxane and the like, aldehyde compounds such as laurylaldehyde, terephthalaldehyde and the like, sulfur-containing compounds such as dodecylmercaptan, 2-mercaptobenzoxazole, 1-decanethiol, thiosalicylic acid and the like.

In addition, for improving the photopolymerization promoting ability, the additions of oxycarboxylic acids such as citric acid, maleic acid, tartaric acid, glycolic acid, gluconic acid, α-oxyisobutyric acid, 2-hydroxyproploic acid, 3-hydroxybutanoic acid 4-hydroxybutanoic acid, dimethylolpropioic acid and the like is effective besides the additions of the aforementioned photopolymerization promoters.

Those polymerization initiators may be used alone or as a mixture of two or more of them. In addition, they can be used in a combination irrespective of a polymerization form and a kind of a polymerization initiator.

An amount of a polymerization initiator to be added may be appropriately selected depending upon the use. In general, the amount may be selected from a range of 0.1~10 parts by weight relative to a polymerizable monomer.

Among the aforementioned polymerization initiators, it is preferable to use a photopolymerization initiator which generates a radical by light irradiation and such the initiator is most suitably used in that a dental composition can be polymerized in the state where an air is mixed therein at a small amount. In addition, among photopolymerization initiators, a combination of α-diketone and tertiary amine is preferable and a combination of camphorquinone with an aromatic amine having an amino group directly bound to a benzene ring such as ethyl p-N,N-dimethylaminobenzoate and the like or an aliphatic amine having a double bond in the molecule such as N,N-dimethylaminoethyl methacrylate is most preferable.

In addition, sensitizing pigments such as coumarin, cyanine, thiazine and the like, a light acid generator which produces Bronsted acid or Lewis acid by light irradiator such as a s-triazine derivative substituted which a halomethyl group, diphenyl iodonium salt compound and the like, quaternary ammonium halides, transition metal compound are also suitably used depending upon the use.

Another filler which can be used in a dental composition in combination with inorganic fillers of the present invention is not particularly limited, but the known filler, for example, an inorganic filler and/or an organic filler and/or an organic-inorganic compound filler, can be used without any limitation. A shape of such a filler is not particularly limited, but particle shapes such as of sphere, needle, plate, crushed and flake may be taken. Also, a kind of the filler is not particularly limited.

Examples of an inorganic filler include quartz, amorphous silica, aluminium silicate, aluminium oxide, titanium oxide, zirconium oxide, various glasses (including a glass prepared by a melting process, a synthetic glass prepared by a sol-gel process, a glass produced by a vapor phase process), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite and the like. Among them, preferred are an aluminosilicate glass, a borosilicate glass, an aluminoborate glass, a boroaluminosilicate glass and the like, which contain heavy metals such as sodium, strontium, barium and lanthanum and/or fluoride. An average particle size of the inorganic filler is not particularly limited, but it is preferably in a range of 0~10 μm, and more preferably in a range of 0~5 μm.

In addition, ultrafine particle inorganic fillers such as Aerosil produced by a vapor phase process or a particle of silica-zirconia oxide produced from a solution by a sol-gel process can be used. In addition, an aggregated inorganic filler in which such the ultrafine particle is aggregated may be used without any problem.

In addition, an organic filler can be prepared by polymerizing a monomer having a polymerizable group, and a kind thereof is not particularly limited. Examples of an organic filler include fillers prepared by (co)polymerizing a polymerizable monomer, alone or in combination, such as unsaturated aromatic compounds such as styrene, α-methylstyrene, halogenated styrene and divinylbenzene; unsaturated esters such as vinyl acetate and vinyl propionate; unsaturated nitrites such as acrylonitrile; and butadiene and isoprene. Particularly preferred is a filler prepared by polymerizing the above polymerizable monomer which is known in the dental field. A process for producing an organic filler is also not particularly limited, but processes such as emulsion polymerization, suspension polymerization and dispersion polymerization, or a process of grinding a preformed polymer bulk can be employed.

Alternatively, an organic-inorganic compound filler containing an inorganic particle in an organic polymer can be used. An inorganic particle to be contained in an organic polymer is not particularly limited, but the known inorganic particle, for example, the aforementioned inorganic filler can be contained. A process for producing an organic-inorganic compound filler is also not particularly limited, but any process can be adopted. Examples of such the process include a process for micro-encapsulating an inorganic particle with an organic material or grafting the surface of an inorganic particle with an organic material, a process for radical-polymerizing a polymerizable functional group or a polymerizable initiation group on the surface of an inorganic particle after introducing it to the surface, a process for grinding a polymer bulk containing inorganic particles which have been produced in advance, and the like.

An average particle size of an organic or organic-inorganic composite compound filler is preferably in a range of 1~100 μm, more preferably in a range of 3~50 μm, and most preferably within a range of 5~30 μm. These inorganic, organic and organic-inorganic compound fillers can be used alone or in combination thereof.

Fillers such as inorganic, organic and organic-inorganic compound fillers can be used for a dental composition, after the surface of a particle thereof is treated with, for example, surfactants, fatty acids, organic acids, inorganic acids, silane coupling agents, titanate coupling agents, polysiloxane or the like. These surface treating processes are preferable in that these can enhance the wettability between a resin component and the filler surface and can impart various excellent properties to a dental composition, and these can be arbitrarily selected depending upon the required properties. Moreover, in order to multi-functionalize these fillers, surface treatment with special surface treating agents and/or by a special process of surface treatment can be conducted without any limitation.

A proportion of such the filler in a dental composition may be optionally selected depending upon material property required for a dental composition.

An filling amount of low-viscous materials such as sealants, bonding materials, primers, tooth surface treating agents, opaciiying agents and cements generally used in the dental field should be set at a relatively small level since higher fluidity required as material property is required for these materials. Therefore, the amount is preferably in a range of 5.0~80.0 parts by weight, more preferably in a range of 30.0~70.0 parts by weight relative to the whole component of a dental composition.

In addition, an filling amount of high-viscous materials such as a composite resin and a beneer crown resin should be set at a relatively high level since, as the required material property, such the shapability is required that does not cause deformation after shape adjustment. Accordingly, the amount is preferably in a range of 50.0~98.0 parts by weight, more preferably in a range of 75.0~98.0 parts by weight relative to the whole component of a dental composition.

In addition, if needed, components such as ultraviolet absorbing agents such as 2-hydroxy-4-methylbenzophenone, polymerization inhibitors such as hydroquinone, hydroquinone monomethyl ether and 2,5-di (tertiary-butyl)-4-methylphenol, anti-discoloring agents, antimicrobial agents, and other conventional known additives may be optionally added to a dental composition.

A packing type of the dental composition of the present invention is not particularly limited, but it may be any one of one-package type, two-package type and the like depending upon a kind of a polymerization initiator or a purpose of use, and it may be appropriately selected depending upon the application.

The second aspect of the present invention is characterized specifically by the three-layered structure in which the surface of the present multi-functional filler is covered with a cement reactive phase, and the outside is fuirther covered with polysiloxane.

It is preferred that an inorganic fine particle constituting the core of the multi-functional filler comprises an acid reactive element because a cement reactive phase is formed on the surface of the inorganic fine particle. More preferred is a metal element belonging to Group I, II and III of the Periodic Table, and particularly preferred are sodium, potassium, calcium, strontium, lanthanum, aluminium and the like. In addition, as examples of such an inorganic particle, any inorganic particle comprising an acid reactive element can be used without limitation. Moreover, any inorganic particle of any nature, water soluble or insoluble, particle size, shape and the like, can be used without any limitation. Specifically, examples of these inorganic particles are aluminium silicate, aluminium oxide, various kinds of glasses (including a glass made by a melting process, a glass formed by a vapor phase process, a synthesized glass by a sol-gel process, etc.), strontium fluoride, calcium carbonate, kaolin, mica, aluminium sulfate, calcium sulfate, barium sulfate, calcium phosphate, calcium hydroxide, strontium hydroxide, zeolite, hydroxyapatite, aluminium nitride and the like. Glasses are particularly preferred. Glasses are preferred since they can impart the functions required as a dental composition, for example, they have the lower hardness than that of silica compounds and the excellent light transmission, and they can comprise floine fluoride and elements which block an X-ray.

Most preferred are an aluminosilicate glass, a borosilicate glass, an aluminoborate glass and a boroaluminosilicate glass, which comprise a heavy metal, such as strontium, barium, lanthanum and the like and fluoride. In addition, it is preferred that an average particle size of the inorganic fine particle used in the present invention is in a range of 0.01~50 μm, more preferably 0.01~20 μm and, most preferably 0.01~10 μm.

It is required that the core inorganic fine particle contains fluoride so that the multi-functional filler of the present invention has the sustained fluoride releasability and, in this case, as an inorganic fine particle, for example, sodium fluoride, strontium fluoride, lanthanum fluoride, ytterbium fluoride, yttrium fluoride, and calcium-containing fluoroaluminosilicate glasses are used. In addition, it is required that the core inorganic fine particle comprises a heavy metal so that the multi-functional filler of the present invention has the radiopacity and, in this case, as an inorganic fine particle, for example, strontium fluoride, lanthanum fluoride, ytterbium fluoride, yttrium fluoride, lanthanum-containing fluoroaluminosilicate glasses, and strontium-containing fluoroaluminosilicate glasses are used.

As the inorganic fine particle used in the present invention, a commercially available raw material inorganic particle, which is generally used as a filler, may be used without any processing. In addition, if a desired particle size is required, it can be obtained by grinding. Grinding does not require a specific process, and it may be performed by adopting a process normally used in the art, whether a wet or dry process without any limitation. ExaImples thereof are a high-speed rotation mill such as a hammer mill and a turbo mill, a container-driven medium mill such as a ball mill and an oscillating mill, a grinding medium agitating mill such as a sand grinder and an attritor, and a jet mill and the like, and they may be appropriately selected depending upon the desired average particle size of the inorganic fine particle. Additionally, it is preferred that an average particle size of the inorganic fine particle is in a range of 0.01 μm 50 μm, more preferably 0.01~20 μm, most preferably 0.01~10 μm. An average particle size of the inorganic fine particle greatly affects the subsequent step of forming a polysiloxane film. The polysiloxane film forming step may be performed both by a wet process and by a dry process, the wet process can form a more uniform polysiloxane film. It is difficult to form a uniform polysiloxane film by using a dry process since a smaller particle size tends to form an aggregate. On the other hand, when the particle size becomes larger, precipitation of the inorganic fine particle is likely to occur in the wet process. Therefore, in the case of a larger particle size, a dry process is more adequate.

The multi-functional filler of the present invention has a relatively small average particle size, and has the three-layered structure in which a cement reactive phase is formed on the surface of the core inorganic fine particle, and the outside thereof is further covered with a uniform polysiloxane film and, therefore, a wet process which can form a uniform polysiloxane film is more proper. Thus, in the case where the wet-ground or wet-dispersed inorganic fine particle is dispersed in the preceding step prior to the step of forming the polysiloxane film, the procedures proceed smoothly, and such the process has advantages not only in forming a uniform polysiloxane film but also in the workability, the cost and the like. Here, a step of forming a uniform polysiloxane film after a wet-grinding step is described.

A wet-grinding can be performed by a process which is generally used in the art. For example, a raw material inorganic particle may be fine-ground using a container-driven medium mill such as a ball mill, an oscillation mill and the like, a grinding medium agitating mill, such as attritor, a sand grinder, an annealer mill, a tower mill and the like. As an aqueous medium, water alone or a medium in which all or a part of water is substituted with an aqueous solvent such as alcohols, ketones such as acetone and the like or ethers and the like may be used as necessary. When these aqueous solvents are used, the aggregating force of a solidified material after drying is weakened and disintegration can be easily performed.

The multi-function filler of the present invention has a film formed with polysiloxane on the outermost layer thereof.

The polysiloxane film may be formed, for example, by the following process.

The polysiloxane film may be formed by mixing a silane compound represented by the general formula (I):

(I)

wherein Z is RO— or OCN—, X is halogen, Y is —OH, R is an organic group having a carbon number of 8 or less, and n, m and L are an integer of 0 to 4, provided that n+m+L=4, in an aqueous dispersion containing an inorganic fine particle disintegrated to a particle having the desired average particle size by wet-grinding, then, the mixture is hydrolyzed or partially hydrolyzed in the system, which is then condensed via a silanol compound.

Although, in the case of the above process for forming a polysiloxane film, hydrolysis and condensation of a silane compound and formation of a polysiloxane film on the surface of an inorganic fine particle are simultaneously proceeded in the same system, another process for forming a polysiloxane film in which hydrolysis and condensation of a silane compound are conducted to produce a low-condensed silane compound (oligomer) in the other system and then the low-condensed silane compound is mixed into the aqueous dispersion of an inorganic fine particle obtained by a wet-grinding or a wet-dispersing step can more effectively form a polysiloxane film on the surface of an inorganic particle. More preferable is a process for forming a polysiloxane film by mixing a commercially available low-condensed silane compound (oligomer) without passing through a low-condensed compound production step. The reason why this process is preferable can be considered as follows. When a silane compound monomer is used, a polysiloxane film can not be uniformly formed on the surface of an inorganic fine particle because condensation is three-dimensionally caused and self-condensation is dominantly proceeded because of the presence of a large amount of water during a polysiloxane film forming step.

On the other hand, when a low-condensed silane compound (oligomer) is used, it can be considered that a polysiloxane film may be uniformly formed on the surface of an inorganic fine particle in a unit having a polysiloxane main chain of a certain length. The structure of such the low-condensed silane compound (oligomer) is not particularly limited, but the linear chain structure is more preferable than the three dimensional structure, and a degree of polymerization thereof is preferably in a range of 2~20, more preferably in a range of 2~6, since the condensation reactivity is lowered and formation of a polysiloxane film on the surface of an inorganic particle is deteriorated in the higher degree of polymerization. The above degree of polymerization corresponds to a molecular weight range of 500~600. In the case of preparation of a low-condensed silane compound (oligomer) having the straight chain structure in the other system, it is necessary to conduct preparation with a small amount of water such that hydrolysis and condensation of a silane compound monomer are partially proceeded, and such the preparation can be conducted by using acids, alkalis or other catalysts used in a sol-gel process.

Thereby, the system becomes the state where an inorganic fine particle is fine-dispersed, without any association, in an aqueous medium in which a condensed silane compound, that is, polysiloxane is dispersed.

The above hydrolysis or partial hydrolysis of a silane compound in an aqueous dispersion is conducted at a temperature in a range of room temperature to 100 C, preferably in a range of room temperature to 50 C for a few minutes to a few ten hours, preferably for 30 minutes to 4 hours, with stirring at a relatively low rotating speed. Stirring does not require any special procedure, and the equipment normally used in the art can be adopted. For example, a stirrer which can stir the slurry-like material such as a universal mixer and a planetary mixer may be used to stir. There is no problem when a stirring temperature is not greater than a boiling point of an aqueous medium.

An amount of a silane compound to be added depends upon a particle size of an inorganic fine particle and is in a range of 0.1~10% by weight, preferably in a range of 0.1~4% by weight in terms of $SiO_2$ relative to an inorganic fine particle. When the amount is below 0.1% by weight, the effect of formation of a polysiloxane film is not manifested and particles can not be disintegrated to a primary particle and remain aggregated and, on the other hand, when the amount exceeds 10% by weight, the solidified material after drying becomes too hard to disintegrate.

Then, the system in such the gelated state is dried and an aqueous medium is removed to solidify. A drying step consists of two stages of aging and sintering, and the former stage is aimed at growing the gel structure and removing an aqueous medium, and the latter stage is aimed at reinforcing the gel structure. The former stage should be conducted by allowing to stand so as not to impart distortion to the gel structure and so as to remove an aqueous medium and therefore, it is preferably conducted in a equipment such as a box-type heat dryer. An aging temperature is in a range of room temperature to 100 C, preferably in a range of 40 to 80 C. When the temperature is lower than the above range, then removal of an aqueous medium becomes insufficient and, on the other hand, when the temperature exceeds the above range, then an aqueous medium is rapidly evaporated and, thereby, there is a possibility that an imperfection is produced in the gel structure or the gel structure is peeled from the surface of an inorganic fine particle. An aging time may be any time as long as it is sufficient for removing an aqueous medium since it varies depending upon the ability of a dryer and the like.

On the other hand, the sintering step consists of temperature rising and holding, and the former is preferably conducted by gradually rising a temperature to the desired temperature for a longer period of time, and there is a possibility that distortion may be produced in the gel structure by rapid temperature rising since the thermal conductivity of the gel dispersion is low. The latter is a sintering at a constant temperature A sintering temperature is in a range of 100 to 350 C, more preferably of 100 to 200 C. The temperature should be appropriately selected so as not to influence on a raw material of an inorganic fine particle and not to make the porous gel structure non-porous.

In this way, an aqueous medium is removed from the gel by drying to obtain a constricted solidified material. Although the solidified material is in the state of aggregated inorganic fine particles, it is not a mere aggregate of inorganic. fine particles, and a polysiloxane film formed by condensation intervenes on the boundary surface of individual fine particle. Accordingly, as the next step, when the solidified material is disintegrated to a size corresponding to that of an inorganic fine particle before treating with polysiloxane, then the separated inorganic fine particle having the surface covered with a polysiloxane, that is, an inorganic filler covered by polysiloxane can be obtained. As used herein, the term "disintegrated to a size corresponding to that of an inorganic fine particle before treating with polysiloxane" means disintegration to an inorganic fine particle, and the difference from the original inorganic fine particle is that the separated inorganic fine particle is covered with polysiloxane. Provided that, the secondary aggregate may be contained to a non-problematic degree. Disintegration of a solidified material may be easily conducted by applying it a shearing force or an impact force, and a disintegrating process may be conducted by using, for example, a Henschel mixer, a cross rotary mixer, a super mixer or the like.

The silane compound represented by the general formula (I) includes, for example, tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide(silicon oxide hydrate), silane tetraisocyanate and silane ethoxytriisocyanate, preferably tetramethoxysilane and tetraethoxysilane.

A low-condensed compound of the silane compound represented by the general formula (I) is more preferable. An example thereof is a low-condensed silane compound which is prepared by partially hydrolyzing and then condensing tetramethoxysilane and tetraethoxysilane. These compounds may be used alone or in combination thereof.

An organosilane compound also may be added as a part of the silane compound represented by the general formula (I) upon formation of a polysiloxane film. Specifically, the organosilane compound include, for example, methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri($\beta$-methoxyethoxy)silane, $\gamma$-methacryloxypropyltrimethoxysilane, $\gamma$-glycidoxypropylmethoxysilane, $\gamma$-mercaptopropyltrimethoxysilane, $\gamma$-aminopropyltriethoxysilane, 3-aminopropyltriethoxysilane, methyltrichlorosilane, phenyltrichlorosilane, trimethylsilyl isocyanate, vinylsilyl triisocyanate and phenylsilyl triisocyanate, most preferably methyltrimethoxysilane, ethyltrimethoxysilane, vinyltriethoxysilane and phenytrichlorosilane. These compounds may be used alone or in combination thereof. However, there is a possibility that distortion may be produced upon formation of a polysiloxane film due to the presence of an organic group in a polysiloxane film and there may arise a problem on the mechanical strength. Accordingly, an organosilane compound should be added at a small amount. Alkoxide, halide, hydroxide, nitride or carbonate of the other metal may also be added as a part of a silane compound represented by the general formula (I) upon formation of a polysiloxane film.

An average particle size and particle size distribution of the polysiloxane-covered inorganic particle thus obtained can be confirmed by a laser diffraction particle size measuring machine. As the result, it is recognized that the inorganic particle was powdered in the uniform dispersion state because it had the same average particle size and particle size distribution with monodipersion as those measured in the state where the inorganic particle is dispersed uniformly in an aqueous medium. This dispersed state can be observed also by an electron microscope.

The thickness of a polysiloxane film is influenced by an amount of a silane compound and that of a siloxane compound to be added and is 500 $\mu$m or less, more preferably 100 $\mu$m or less.

The multi-functional filler of the present invention is an inorganic filler in which a cement reactive phase is formed on the surface, and the outside thereof is further covered with polysiloxane, and can be produced, for example, by reacting an acidic polymer with the polysiloxane-coated inorganic fine particle obtained by the above process.

The cement reaction can be carried out by using any equipment, as far as it is a dry fluid agitator such as a Henschel mixer, a super mixer, a high-speed mixer and the like. The reaction of the acidic polymer with the polysiloxane-coated inorganic fine, particle containing an acid reactive element can be carried out merely by contacting an acidic polymer solution with the inorganic fine particle by impregnation and the like. For example, the polysiloxane-covered inorganic particle is dry-fluidized, the acidic polymer solution may be dispersed from the above side while fluidizing the inorganic particle, and stirred sufficiently. At this point, a process of dispersing the acidic polymer solution is not particularly limited, but dropping or spraying is more preferable, which can attain uniform dispersion. In addition, it is preferred that the reaction is carried out at around room temperature and, when a temperature is elevated, the reaction of the acid reactive element and the acidic polymer becomes faster, resulting in no formation of a uniform cement reactive phase.

After heat treatment, disintegration of the thermal treated material can be done easily by applying a shearing force or an impact force to it, the disintegration process may be carried out with the equipment used in the above reaction.

As a solvent used in preparing an acidic polymer solution for the reaction, any solvents in which the acidic polymer dissolves, for example, water, ethanol, acetone and the like can be used without any problem. Among them, particularly preferred is water, which can allow the acidic residue of the acidic polymer to dissociate so that the polymer can react uniformly with the surface of the core inorganic particle. On the other hand, since other solvents cause imperfect reaction of the surface of the core inorganic particle and, consequently, residual unreacted acidic groups exist and, when this multi-functional filler is incorporated into a dental composition, this results in inhibiting polymerization of the polymerizable monomer, deterioration of the material by water-absorption of the cured product, and the like.

A weight-average molecular weight of the polymer dissolving in the acidic polymer solution is in a range of 2000~50000, more preferably in a range of 5000~40000. In the case of an acidic polymer having a weight-average molecular weight of less than 2000, the strength of a cement reactive phase tends to be low and tends to reduce the strength of a material. In the case of an acidic polymer having a weight-average molecular weight of more than 50000, since the viscosity of the acidic polymer solution is increased, it is difficult to diffuse a polysiloxane film (a porous material), and a residual unreacted acidic group remains, which tends to have an adverse effect. In addition, the acidic polymer concentration in the acidic polymer solution is preferably in a range of 3~25 wt %, more preferably in a range of 8~20 wt %. When the acidic polymer concentration is less than 3 wt %, the strength of the above-mentioned cement reactive phase becomes weak and, simultaneously, the fluidity of the polysiloxane-covered inorganic particle is lowered due to the influence of water, so that a uniform cement reactive phase can not be formed. Further, when the acidic polymer concentration exceeds 25 wt %, problems arise that a polysiloxane film (a porous material) becomes difficult to diffuse, and once it is contacted with the core inorganic particle, an acid-base reaction proceeds fast to start curing during the reaction and aggregation occurs. In addition, an amount of the acidic polymer solution to be added to a polysiloxane-covered inorganic particle is in a range of 6~40 wt %, more preferably in a range of 10~30 wt %. When the added amount is converted, the optimized range are 1~7 wt % for an amount of the acidic polymer relative to the polysiloxane-covered inorganic particle, and 10~25 wt % for an amount of water.

This reaction is influenced by a surface area of the core inorganic particle and, when a surface area becomes smaller, an acid-base reaction becomes faster and, when a surface area becomes larger, a reaction becomes slower. That is, the particle size distribution is important and, in the case of an inorganic particle having a monodisperse particle size distribution, to be formed a cement reactive phase uniformly, it is considered that when the acidic polymer has a polydisperse molecular weight distribution, a reaction progresses consecutively and, therefore, a cement reactive phase can be formed effectively and uniformly. In addition, the outermost polysiloxane film has many roles. The film controls a time during an acidic polymer reaches the surface of the polysiloxane film and diffuses through a porous material to reach the surface of a core inorganic particle and, thereby, a uniform cement reactive phase can be formed. In the absence of the polysiloxane film, a reaction begins to cause bridging between particles as soon as an acidic polymer is contacted with the surface of an inorganic particle. This is also prevented by the presence of the film.

Water in a cement reactive phase is vaporized by performing heat treatment after the reaction, the cement reactive phase becomes porous and, therefore, it becomes disadvantageous in the strength, which is reinforced by coverage with this polysiloxane film. In addition, this cement reactive phase is an organic-inorganic compound layer, and has the poor wettability with a silane coupling agent, the surface treatment effect is not manifested. However, by the effect of many OH groups existing on the surface due to the presence of the polysiloxane film, the surface treatment effect is manifested.

The acidic polymer, which can be used to form a cement reactive phase on the surface of an inorganic fine particle by the above process, is a copolymer or a homopolymer of a polyrerizable monomer having an acidic group such as a phosphate residue, a pyrophosphate residue, a thiophosphate residue, a carbonate residue, a sulfonate residue and the like, as an acidic group. As a polymerizable monomer having these acidic groups, there are exemplified acrylic acid, methacryric acid, 2-chloroacryric acid, 3-chloroacryric acid aconitic acid, mesaconic acid, maleic acid, itaconic acid, fumaric acid, glutaconic acid, citraconic acid, 4-(meth) acryloyloxyethoxycarbonylphthalic acid, 4-(meth) acryloyloxyethoxycarbonylphthalic anhydride, 5-(meth) acryloylaminopentylcarboxylic acid, 11-(meth)acryloyloxy-1,1-undecanedicarboxylic acid, 2-(meth) acryloyloxyethyldihydrogenphosphate, 10-(meth) acryloyloxydecyldihydrogenphosphate, 20-(meth) acryloyloxyeicosyldihydrogenphosphate, 1,3-di(meth) acryloyloxypropyl-2-dihydrogenphosphate, 15. 2-(meth) acryloyloxyethylphenylphosphate, 2-(meth) acryloyloxyethyl 2'-bromoethylphosphate, (meth) acryloyloxyethylphenylphosphonate, di(2-(meth) acryloyloxyethyl)pyrophosphate, 2-(meth) acryloyloxyethyldihydrogendithiophosphonate, 10-(meth) acryloyloxydecyldihydrogenthiophosphate. These polymers may contain a polymerizable monomer having no acidic group in addition to the above polymerizable monomer as far as it does not affect formation of a cement reactive phase.

Among these polymers, a homopolymer or a copolymer of α-β unsaturated carboxylic acid is preferred, which has a relatively slow acid-base reaction rate with an acid reactive element. More preferred are an acrylic acid polymer, an acrylic acid-maleic acid copolymer, an acrylic acid-itaconic acid copolymer.

The above multi-functional filler of the present invention maybe used as a filler characterized by a matrix mainly containing an organic polymer material. Most preferably, itmay be used in a dental composition such as a dental restorative material to impart the excellent properties to the composition. Specifically, since a dental composition containing the multi-functional filler of the present invention has the diffusivity to the incident light, it does not show directivity of the color tone, therefore, a uniform color tone can be observed from any directions. In addition, the sustained fluoride releasability can be imparted to a dental composition comprising this multi-functional filler by using a fluoride-containing glass as the inorganic fine particle. Moreover, the multi-functional filler can impart the composition with the excellent polishability and the excellent glossiness after polishing due to the existence of the cement reactive phase to the composition.

In addition, in order to pack this multi-functional filler into a composition at a large amount, the outermost polysiloxane film is further treated with an organosilane compound represented by the general formula (II):

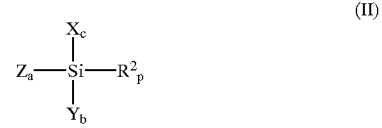

wherein Z is $R^1O-$ or $OCN-$, X is halogen, Y is $-OH$, $R^1$ is an organic group having a carbon number of 8 or less, $R^2$ is an organic group having a carbon number of 6 or less, p is an integer of 1~ to 3, and a, b and c are an integer of 0 to 3, provided that a+b+c+p=4. Thus, this allow the multi-functional filler to be packed at a large amount, to satisfy the properties required as a dental composition.

Embodiments of organosilane compounds represented by the general formula (II) are methyltrimethoxysilane, ethyltrimethoxysilane, methoxytripropylsilane, propyltriethoxysilane, hexyltrimethoxysilane, vinyltrimethoxysilane, vinyltriethoxysilane, vinyltris(β-methoxyethoxy)silane, γ-methacryloxypropyltrimethoxysilane, γ-glycidoxypropyltrimethoxysilane, γ-mercaptopropyltrimethoxysilane, γ-aminopropyltriethoxysilane, 3-aminopropyltriethoxysilane, methyltrichlorosilane, phenyltrichrolosilane, trimethylsilyl isocyanate, vinylsilyl triisocianate, phenylsilyl triisociyanate and the like.

Among these organosiloxane compound, compounds known as a silane coupling agent in the dental field are effective, such as vinyltrimethoxysilane, vinyltriethoxysilane, vinyltrichlorosilane, vinyltris(β-methoxyethoxy)silane, γ-methacryloxypropyltrimethoxysilane, γ-glycidoxypropyltrimethoxysilane, γ-mercaptopropyltrimethoxysilane, γ-aminopropyltrimethoxysilane and the like. More preferred is γ-methacryloxypropyltrimethoxysilane. These organosilane compounds may be used alone or in combination thereof Compatibility with a resin component is enhanced by these organosilane compounds because they are effectively and uniformly treated by a reaction with many OH groups present on a polysiloxane film.

Another aspect of dental compositions containing the above multi-functional filler of the present invention is a dental composition which comprises: (a) the present multi-functional filler, (b) a polymerizable monomer and (c) a polymerization initiator.

In the composition, not only the multi-functional filler of the present invention can be uniformly dispersed in the non-aggregated state in a matrix containing an organic polymer material as a main component due to the presence of a polysiloxane film on the surface thereof, but also it has the characteristic that a cured composition manifests the excellent physical property due to the high compatibility with an organic matrix. In addition, a cured dental composition containing a multi-functional filler of the present invention as a filler has the excellent wear resistance in spite of such a fine filler, in addition to the excellent glossiness after polishing originally derived from fineness of a filler. It is believed that this excellent wear resistance is imparted by the fact that a filler interacts with a matrix with the strong compatibility, due to the action of a polysiloxane film on the surface of a multi-functional filler and an organosilane compound which is added upon dispersion in a matrix.

A polymerizable monomer which can be used in a dental composition together with a multi-functional filler of the present invention, can be used by selecting from the known monofunctional and multifunctional polymerizable monomers which are generally used as a dental composition.

Representative examples which are generally used suitably are polymerizable monomers having an acryloyl group and/or a methacryloyl group. In the present invention, (meth)acrylate or (meth)acryloyl represented inclusively both acryloyl group-containing polymerizable monomers and methacryloyl group-containing polymerizable monomers.

Embodiments thereof are as follows:

As polymerizable monomers having no acidic group, monofuinctional monomer: (meth)acrylic acid esters such as methyl(meth)acrylate, ethyl(meth)acrylate, butyl(meth)acrylate, hexyl(meth)acrylate, tetrahydrofurfuryl(meth)acrylate, 2-hydroxyethyl(meth)acrylate, grycidyl(meth)acrylate, lauryl(meth)acrylate, cyclohexyl-(meth)acrylate, allyl(meth)acrylate, 2-ethoxyethyl(meth)acrylate, methoxy polyethylene glycol(meth)acrylate, glycerol(meth)acrylate, isobonyl(meth)acrylate and the like, silane compounds such as γ-(meth)acryloyloxypropyltrimethoxysilane, γ-(meth)acryloyloxypropyltriethoxysilane and the like, nitrogen-containing compounds such as 2-(N,N-dimethylamnino)ethyl(meth)acrylate, N-methylol(meth)acrylamide, diacetone(meth)acrylamide and the like, aromatic bifunctional monomer:

2,2-bis(4-(mheth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentathoxyphenyl)propane, 2,2-bis(4-(meth)acryloyloxydipropoxyphenyl)propane, 2,2-bis(4-(meth)acryloyloxyethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane and the like, Aliphatic bifunctional monomer:

2-hydroxy-3-acryloyloxypropylmethacrylate, hydroxypivalic acid neopentylglycol di(meth)acrylate, ehylne glycol di(meth)acrylate ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol(meth)acrylate, 1,6-hexanediol(meth)acrylate, glycerin di(meth)acrylate and the like, trifunctional monomer:

trimethylolpropane tri(meth)acrylate, treimethylolethane tri(meth)acrylate, trimethylolmethane tri(meth)acrylate, pentaerythritol tri(meth) acrylate tri(meth)acrylate and the like, Tetrafunctional monomer:

pentaerythritol tetra(meth)acrylate, ditrimethylolporpane tetra(meth)acrylate and the like.

In addition, embodiments of an urethane system polymerizable monomer are di(meth)acrylates having a bifunctional or trifunctional or more-functional urethane linkage which are derived from an adduct of a polymerizable monomer having a hydroxy group such as 2-hydroxyethyl (meth)acrylate, 2-hydroxypropyl (meth)acrylate and 3-chloro-2-hydroxypropyl (meth)acrylate and a diisocyanate compound such as methylcyclohexane diisocyanate, methylene bis(4-cyclohexylisocyanate), isophorone diisocyanate, diisocyanate methylbenzene and, 4,4-diphenylmethane diisocyanate.

In addition to the aforementioned (meth)acrylate system polymerizable monomers, other polymerizable monomers, for example, a monomer, an oligomer or a polymer having at least one polymerizable group in the molecule may be used depending upon the purpose of a dental composition without any limitation. In addition, there is no problem that the polymerizable monomers have a substituent such as an acidic group, a fluoro group and the like.

In the present invention, a polymerizable monomer includes not only a single component but also a mixture of a plurality of polymerizable monomers.

In addition, when a polymerizable monomer has the extremely high viscosity at room temperature or when a polymerizable monomer is a solid at room temperature, it is preferably used as a mixture of polymerizable monomers by combining with a polymerizable monomer having the low viscosity. This combination may comprise not only two kinds but also three kinds or more.

In addition, since a polymer comprising only monofunctional polymerizable monomers has no cross-linking structure, it generally has a tendency to be inferior in the mechanical strength of a polymer.

For that reason, when a polymerizable monomer is used, it is preferable that it is used with a polyfunctional polymerizable monomer. The most preferable combination of polymerizable monomers is a manner of combining an aromatic compound of a bifunctional polymerizable monomer as a main component with an aliphatic compound of a bifunctional polymerizable monomer.

More particularly, there is a combination of 2,2-bis(4-(3-methacryloyloxy-2-hydroxypropoxy)phenyl)propane (Bis-GMA) and triethylene glycol dimethacrylate (TEGDMA).

When a teeth substance and a nonprecious metal adhering property is imparted to a dental composition containing a multi-functional filler of the present invention, it is effective to use a polymerizable monomer containing an acid group such as a phosphoric acid group, a carboxylic acid group, a sulfonic acid group or the like in the molecule as a part or the whole of a polymerizable monomer.

In addition, in order to enhance a precious metal adhering property, it is also effective to the present invention to use those polymerizable monomers containing a sulfuir atom in the molecule. Embodiments of these polymerizable monomers having the adhering ability are as follows:

Carboxylic acid group-containing polymerizable monomer:
(meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 2-(meth)acryroyloxybenzoic acid, β-(meth)acryroyloxyethyl hydrogen succinate, β-(meth)acryroyloxyethyl hydrogen maleate, 1,1-(meth)acryloyloxy-1,1-undecanedicarboxylic acid, p-vinylbenzoic acid and the like, phosphate group-containing monomer:
2-(meth)acryloyloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl)hydrogen phosphate, 2-(meth)acryloyloxyphenyl hydrogen phosphate and the like, Sulfonic group-containing monomer:
2-(meth)acrylamide-2-methylpropanesulfonic acid,
4-(meth)acryloyloxybenzenesulfonic acid,
3-(meth)acryloyloxypropanesulfonic acid and the like, Sulfur atom-containing monomer:
(meth)acrylate having a triazinethiol group, (meth)acrylate having a mercapto group, (meth)aceylate having a polysulfide group, (meth)acrylate having a thiophosphate group, (meth)acrylate having a disulfide group, (meth)acrylate having a mercaptodithiazole group, (meth)acrylate having a thiouracil group, (meth)acrylate having a thiirane group and the like.

These polymerizable monomers are used alone or as a mixture of two or more without any problem.

A polymerization initiator which can be used with a multi-functional filler of the present invention in a dental composition is not particularly limited and the known radical generator can be used without any limitation.

Polymerization initiators are generally classified into initiators which initiate polymerization by mixing prior to use (chemical polymerization initiator), initiators which initiate polymerization by heating or warming (thermal polymerization initiator), and initiators which initiate polymerization by light irradiation (photoinitiators).

As a chemical polymerizable initiator, there are polymerizable initiator systems of a redox type comprising an organic peroxide/an amine compound or an organic peroxide/an amine compound/a sulfinic acid salt, or an organic peroxide/an amine compound/a borate compound, and organometal type initiator system which initiates polymerization by a reaction with oxygen or water. Further, sulfinic acid salts and borate compounds can also initiate polymerization by a reaction with a polymerizable monomer having an acidic group.

Embodiments of the aforementioned organic peroxide are benzoylperoxide, parachlorobenzoylperoxide, 2,4-dichlorobenzoyl peroxide, 2,5-dihydroperoxy-2,5-dimethylhexane, methyl ethyl ketone peroxide, tertiary-butyl peroxide benzoate and the like.

As the aforementioned amine compound, a secondary or tertiary amine in which an amine group is bound to an aryl group is preferable and embodiments thereof are p-N,N-dimethyltoluidine, N,N-dimethylaniline, N-β-hydroxyethylamine, N,N-di(β-hyidroxyethyl)aniline, p-N,N-di(β-hydroxyethyl)toluidine, N-methylaniline, p-N-methyltoluidine and the like.

Embodiments of the aforementioned sulfinic acid salt are sodium benzenesulfinate, lithium benzenesulfinate, sodiump-toluenesulfinate and the like.

As the aforementioned borate compound, there are trialkylphenylboron, and sodium salt, lithium salt, potassium salt, magnesium salt, tetrabutyl ammonium salt, tetramethyl ammonium salt of trialkyl(p-fluorophenyl)boron (wherein alkyl group is n-butyl group, n-octyl group, n-dodecyl group or the like). In addition, as the aforementioned organometal type polymerizable initiator, there are organic boron compounds such as triphenylborane, tributylborane, partial oxide of tributylborane and the like. In addition, as a thermal polymerization initiator by heating or warming, azo compounds such as azobisisobutyronitrile, methyl azobisisobutyrate, azobiscyano valeric acid and the like are suitably used.

On the other hand, as a photoinitiator, there are a photoinitiator comprising a photosensitizer, a photosensitizer/a photopolymerization promotor and like.

Embodiments of the aforementioned photosensitizer are α-diketones such as benzil, camphorquinone, α-naphtil, acetonaphtone, p,p'-dimethoxybenzil, pentadione, 1,2-phenanthrenquinone, 1,4-phenanthrenquinone, 3,4-phenanthrenquinone, 9,10-phenanthrenquinone, naphthoquinone and the like benzoin alkyl ethers such as benzoin, benzoin methyl ether, benzoin ethyl ether and the like, thioxanthones such as thioxanthone, 2-chlorothioxanthone, 2-methylthioxanthone, 2-hydroxythioxanthone, 2,4- diethylthioxanthone, 2,4-diisopropylthioxanthone and the like, benzophenones such as benzophenone, p-chlorobenzophenone, p-methoxybenzophenone and the like, acylphosphineoxides such as 2,4,6-trimethylbenzoyl diphenylphosphineoxide, bis(2,6-dimethoxybenzoyl)-2,4,4-trimethylpentylphosphineoxide and the like, α-aminoacetophenones such as 2-benzyldimethylamino-1-(4-morpholinophenyl)butanone-1,2-benzyl-diethylamino-1-(4-morpholinophenyl)propanone-1 and the like, ketals such as benzyldimethylketal, benzyldiethylketal, benzyl(2-methoxyethylketal) and the like, titanocenes such as bis(cyclopentadienyl)-bis[2,6-difluoro-3-(1-pyrolyl)phenyl] titanium, bis(cyclopentadienyl)-bis(pentanefluorophenyl) titanium, bis(cyclopentadienyl)-bis(2,3,5,6-tetrafluoro-4-disiloxyphenyl)-titanium and the like.

Embodiments of the aforementioned photopolymerization promoters are tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 2-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N, N-dimethylhexylamine, N,N-dimethyldodecylamine, N,N-dimethylstearylamine, 2,2'-(n-butylimino)diethanol and the like, secondary amines such as N-phenylglycine and the like, barbituric acid such as 5-butylbarbituric acid, 1-benzyl-5-phenylbarbituric acid and the like, tin compounds such as dibutyltin diacetate, dibutyltin dilaurate, dioctyltin dilaurate, dioctyltin diperacetate, dioctyltin bis(mercaptoacetic acid isooctyl ester) salt, tetramethyl-1,3-diacetoxydistannoxane and the like, aldehyde compounds such as laurylaldehyde, terephthalaldehyde and the like, sulfur-containing compounds such as dodecylmercaptan, 2-mercaptobenzoxazole, 1-decanethiol, thiosalicylic acid and the like.

In addition, for improving the photopolymerization promoting ability, the additions of oxycarboxylic acids such as citric acid, maleic acid, tartaric acid, glycolic acid, gluconic acid, α-oxyisobutyric acid, 2-hydroxypropioic acid, 3-hydroxybutanoic acid 4-hydroxybutanoic acid, dimethylolpropioic acid and the like is effective besides the additions of the aforementioned photopolymerization promoters.

Those polymerization initiators may be used alone or as a mixture of tAo or more of them. In addition, they can be used in a combination irrespective of a polymerization form and a kind of a polymerization-initiator.

An amount of a polymerization initiator to be added may be appropriately selected depending upon the use. In general, the amount may be selected from a rangeof 0.1~10 parts by weight relative to a polymerizable monomer.

Among the aforementioned polymerization initiators, it is preferable to use a photopolymerization initiator which generates a radical by light irradiation and such the initiator is most suitably used in that a dental composition can be polymerized in the state where an air is mixed therein at a small amount. In addition, among photopolymerization initiators, a combination of α-diketone and tertiary amine is preferable and a combination of camphorquinone with an aromatic amine having an amino group directly bound to a benzene ring such as ethyl p-N,N-dimethylaminobenzoate and the like or an aliphatic amine having a double bond in the molecule such as N,N-dimethylaminoethyl methacrylate is most preferable.

In addition, sensitizing pigments such as coumarin, cyanine, thiazine and the like, a light acid generator which produces Bronsted acid or Lewis acid by light irradiator such as a s-triazine derivative substituted which a halomethyl group, diphenyl iodonium salt compound and the like, quaternary ammonium halides, transition metal compound are also suitably used depending upon the use.

Another filler which can be used in a dentalcomposition in combination with multi-functional fillers of the present invention is not particularly limited, but the known filler, for example, an inorganic filler and/or an organic filler and/or an organic-inorganic compound filler, can be used without any limitation. A shape of such a filler is not particularly limited, but particle shapes such as of sphere, needle, plate, crushed and flake may be taken. Also, a kind of the filler is not particularly limited.

Examples of an inorganic filler include quartz, amorphous silica, aluminium silicate, aluminium oxide, titanium oxide, zirconium oxide, various glasses (including a glass prepared by a melting process, a synthetic glass prepared by a sol-gel process, a glass produced by a vapor phase process), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite and the like. Among them, preferred are an aluminosilicate glass, a borosilicate glass, an aluminoborate glass, a boroaluminosilicate glass and the like, which contain heavy metals such as sodium, strontium, barium and lanthanum and/or fluoride. An average particle size of the inorganic filler is not particularly limited, but it is preferably in a range of 0~10 μm, and more preferably in a range of 0~5 μm.

In addition, ultrafine particle inorganic fillers such as Aerosil produced by a vapor phase process or a particle of silica-zirconia oxide produced from a solution by a sol-gel process can be used. In addition, an aggregated inorganic filler in which such the ultrafine particle is aggregated may be used without any problem.

In addition, an organic filler can be prepared by polymerizing a monomer having a polymerizable group, and a kind thereof is not particularly limited. Examples of an organic filler include fillers prepared by (co)polymerizing a polymerizable monomer, alone or in combination, such as unsaturated aromatic compounds such as styrene, α-methylstyrene, halogenated styrene and divinylbenzene; unsaturated esters such as vinyl acetate and vinyl propionate; unsaturated nitrites such as acrylonitrile; and butadiene and isoprene. Particularly preferred is a filler prepared by polymerizing the above polymerizable monomer which is known in the dental field. A process for producing an organic filler is also not particularly limited, but processes such as emulsion polymerization, suspension polymerization and dispersion polymerization, or a process of grinding a preformed polymer bulk can be employed.

Alternatively, an organic-inorganic compound filler containing an inorganic particle in an organic polymer can be used. An inorganic particle to be contained in an organic polymer is not particularly limited, but the known inorganic particle, for example, the aforementioned inorganic filler can be contained. A process for producing an organic-inorganic compound filler is also not particularly limited, but any process can be adopted. Examples of such the process include a process for micro-encapsulating an inorganic particle with an organic material or grafting the surface of an inorganic particle with an organic material, a process for radical-polymerizing a polymerizable functional group or a polymerizable initiation group on the surface of an inorganic particle after introducing it to the surface, a process for grinding a polymer bulk containing inorganic particles which have been produced in advance, and the like.

An average particle size of an organic or organic-inorganic compound filler is preferably in a range of 1~100 μm, more preferably in a range of 3~50 μm, and most preferably within a range of 5~30 μm. These inorganic, organic and organic-inorganic compound fillers can be used alone or in combination thereof.

Fillers such as inorganic, organic and organic-inorganic compound fillers can be used for a dental composition, after the surface of a particle thereof is treated with, for example, surfactants, fatty acids, organic acids, inorganic acids, silane coupling agents, titanate coupling agents, polysiloxane or the like. These surface treating processes are preferable in that these can enhance the wettability between a resin component and the filler surface and can impart various excellent properties to a dental composition, and these can be arbitrarily selected depending upon the required properties. Moreover, in order to multi-functionalize these fillers, surface treatment with special surface treating agents and/or by a special process of surface treatment can be conducted without any limitation.

A proportion of such the filler in a dental composition may be optionally selected depending upon material property required for a dental composition.

An filling amount of low-viscous materials such as sealants, bonding materials primers, tooth surface treating agents, opacifying agents and cements generally used in the dental field should be set at a relatively small level since higher fluidity required as material property is required for these materials. Therefore, the amount is preferably in a range of 5.0~80.0 parts by weight, more preferably in a range of 30.0~70.0 parts by weight relative to the whole component of a dental composition.

In addition, an filling amount of high-viscous materials such as a composite resin and a beneer crown resin should be set at a relatively high level since, as the required material property, such the shapability is required that does not cause deformation after shape adjustment. Accordingly, the amount is preferably in a range of 50.0~98.0 parts by weight, more preferably in a range of 75.0~98.0 parts by weight relative to the whole component of a dental composition.

In addition, if needed, components such as ultraviolet absorbing agents such as 2-hydroxy-4-methylbenzophenone, polymerization inhibitors such as hydroquinone, hydroquinone monomethyl ether and 2,5-di(tertiary-butyl)-4-methylphenol, anti-discoloring agents, antimicrobial agents, and other conventional known additives may be optionally added to a dental composition.

A packing type of the dental composition of the present invention is not particularly limited, but it may be any one of one-package type, two-package type and the like depending upon a kind of a polymerization initiator or a purpose of use, and it may be appropriately selected depending upon the application.

The organic compound filler of the third aspect of the present invention is a filler which comprises an organic-inorganic polymer particle or an organic polymer particle, in which the surface of the organic-inorganic polymer particle or the organic polymer particle is covered with an inorganic film, and it can impart the excellent polishability, particularly the surface smoothness and glossiness after polishing, as well as the excellent mechanical properties and the durability, and the stable paste handling to a dental composition comprising the organic compound filler of the present invention.

An organic-inorganic polymer particle or an organic polymer particle used in the organic compound filler of the present invention is not particularly limited, but the particles known in the art may be used.

The organic polymer particle may be obtained by polymerizing a monomer having a polymerizable group, and a process for producing the organic polymer particle is not particularly limited. For example, any processes such as emulsion polymerization, suspension polymerization and dispersion polymerization of the polymerizable monomer may be used and, furthermore, it can be carried out by grinding a polymer bulk produced in advance.

Specifically, a polymerizable monomer for producing the organic polymer particle includes, for example, unsaturated aromatics such as styrene, α-methylstyrene, halogenated styrene and divinylbenzene and the like; unsaturated esters such as vinyl acetate and vinyl propionate and the like; unsaturated nitrites such as acrylonitrile; butadien, isoprene and the like. Most preferred is a polymerizable monomer which is known in the dental field and is mentioned later. These polymerizable monomers may be used alone or in combination of two or more of them.

In order to improve the impact resistance, the heat resistance and the solvent resistance of the organic polymer particle itself, it is preferable that a cross-linking monomer, that is, a polymerizable monomer having two or more of polymerizable groups is used. In addition, in order to leave more reactive double bonds on the surface of the organic polymer particle, the particle may be produced from a monomer having three or more polymerizable groups per molecule, or from a mixture of a monomer having three or more polymerizable groups per molecular and a monomer having two of more polymerizable groups per molecule.

Further, in the present invention, it is most preferable that an organic-inorganic polymer particle in which an inorganic particle is contained in an organic polymer particle is used. As the inorganic particle to be contained in the organic-inorganic polymer particle, the known inorganic particles may be used without any limitation. The shape of the inorganic particle may be an optional particle shape such as spherical, needle, plate, crushed, flake and the like, and is not particularly limited. Furthermore, a kind of the inorganic particle is not particularly limited. Specifically, the organic particle includes, for example, quartz, amorphous silica, aluminium silicate, aluminium oxide, titanium oxide, zirconium oxide, various glasses (including a glass formed by a melting process, a synthesized glass by a sol-gel process, a glass formed by a vapor phase process and the like), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite, sodium fluoride, calcium fluoride, and strontium fluoride. These inorganic particles may be used alone or in combination of two or more of them. Among them, as the inorganic particle contained in the organic polymer particle, preferred are an alminosilicate glass, borosilicate glass, aluminoborate glass, boroaluminosilicate glass containing a heavy metal such as strontium, barium, lanthanum and the like and/or fuloride. An average particle size of these inorganic particles is preferably in a range of 0.01~10 μm, more preferably 0.01~2.0 μm.

From a viewpoint of imparting the polishability, particularly the surface smoothness and glossiness after polishing, it is a preferable aspect that, as an inorganic particle, a ultrafine silica particle in which its primary particle is 0.1 μm or less, or another metal compound is used.

The process for producing the organic-inorganic polymer particle is not particularly limited, but any process may be used. For example, there are a process for micro-capsulating or grafting the surface of the inorganic polymer with an organic compound, and a process for polymerizing after introducing a polymerizable functional group or polyrnization intiating group onto the surface of the inorganic particle. However, a process for producing a general organic-inorganic polymer particle known as a process for producing an organic compound filler in the dental field will be described herein.

First, a polymerizable monomer, an inorganic particle and a polymerization initiator are mechanically kneaded by using a mortar, a kneader, a roll, a grinding mixer and the like to prepare a paste. The polymerization initiator is not particularly limited, but the known radical generator may be used without any limitation. For example, organic peroxides such as benzoyl peroxide; azo compounds such as azobisisobutyronitorile; and organometal compound such as tributylboron are suitable. An amount of the polymerization initiator to be added may be selected from a range of 0.1~10 parts by weight relative to the polymerizable monomer. Further, an amount of the inorganic particle to be mixed is preferably in a range of 10~80 parts by weight, more preferably 40~60 parts by weight. When the amount is below the range, problems occur in the mechanical strength and the thermal expansion coefficient and the like of the organic-inorganic polymer particle and, on the other hand, when the amount exceeds this range, problems arise in the mechanical strength and the polishability due to deterioration of the dispersibility of the inorganic particle in the organic-inorganic particle.

Next, this paste is polymerized by using an appropriate polymerization instrument such as a heat-press machine. A polymerization temperature may be appropriately selected depending upon a decomposition temperature of the polymerization initiator and, it is preferably in a range of 20~250 C, more preferably 60~200 C. A polymerization time may be appropriately selected, taking into consideration the polymerization state of a polymer and an amount of the remaining unreacted monomer. Alternatively, polymerization may be generally carried out under an inert gas atmosphere such as nitrogen and argon so as not to discolor the polymer. Although polymerization may be sufficiently carried out at an atmospheric pressure, it may be carried out under pressure, as necessary. Further, preparation of and polymerization of the paste may be carried out simultaneously by using a kneader such as a pressure kneader and the like.

Next, the polymer is ground to obtain an organic-inorganic polymer particle. A process for grinding is not particularly limited, but it may be carried out by using a process generally adopted in the art. For example, a container-driven medium mill such as a ball mill and an oscillating mill, a high-speed rotational mill such as a hammer mill and a turbo mill, a grinding medium agitating mill such as sand grinder and an attritor may be appropriately selected depending upon a necessary average particle size. In addition, it may be carried out under an inert gas atmosphere or in a solvent such as alcohol so as not to discolor the ground compound at milling. Further, an antioxidant, for example, known phenols such as hydroquinone monomethyl ether may be added for grinding. It is preferable that an average particle size of the ground organic-inorganic polymer particle is in a range of 1~100 μm. More preferred is 3~50 μm, and yet more preferred is 5~30 μm.

In the organic-inorganic polymer particle thus obtained having the desired average particle size, an inorganic film is formed on the surface thereof as follows. The organic-inorganic polymer particle ground into the desired average particle size is dispersed in an aqueous medium uniformly. An important thing in a step of forming an inorganic film is to disperse the organic-inorganic polymer particle in the aqueous medium uniformly. Therefore, it is desirable that a polymer soluble in water and alcohol and/or a surfactant are added as a dispersing property modifier. As these dispersing property modifiers, any modifier may be used without any limitation, as far as they are soluble in the aqueous medium. Specifically, they include, for example, poly (vinylpyrrolidone), poly(vinyl alcohol), poly(sodium carbonate), sodium hexametaphosphate, sodium naphthalenesulfonate, sodium dodecylbenzenesulfonate, sodium dodecylsulfate. More preferred are poly (vinylpyrrolidone), sodium dodecylsulfate and the like. These may be used alone or as a mixture of two or more of them. A process of dispersing is not particularly limited, but it may be carried out by a process generally used in the art. For example, a stirrer which can stir a slurry, may be used to stir, such as a universal mixer and a planetary mixer. If it is difficult to disperse, a disperser such as a dissolver and a homogenizer may be used, as needed, in combination or for pre-treatment. More preferred is a disperser which can simultaneously disperse and stir.

To the resulting aqueous medium containing an organic-inorganic polymer particle is added a silane compound represented by the general formula (I):

(I)

wherein Z is RO— or OCN—, X is halogen, Y is —OH, R is an organic group having a carbon number of 8 or less, and n, m and L are an integer of 0~ to 4, provided that n+m+L=4, and/or a low-condensate of the silane compound, and these are hydrolyzed or partially hydrolyzed in the system, and condensed to form an inorganic film.

Alternatively, the silane compound represented by the general formula (I) and/or a low-condensate of the silane compound is hydrolyzed or partially hydrolyzed in the presence of at least one of an organosilane compound represented by the general formula (II):

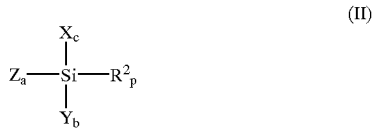

(II)

wherein Z is $R^1O$— or OCN—, X is halogen, Y is —OH, $R^1$ is an organic group having a carbon number of 8 or less, $R^2$ is an organic group, a, b and c are integers of 0~ to 3, and p is an integer of 1~ to 3, provided that a+b+c+p=4, a low-condensate of the organosilane compound, and a metal compound, then they are co-condensed to form an inorganic film.

A form of the compound added in the step of forming the above inorganic film is not particularly limited, but any forms may be used, for example, a monomer, a low-(co-)condensate (oligomer) in which the monomer is partially hydrolyzed and a mixture thereof.

The process of adding them to an aqueous medium is not particularly limited, and the compounds to be added may be added separately, or after pre-mixed, they may be added in one portion or intermittently in a divided manner. However, in order to improve the uniformity of the addition, it is preferred that the compound to be added is diluted with an organic solvent miscible with an aqueous medium, which is added intermittently in a divided manner.

In addition, when a low-(co-)condensate is used for forming an inorganic film, the shape is not particularly limited, but a linear shape thereof is more preferable than a three-dimensional shape. Further, if a degree of polymerization is too large, the (co-)condensation reactivity with the surface of the organic-inorganic particle is inferior, and it is possible that formation of the inorganic film is deteriorated.

In addition, as another process of forming an inorganic film, a process of preparing a solution containing a precursor of the above inorganic film in advance, and then adding an aqueous dispersion containing an organic-inorganic particle to the solution to form a film in the uniform dispersion may be used without any limitation.

Z in the general formula (I) and the general formula (II) represents RO group, $R^1O$ group or OCN group which can generate a silanol group by hydrolysis, X represents halogen, and Y represents OH group. R and $R^1$ are an organic group having a carbon number of 8 or less and, more particularly, there can exemplified alkyl group or alkyl derivative such as methyl, ethyl, 2-chloroethyl, alkyl, aminoethyl, propyl, isopentyl, hexyl, 2-methoxyethyl, phenyl, m-nitrophenyl, 2,4-dichlorophenyl and the like. From a viewpoint of a rate of hydrolysis and discoloration due to remaining carbon in an inorganic film, methyl and ethyl are preferable. In addition, as a halogen, there are chlorine and bromine, and chlorine is preferable.

In addition, $R^2$ in the general formula (II) is not particularly limited as long as it is an organic group, but a shorter main chain of an organic group is preferable in that the structural strength of an inorganic film can be maintained.

As an example of a silane compound represented by the general formula (I), there are tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide (silicon oxide hydrate), tetraisocyanatosilane, ethoxysilane triisocyanate and the like. Among them, tetramethoxysilane and tetraethoxysilane are preferable.

In addition, it is more preferable to be a low-condensate of a silane compound represented by the general formula (I), more particularly, a low-condensate obtained by partially hydrolyzing and condensing a tetramethoxysilane or tetraethoxysilane compound. These silane compounds can be used alone or in combination of two or more of them.

As an example of an organosilane compound represented by the general formula (II), there are methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloyloxypropyltrimethoxysilane, γ-glycidoxypropyltrimethoxysilane, γ-mercaptoropyltrimethoxysilane, γ-aminopropyltriethoxysilane, 3-aminopropyltriethoxysilane, methyltrichlorosilane, phenyltrichlorosilane, trimethylsilyl isocyanate, vinylsilyl triisocyanate, phenylsilyl triisocyanate and the like. Alternatively, low-condensates of these organosilane compounds may be used.

Among those organosilane compounds, vinyltrimethoxysilane, vinyltriethoxysilane, vinyltrichlorosilane, vinyl(β-methoxyethoxy)silane, γ-methacryloyloxypropyltrimethoxysilane, γ-glycidoxypropyltrimethoxysilane, γ-mercaptopropyltrimethoxysilane, γ-aminopropyltrimethoxysilane and the like are preferable, and γ-methacryloyloxypropyltrimethoxysilane is more preferable. These organosilane compounds may be used alone or in combination of two or more of them.

In addition, as a metal compound, there can be used, without any limitation, a metal compound which alone is hydrolyzed or partially hydrolyzed and condensed to form a skeleton of a an inorganic film, a metal compound which makes a modificatory contribution to a skeleton in the presence of another compound forming a skeleton of an inorganic film. As an example of those metal compounds, there are metal halide, metal nitrate, metal sulfate, metal ammonium salt, organometal compound, alkoxy metal compound and derivatives of these metal compounds. The metal compounds may be used alone or in combination of two or more of them. As metal elements which constitute these compounds, there are respective elements of Periodic Table Group I–Group V. Among these metal compounds, metal compounds are preferable which comprise metal elements of Periodic Tables Group III–Group V which can alone be hydrolyzed and condensed to form a three dimensional skeleton are preferable. Metal compounds comprising Zr or Ti are more preferable. When an organic compound filler of the present invention obtained by forming an inorganic film in the presence of a metal compound comprising these two kinds of metal elements are used as a filler for a dental composition, the radiopacity can be imparted to the composition. As a metal compound comprising Zr or Ti, there can be exemplified titanium tetrachloride, titanyl sulfate, methyltrichlorotitanium, dimethyldichlorotitanium, tetramethoxytitanium, tetraethoxytitanium, tetraisopropoxytitanium, tetraisobutoxytitanium, tetrakis(2-ethylhexyloxy)titanium, diethoxydibutoxytitanium, isopropoxytitanium trioctarate, diisopropoxytitanium diacrylate, tributoxytitanium stearate, zirconium tetrachloride, zirconium oxychloride, zirconium acetate, zirconium lactate, tetramethoxyzirconium, tetraethoxyzirconium, tetraisopropoxyzirconium, tetrabutoxyzirconium and the like. Alternatively, derivatives of the aforementioned metal compounds may be used. As a derivative of a metal compound, there can be exemplified a metal compound in which a part of a hydrolyzable group such as halogen, $NO_3$, $SO_4$ alkoxy group, acyloxy group and the like is substituted with a group which can form a chelating compound such as dicarboxylic acid group, oxycarboxylic acid group, β-diketone group, β-ketoester group, β-diester group, alkanolamine group and the like. Alternatively, a low-condensed metal compound (pligomer or polymer) obtained by partially hydrolyzing and low-condensing a metal compound may be used.

Hydrolysis or partial hydrolysis of a compound added to the aforementioned aqueous dispersion is performed under stirring at a relatively low speed. A stirring temperature is in a range of 10 C to 100 C, more preferably in a range of 25 C to 50 C and there is no limitation as long as it is a temperature lower than a boiling point of an aqueous medium. A stirring time is in a range of a few minutes to a few hours, more preferably in a range of 30 minutes to 24 hours, and can be adjusted by a kind and an amount of a compound to be added, a kind, an average particle size and a proportion occupied in its aqueous dispersion of an a polymer particle, a kind of an aqueous medium and a proportion of an aqueous medium occupied in its aqueous dispersion and the like. Stirring does not need a special process but can be performed by adopting an equipment normally employed in the art. For example, stirring may be performed using a stirring machine which can stir a slurry such as a universal mixer, a planetary mixer and the like.

In addition, in order to control a rate of hydrolysis or partial hydrolysis and co-condensation, a sol-gel catalyst such as an acid, an alkali, an organometal compound, a metal alkoxide, a metal chelating compound and the like is preferably added. As an embodiment of a catalyst, there are an inorganic acid such as hydrochloric acid, acetic acid, nitric acid, formic acid, sulfuric acid, phosphoric acid and the like, an organic acid such as para-toluenesulfonic acid, benzoic acid, phthalic acid, maleic acid and the like, an alkali catalyst such as potassium hydroxide, sodium hydroxide, ammonia and the like. In addition, as an aqueous medium used in a step of forming an inorganic film, water and/or an organic solvent miscible with water can be used without any limitation. Particularly preferably, an organic solvent can be appropriately selected from alcohols, ketones and ethers. These organic solvents have the great effects that they not only improve the miscibility of a variety of compounds used in a step of forming an inorganic film but also decrease the aggregability of particles in a heat-treating step and improve the disintegrability. As an embodiment of these organic solvents, there are alcohols such as ethyl alcohol, n-propyl alcohol, isopropyl alcohol, t-butyl alcohol, isobutyl alcohol and the like, ethers such as tetrahydrofuran, dioxane and the like, and ketones such as acetone and the like. These solvents may be used alone or in combination of two or more of them.

Preferably, ethyl alcohol, n-propyl alcohol and isopropylalcohol are suitably used.

In the step of forming the above inorganic film, the proportions of the organic-inorganic polymer particle, the aqueous medium and the compound to be added in an aqueous dispersion are not particularly limited. The aqueous medium is composed of water and/or an organic solvent which is miscible with water. A proportion of water to be added is not particularly limited, as far as it is such that the compound to be added is hydrolyzed or partially hydrolyzed, but it is preferred that a molar ratio of water is 0.5 or more relative to a hydrolyzable group possessed by the compound to be added. The molar ratio is more preferably 1 or more, and yet more preferably 2 or more.

A proportion of the organic solvent miscible with water is not particularly limited as far as it is such that the organic-inorganic polymer particle is dispersed in the aqueous medium uniformly, and the compound to be added is hydrolyzed or partially hydrolyzed uniformly to (co-)condense. In addition, an amount of the compound to be added may be appropriately selected depending upon a process for forming an inorganic film, a kind and an average particle size of the organic-inorganic polymer particle, and it is in a range of 0.1~20.0 parts by weight in terms of $SiO_2$ amount (silane compound alone or a mixture of a silane compound and an organosilane compound) relative to 100 parts by weight of an organic-inorganic polymer particle. Preferred is a range of 0.1~10.0 parts by weight, more preferred is a range of 0.1~5.0 parts by weight. In addition, a ratio of a silane compound and an organic compound present in an inorganic film is 99:1~20:80, preferably 99:1~30:70, more preferably 99:~40:60, in terms of $SiO_2$ amount by weight. Further, in the step of forming an inorganic film, as mentioned above, a catalyst may be added to the aqueous medium, and the amount to be added is preferably 0~10.0 parts by weight, more preferably 0~5.0 parts by weight relative to 100 parts by weight of the compound to be added.

In addition, when an inorganic film is formed in the presence of a metal compound, the metal compound may be present in a range of 0.1~500 parts by weight, more preferably 0.1~200 parts by weight in terms of a metal oxide amount, relative to 100 parts by weight in terms of $Si_2O$ amount.

Next, the organic-inorganic polymer particle thus obtained, having the surface with an inorganic film formed thereon, is separated from the aqueous dispersion. A separation process may be according to the conventional process, and separation and purification may be performed, for example, by centrifugation, reprecipitation, ultrafiltration and the like. Alternatively, by using a drying process such as heating, vacuuming and freezing, an aqueous medium may be removed from an aqueous dispersion. After separation, the inorganic film formed on the surface of the organic-inorganic polymer particle is reinforced by the heat treatment. This heat treatment may be carried out in stationary or in rotatory by using a heat generator such as a box-type heat dryer and a rotary kiln. In addition, when a box-type heat dryer is used, removal of an aqueous medium and reinforcement of the inorganic film can be carried out simultaneously. The heat treatment should be carried out at a low temperature so as not to give any distortion to the structure of the inorganic film.

A temperature for the heat treatment may be appropriately selected to an extent that it has no adverse effect such as carbonization on the organic-inorganic poylmer particle. A temperature for the heat treatment is in a range of 10 C~200 C, more preferably 40 C~150 C. When the temperature is below this range, removal of an aqueous medium is insufficient and, when the temperature exceeds this range, since an aqueous medium is volatilized rapidly, it is possible that defects arise in the inorganic film, or the film peels off from the surface of the particle. Since a heat treating time depends upon the ability of a dryer and the like, it should be appropriately selected, being not limiting.

In this way, a heat-treated granule in which an inorganic film is formed on the surface of an organic-inorganic polymer particle is obtained by the heat treatment. This heat-treated granule is an aggregate of the particles, but it is not a mere aggregate of the particle, but an inorganic film formed by (co-)condensation intervenes on the boundaries between individual particles. Accordingly, as a next step, when this heat-treated granule is disintegrated, then the separated organic-inorganic polymer particle having the surface covered with an inorganic film, that is, an organic compound filler of the present invention can be obtained. The disintegration of the heat-treated granule can be easily done by applying a shearing force or an impact force, and the disintegration process can be canied out, for example, by using a Henschel mixer, a cross rotary mixer, a super mixer, a mortar or the like.

In the organic compound filler of the present invention thus obtained, the surface thereof is covered with the inorganic film. An average particle size and particle size distribution of the organic compound filler in which the surface is covered with an inorganic film can be confirmed by a laser diffraction particle size measuring machine. As the result, it is recognized that the organic compound filler was powdered in the uniform dispersion state because it had the same average particle size and particle size distribution with monodispersion as those measured in the state where the organic-inorganic polymer particle is dispersed uniformly in an aqueous medium. These dispersed state can be observed also by an electron microscope. In addition, a specific surface area of the organic compound filler can be measured by using BET method, and it is confirmed that a specific surface area was increased by formation of the inorganic film. Further, the fluidity and dispersibility of the organic compound filler of the present invention is better in spite of a number of hydroxyl groups on the film surface, because it is believed that the contact between the particles is a point contact due to the irregular parts of the film surface. In addition, it was observed that when this organic compound filler is used in a dental composition, a resin component is penetrated into the irregular parts on the surface of the inorganic film and, thereby, the mechanical property is enhance by the fitting effect.

In addition, in order to pack this organic compound filler into a composition at a large amount, it is effective to further treat the inorganic film with an organosilane compound represented by the general formula (II):

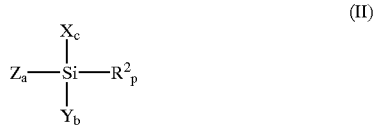

(II)

wherein Z is $R^1O$— or OCN—, X is halogen, Y is —OH, $R^1$ is an organic group having a carbon number of 8 or less, $R^2$ is an organic group, p is an integer of 1~ to 3, and a, b and c are an integer of 0~ to 3, provided that a+b+c+p=4. Thus, this allows an organic compound filler to be packed at a large amount to satisfy the properties required as a dental composition.

As an example of an organosilane compound represented by the general formula (II), there are methyltrimethoxy silane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltriethoxysilane, 3-aminopropyltriethoxysilane methyltrichlorosilane, phenyltrichlorosilane, trimethylsilyl isocyanate, vinylsilyl triisocyanate, phenylsilyl triisocyanate and the like. Alternatively, low-condensates of these organosilane compounds may be used.

Among those organosilane compounds, vinyltrimethoxysilane, vinyltriethoxysilane, vinyltrichlorosilane, vinyl(β-methoxyethoxy)silane, γ-methacryloyloxypropyltrimethoxysilane, γ-glycidoxypropyltrimethoxysilane, γ-mercaptopropyltrimethoxysilane, γ-aminopropyltrimethoxysilane and the like are preferable, and γ-methacryloyloxypropyl-trimethoxysilane are more preferable. These organosilane compounds may be used alone or in combination of two or more of them.

Another aspect of the present invention is a dental composition comprising the present organic compound filler. Specifically, it is a dental composition comprising (a) the organic compound filler of the present invention, (b) a polymerizable monomer and (c) a polymerization initiator.

The organic compound filler of the present invention is characterized in that it can be dispersed uniformly in the non-aggregate state in a resin matrix comprising an organic polymer material as a main component, due to the presence of the inorganic film on the surface thereof In addition, a cured dental composition comprising the organic compound filler of the present invention as a filler has the excellent polishability, particularly the surface smoothness and glossiness after polishing, the mechanical properties and the durability. It is considered that this excellent property is imparted by a filler having interaction with a resin matrix with the strong affinity by an action of an inorganic film present on the surface of an organic compound filler and an organosilane compound which is added upon dispersion into a resin matrix, and the fitting effect of a resin matrix penetrated into the irregular parts on the surface of the inorganic film.

A polymerizable monomer which can be used in a dental composition together with an organic compound filler of the present invention, can be used by selecting from the known monofunctional and multifunctional polymerizable monomers which are generally used as a dental composition.

Representative examples which are generally used suitably are polymerizable monomers having an acryloyl group and/or a methacryloyl group. In the present invention, (meth)acrylate or,(meth)acryloyl represented inclusively both acryloyl group-containing polymerizable monomers and methacryloyl group-containing polymerizable monomers.

Embodiments thereof are as follows:

As polyrnerizable monomers having no acidic group, monofunctional monomer: (meth)acrylic acid esters such as methyl(meth)acrylate, ethyl(meth)acrylate, butyl(meth)acrylate, hexyl(meth)acrylate, tetrahydrofurfuryl(meth)acrylate, 2-hydroxyethyl(meth)acrylate, grycidyl(meth)acrylate, lauryl(meth)acrylate, cyclohexyl(meth)acrylate, allyl(meth)acrylate, 2-ethoxyethyl(meth)acrylate, methoxy polyethylene glycol(meth)acrylate, glycerol (meth)acrylate, isobonyl(meth)acrylate and the like, silane compounds such as γ-(meth)acryloyloxypropyltrimethoxysilane, γ-(meth)acryloyloxypropyltriethoxysilane and the like, nitrogen-containing compounds such as 2-(N,N-dimethylamino)ethyl (meth)acrylate, N-methylol(meth)acrylamide, diacetone (meth)acrylamide and the like, Aromatic Bifunctional Monomer:
  2,2-bis(4-(meth)acryloyloxyphenyl)propane,
  2,2-bis(4-(3-(meth)acryloyloxy-2-hydroxypropoxy) phenyl)propane,
  2,2-bis(4-(meth)acryloyloxyethoxyphenyl)propane,
  2,2-bis(4-(meth)acryloyloxydiethoxyphenyl)propane,
  2,2-bis(4-(meth)acryloyloxytetraethoxyphenyl)propane,
  2,2-bis(4-(meth)acryloyloxypentathoxyphenyl)propane,
  2,2-bis(4-(meth)acryloyloxydipropoxyphenyl)propane,
  2,2-bis(4-(meth)acryloyloxyethoxyphenyl)-2-(4-(meth) acryloyloxydiethloxyphenyl)propane,
  2-(4-(meth)acryloyloxydiethoxyphenyl)-2-(4-(meth) acryloyloxytriethoxyphenyl)propane,
  2-(4-(meth)acryloyloxydipropoxyphenyl)-2-(4-(meth) acryloyloxytriethoxyphenyl)propane,
  2,2-bis(4-(meth)acryloyloxypropoxyphenyl)propane,
  2,2-bis(4-(meth)acryloyloxyisopropoxyphenyl)propane and the like, aliphatic bifunctional monomer:
2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol(meth)acrylate, 1,6-hexanediol (meth)acrylate, glycerin di(meth)acrylate and the like, Trifunctional Monomer:
trimethylolpropane tri(meth)acrylate, treimethylolethane tri(meth)acrylate, trimethylolmethane tri(meth)acrylate, pentaerythritol tri(meth)acrylate and the like, tetrafunctional monomer:
pentaerythritol tetra(meth)acrylate, ditrimethylolporpane tetra(meth)acrylate and the like.

In addition, embodiments of an urethane system polymerizable monomer are di(meth)acrylates having a bifunctional or trifunctional or more-functional urethane linkage which are derived from an adduct of a polymerizable monomer having a hydroxy group such as 2-hydroxyethyl(meth)acrylate, 2-hydroxypropyl(meth)acrylate and 3-chloro-2-hydroxypropyl(meth)acrylate and a diisocyanate compound such as methylcyclohexane diisocyanate, methylene bis(4-cyclohexyl isocyanate), isophorone diisocyanate, diisocyanate methylbenzene and, 4,4-diphenylmethane diisocyanate.

In addition to the aforementioned (meth)acrylate system polymerizable monomers, other polymerizable monomers, for example, a monomer, an oligomer or a polymer having at least one polymerizable group in the molecule may be used depending upon the purpose of a dental composition without any limitation. In addition, there is no problem that the polymerizable monomers have a substituent such as an acidic group, a fluoro group and the like.

In the present invention, a polymerizable monomer includes not only a single component but also a mixture of a plurality of polymerizable monomers.

In addition, when a polymerizable monomer has the extremely high viscosity at room temperature or when a polymerizable monomer is a solid at room temperature, it is preferably used as a mixture of polymerizable monomers by combining with a polymerizable monomer having the low viscosity. This combination may comprise not only two kinds but also three kinds or more.

In addition, since a polymer comprising only monofunctional polymerizable monomers has no cross-linking structure, it generally has a tendency to be inferior in the mechanical strength of a polymer.

For that reason, when a polyrnerizable monomer is used, it is preferable that it is used with a polyfunctional polymerizable monomer. The most preferable combination of polymerizable monomers is a manner of combining an aromatic compound of a bifunctional polymerizable monomer as a main component with an aliphatic compound of a bifunctional polymerizable monomer.

More particularly, there is a combination of 2,2-bis(4-(3-methacryloyloxy-2-hydroxypropoxy)phenyl)propane (Bis-GMA) and triethylene glycol dimethacrylate (TEGDMA).

When a teeth substance and a nonprecious metal adhering property is imparted to a dental composition containing an organic compound filler of the present invention, it is effective to use a polymerizable monomer containing an acid group such as a phosphoric acid group, a carboxylic acid group, a sulfonic acid group or the like in the molecule as a part or the whole of a polymerizable monomer.

In addition, in order to enhance a precious metal adhering property, it is also effective to the present invention to use those polymerizable monomers containing a sulfur atom in the molecule. Embodiments of these polyrnerizable monomers having the adhering ability are as follows:

Carboxylic acid group-containing polymerizable monomer:
(meth)acrylic acid, 1,4-di(meth)acryloyloxyethyl-pyromellitic acid, 6-(meth)acryloyloxynaphtalene-1,2,6-tricarboxylic acid, N-(meth)acryroyl-β-aminobenzoic acid, N-(meth)acryroyl-5-aminosalicylic acid, 4-(meth)acryroyloxyethyltrimellic acid and anhydride thereof, 2-(meth)acryroyloxybenzoic acid, β-(meth)acryroyloxyethyl hydrogen succinate, β-(meth)acryroyfoxyethyl hydrogen maleate, 11-(meth)acryloyloxy-1,1-undecanedicarboxylic acid, p-vinylbenzoic acid and the like, Phosphate Group-containing Monomer:
2-(meth)acryloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl), hydrogen phosphate, 2-(meth)acryloyloxyphenyl hydrogen phosphate and the like, Sulfonic Group-containing Monomer:
2-(meth)acrylamide-2-methylpropanesulfonic acid,
4-(meth)acryloyloxybenzenesulfonic acid,
3-(meth)acryloyloxypropanesulfonic acid and the like, Sulfur Atom-containing Monomer:
(meth)acrylate having a triazinethiol group, (meth)acrylate having a mercapto group, (meth)acrylate having a polysulfide group, (meth)acrylate having a thiophosphate group, (meth)acrylate having a disulfide group, (meth)acrylate having a mercaptodithiazdle group, (meth)acrylate having a thiouracil group, (meth)acrylate having a thiirane group and the like.

These polymerizable monomers are used alone or as a mixture of two or more without any problem.

A polymerization initiator which can be used with an organic compound filler of the present invention in a dental composition is not particularly limited and the known radical generator can be used without any limitation.

Polymerization initiators are generally classified into initiators which initiate polymerization by mixing prior to use (chemical polymerization initiator), initiators which initiate polymerization by heating or warming (thermal polymerization initiator), and initiators which initiate polymerization by light irradiation (photoinitiators).

As a chemical polymerizable initiator, there are polymerizable initiator systems of a redox type comprising an organic peroxide/an amine compound or an organic peroxide/an amine compound/a sulfmic acid salt, or an organic peroxide/an amine compound/a borate compound, and organometal type initiator system which initiates polymerization by a reaction with oxygen or water. Further, sulfinic acid salts and borate compounds can also initiate polymerization by a reaction with apolymerizable monomer having an acidic group.

Embodiments of the aforementioned organic peroxide are benzoylperoxide, parachlorobenzoylperoxide, 2,4-dichlorobenzoyl peroxide, 2,5-dihydroperoxy-2,5-dimethylhexane, methyl ethyl ketone peroxide, tertiary-butyl peroxide benzoate and the like.

As the aforementioned amine compound, a secondary or tertiary amine in which an amine group is bound to an aryl group is preferable and embodiments thereof are p-N,N-dimethyltoluidine, N,N-dimethylaniline, N-β-hydroxyethylamine, N,N-di(β-hydroxyethyl)aniline, p-N,N-di(β-hydroxyethyl)toluidine, N-methylaniline, p-N-methyltoluidine and the like.

Embodiments of the aforementioned sulfinic acid salt are sodium benzenesulfinate, lithium benzenesulfinate, sodium p-toluenesulfinate and the like.

As the aforementioned borate compound, there are trialkylphenylboron, and sodium salt, lithium salt, potassium salt, magnesium salt, tetrabutyl ammonium salt, tetramethyl ammonium salt of trialkyl (p-fluorophenyl)boron (wherein alkyl group is n-butyl group, n-octyl group, n-dodecyl group or the like). In addition, as the aforementioned organometal type polymerizable initiator, there are organic boron compounds such as triphenylborane, tributylborane, partial oxide of tributylborane and the like. In addition, as a thermal polymerization initiator by heating or warming, azo compounds such as azobisisobutyronitrile, methyl azobisisobutyrate, azobiscyano valeric acid and the like are suitably used.

On the other hand, as a photoinitiator, there are a photoinitiator comprising a photosensitizer, a photosensitizer/a photopolymerization promotor and like.

Embodiments of the aforementioned photosensitizer are α-diketones such as benzil, camphorquinone, α-naphtil, acetonaphtone, p,p'-dimethoxybenzil, pentandione, 1,2-phenanthrenquinone, 1,4-phenanthrenquinone, 3,4-phenanthrenquinone, 9,10-phenanthrenquinone, naphthoquinone and the like benzoin alkyl ethers such as benzoin, benzoin methyl ether, benzoin ethyl ether and the like, thioxanthones such as thioxanthone, 2-chlorothioxanthone, 2-methylthioxanthone, 2-hydroxythioxanthone, 2,4-diethylthioxanthone, 2,4-diisopropylthioxanthone and the like, benzophenones such as benzophenone, p-chlorobenzophenone, p-methoxybenzophenone and the like, acylphosphineoxides such as 2,4,6-trimethylbenzoyl diphenylphosphineoxide, bis(2,6-dimethoxybenzoyl)-2,4,4-trimethylpentylphosphineoxide and the like, α-aminoacetophenones such as 2-benzyldlmethylamino-1-(4-morpholinophenyl)butanone-1,2-benzyl-diethylamino-1-(4-morpholinophenyl)propanone-1 and the like, ketals such as benzyldimethylketal, benzyldiethylketal, benzyl(2-methoxyethylketal) and the like, titanocenes such as bis(cyclopentadieinyl)-bis[2,6-difluoro-3-(1-pyrolyl)phenyl] titanium, bis(cyclopentadienyl)-bis(pentarenfluorophenyl) titanium, bis(cyclopentadienyl)-bis(2,3,5,6-tetrafluoro-4-disiloxyphenyl)-titanium and the like.

Embodiments of the aforementioned photopolymerization promoters are tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 2-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, 2,2'-(n-butylimino)diethanol and the like, secondary amines such as N-phenylglycine and the like, barbituric acid such as 5-butylbarbituric acid, 1-benzyl-5-phenylbarbituric acid and the like, tin compounds such as dibutyltin diacetate, dibutyltin dilaurate, dioctyltin dilaurate, dioctyltin diperacetate, dioctyltin bis(mercaptoacetic acid isooctyl ester) salt, tetramethyl-1,3-diacetoxydistannoxane and the like, aldehyde compounds such as laurylaldehyde, terephthalaldehyde and the like, sulfur-containing compounds such as dodecylmercaptan, 2-mercaptobenzoxazole, 1-decanethiol, thiosalicylic acid and the like.

In addition, for improving the photopolymerization promoting ability, the additions of oxycarboxylic acids such as citric acid, maleic acid, tartaric acid, glycolic acid, gluconic acid, α-oxyisobutyric acid, 2-hydroxypropioic acid, 3-hydroxybutanoic acid 4-hydroxybutanoic acid, dimethylolpropioic acid and the like is effective besides the additions of the aforementioned photopolymerization promoters.

Those polymerization initiators may be used alone or as a mixture of two or more of them. In addition, they can be used in a combination irrespective of a polymerization form and a kind of a polymerization initiator.

An amount of a polymerization initiator to be added may be appropriately selected depending upon the use. In general, the amount may be selected from a range of 0.1~10 parts by weight relative to a polymerizable monomer.

Among the aforementioned polymerization initiators, it is preferable to use a photopolymerization initiator which generates a radical by light irradiation and such the initiator is most suitably used in that a dental composition can be polymerized in the state where an air is mixed therein at a small amount. In addition, among photopolymerization initiators, a combination of α-diketone and tertiary amine is preferable and a combination of camphorquinone with an aromatic amine having an amino group directly bound to a benzene ring such as ethyl p-N,N-dimethylaminobenzoate and the like or an aliphatic amine having a double bond in the molecule such as N,N-dimethylaminoethyl methacrylate is most preferable.

In addition, sensitizing pigments such as coumarin, cyanine, thiazine and the like, a light acid generator which produces Bronsted acid or Lewis acid by light irradiator such as a s-triazine derivative substituted which a halomethyl group, diphenyl iodonium salt compound and the like, quaternary ammonium halides, transition metal compound arealso suitably used depending upon the use.

Another filler which can be used in a dental composition in combination with organic compound fillers of the present invention is not particularly limited, but the known filler, for example, an inorganic filler and/or an organic filler and/or an organic-inorganic compound filler, can be used without any limitation. A shape of such a filler is not particularly limited, but particle shapes such as of sphere, needle, plate, crushed and flake may be taken. Also, a kind of the filler is not particularly limited.

Examples of an inorganic filler include quartz, amorphous silica, aluminium silicate, aluminium oxide, titanium oxide, zirconium oxide, various glasses (including a glass prepared by a melting process, a synthetic glass prepared by a sol-gel process, a glass produced by a vapor phase process), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite and the like. Among them, preferred are an aluminosilicate glass, a borosilicate glass, an aluminoborate glass, a boroaluminosilicate glass and the like, which contain heavy metals such as sodium, strontium, barium and lanthanum and/or fluoride. An average particle size of the inorganic filler is not particularly limited, but it is preferably in a range of 0~10 μm, and more preferably in a range of 0~5 μm.

In addition, ultrafine particle inorganic fillers such as Aerosil produced by a vapor phase process or a particle of silica-zirconia oxide produced from a solution by a sol-gel process can be used. In addition, an aggregated inorganic filler in which such the ultrafine particle is aggregated may be used without any problem.

In addition, an organic filler can be prepared by polymerizing a monomer having a polymerizable group, and a kind thereof is not particularly limited. Examples of an organic filler include fillers prepared by (co)polymerizing a polymerizable monomer, alone or in combination, such as unsaturated aromatic compounds such as styrene, α-methylstyrene, halogenated styrene and divinylbenzene; unsaturated esters such as vinyl acetate and vinyl propionate; unsaturated nitrites such as acrylonitrile; and butadiene and isoprene. Particularly preferred is a filler prepared by polymerizing the above polymerizable monomer which is known in the dental field. A process for producing an organic filler is also not particularly limited, but processes such as emulsion polymerization, suspension polymerization and dispersion polymerization, or a process of grinding a preformed polymer bulk can be employed.

Alternatively, an organic-inorganic compound filler containing an inorganic particle in an organic polymer can be used. An inorganic particle to be contained in an organic polymer is not particularly limited, but the known inorganic particle, for example, the aforementioned inorganic filler can be contained. A process for producing an organic-inorganic compound filler is also not particularly limited, but any process can be adopted. Examples of such the process include a process for micro-encapsulating an inorganic particle with an organic material or grafting the surface of an inorganic particle with an organic material, a process for radical-polymerizing a polymerizable functional group or a polymerizable initiation group on the surface of an inorganic particle after introducing it to the surface, a process for grinding a polymer bulk containing inorganic particles which have been produced in advance, and the like.

An average particle size of an organic or organic-inorganic compound filler is preferably in a range of 1~100 µm, more preferably in a range of 3~50 µm, and most preferably within a range of 5~30 µm. These inorganic, organic and organic-inorganic compound fillers can be used alone or in combination thereof.

Fillers such as inorganic, organic and organic-inorganic compound fillers can be used for a dental composition, after the surface of a particle thereof is treated with, for example, surfactants, fatty acids, organic acids, inorganic acids, silane coupling agents, titanate coupling agents, polysiloxane or the like. These surface treating processes are preferable in that these can enhance the wettability between a resin component and the filler surface and can impart various excellent properties to a dental composition, and these can be arbitrarily selected depending upon the required properties. Moreover, in order to multi-functionalize these fillers, surface treatment with special surface treating agents and/or by a special process of surface treatment can be conducted without any limitation.

A proportion of such the filler in a dental composition may be optionally selected depending upon material property required for a dental composition.

An filling amount of low-viscous materials such as sealants, bonding materials, primers, tooth surface treating agents, opacifying agents and cements generally used in the dental field should be set at a relatively small level since higher fluidity required as material property is required for these materials. Therefore, the amount is preferably in a range of 5.0~80.0 parts by weight, more preferably in a range of 30.0~70.0 parts by weight relative to the whole component of a dental composition.

In addition, an filling amount of high-viscous materials such as a composite resin and a beneer crown resin should be set at a relatively high level since, as the required material property, such the shapability is required that does not cause deformation after shape adjustment. Accordingly, the amount is preferably in a range of 50.0~98.0 parts by weight, more preferably in a range of 75.0–98.0 parts by weight relative to the whole component of a dental composition.

In addition, if needed, components such as ultraviolet absorbing agents such as 2-hydroxy-4-methylbenzophenone, polymerization inhibitors such as hydroquinone, hydroquinone monomethyl ether and 2,5-di(tertiary-butyl)-4-methylphenol, anti-discoloring agents, antimicrobial agents, and other conventional known additives may be optionally added to a dental composition.

A packing type of the dental composition of the present invention is not particularly limited, but it may be any one of one-package type, two-package type and the like depending upon a kind of a polymerization initiator or a purpose of use, and it may be appropriately selected depending upon the application.

A modified filler of the forth aspect of the present invention is an inorganic fine particle having an average particle size of 0.01~5 µm and its surface is coated with polyorganosiloxane. Like this, since the modified filler is a monodisperse fine particle having a small average particle size and a narrow particle size dispersion, a dental composition containing a modified filler of the present invention possesses the surface smoothness which can manifest the excellent glossiness on the polished surface when polished after curing. In addition, although when such the fine particle filler is contained, the wear resistance and the durability are inferior due to the worse dispersibility, a modified filler of the present invention is uniformly dispersed in a composition without aggregation and at the same time has the excellent wear resistance and durability conjointly with the effect of formation of a polyorganosiloxane film.

Examples of an inorganic fine particle having an average particle size of 0.01~5 µm used in the present invention are not particularly limited but include quartz, amorphous silica, aluminum silicate, aluminum oxide, titanium oxide, zirconium oxide, various glasses (including a glass by a melting process, a synthetic glass by a sol-gel process, a glass produced by a vapor phase process and the like), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boro carbide, calcium hydroxide, strontium hydrixide, zeolite and the like. Preferably, there are glasses such as aluminosilicate glass, borosilicate glass aluminoborate glass and boroaluminosilicate glass which contain a heavy metal such as strontium, barium, lanthanum and the like and/or fluoride. However, since an inorganic fine particle having an average particle size of 0.01~5 µm used in the present invention is obtained by a wet-grinding step or a wet-dispersion step, a metal fluoride such as sodium fluoride, calcium fluoride, strontium fluoride and the like is not preferable.

This inorganic fine particle having an average particle size of 0.01~5 µm can be usually obtained by wet-grinding a commercially available raw material inorganic particle which is used as a filler or the like. A wet-grinding does not need special process but can be performed by a process which is generally used in the art. For example, a raw material inorganic particle may be fine-ground using a container-driven medium mill such as a ball mill, an oscillating mill and the like, a grinding medium agitating mill, such as an attritor, a sand grinder, an annealer mill, a tower mill and the like. As an aqueous medium, water alone or a medium in which a part or all of water is substituted with an aqueous solvent such as alcohols, ketones such as acetone and the like or ethers and the like as necessary may be used. When these aqueous solvents are used, the aggregating force of a solidified material after heat-treatment is weakened and disintegration can be easily performed. The wet-grinding conditions are different depending upon a size, hardness, and an amount of a raw material inorganic particle to be used, an amount of an aqueous solvent to be added, and a kind of a grinding machine, but they can be appropriately selected including grinding conditions, depending upon a necessary average particle size of an inorganic fine particle. In another process for producing an inorganic fine particle having an average particle size of 0.01~5 μm, the particle can be obtained by wet-dispersing an inorganic fineparticle aggregate in which a primary particle is 0.01~5 μm, in the presence of an aqueous medium. A wet-dispersion does not need special process but can be performed by a process which is generally used in the art. For example, an inorganic fine particle may be dispersed using a wet-dispersing machine such as a dissolver, a homogenizer and the like in the presence an aqueous medium. The dispersion conditions are different depending upon a size, a hardness and a used amount of an aggregated inorganic fine particle, an amount of an aqueous solvent to be added, and a kind of a dispersing machine and the like, but the dispersing conditions such as a dispersion time, a stirring equipment, a rotating number and the like can be appropriately selected depending upon a necessary average particle size of an inorganic fine particle.

A polyorganosiloxane film is formed on the surface of the resulting inorganic fine particle as follows: At a point when the particle is ground or dispersed to the desired average particle size, a silane compound represented by the general formula (I):

(I)

wherein Z is RO— or OCN—, X is halogen, Y is —OH, R is an organic group having a carbon number of 8 or less, and n, m and L are an integer of 0~ to 4, provided that n+m+L=4, and/or a low co-condensate of the silane compound and an organosilane compound represented by the general formula (II):

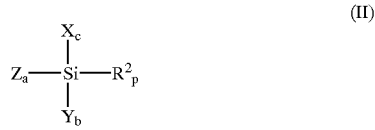

(II)

wherein Z is $R^1O$— or OCN—, X is halogen, Y is —OH, $R^1$ is an organic group having a carbon number of 8 or less, $R^2$ is an organic group, p is an integer of 1~ to 3, and a, b and c are all an integer of 0~ to 3, provided that a+b+c+p=4, and/or a low-condensate of the organosilane compound are present in an aqueous dispersion containing the resulting inorganic fine particle, and hydrolysis and partial hydrolysis are performed in this system to co-condense them to form a polyorganosloxane film via a silanol compound. Alternatively, a silane compound represented by the general formula (I) and/or a low-condensate of the silane compound and an organosilane compound represented by the general formula (II) and/or a low condensate of the organosilane compound are hydrolyzed or partially hydrolyzed in the presence of a metal compound to co-condense them to form a film via a silanol compound. Thereby, the system becomes the state where an inorganic fine particle having an average particle size of 0.01~5 μm is finely dispersed without association in an aqueous dispersion in which a condensed organosilane compound, that is, polyorganosiloxane is dispersed.

The form of a compound to be added to an aqueous dispersion for forming the aforementioned polyorganosiloxane film is not particularly limited but any form of a monomer, a low-(co-)condensate (oligomer) obtained by partially hydrolyzing a monomer, and a mixture thereof may be used.

A process of addition to an aqueous dispersion is not particularly limited, but compounds to be added may be added separately or simultaneously or intermittently by pre-mixing, and may be added in one portion or intermittently in a divided manner. However, in order to enhance the uniformity of addition, a process of diluting a compound to be added using an organic solvent miscible with an aqueous dispersion and adding intermittently in a divided manner is preferable.

In addition, when a low co-condensate (oligomer) is used for forming a polyorganosiloxane film, its shape is not particularly limited, but a linear shape is more preferable than three dimensional shape. When a degree of polymerization is too large, a co-condensation reactivity to the surface of an inorganic fine particle is inferior and the state of formation of a polyorganosiloxane film becomes worse in some cases.

In addition, as another process for forming a polyorganosiloxane film, there is a process of preparing a solution containing a precursor of the aforementioned polyorganosiloxane film in advance, and mixing an aqueous dispersion containing the resulting inorganic fine particle into the solution to form a film in the state of uniform dispersion, being not limiting.

Z in the general formula (I) and the general formula (II) represents RO group, $R^1O$ group or OCN group which can generate a silanol group by hydrolysis, X represents halogen, and Y represents OH group. R and $R^1$ are an organic group having a carbon number of 8 or less and, more particularly, there can exemplified alkyl group or alkyl derivative such as methyl, ethyl, 2-chloroethyl, alkyl, aminoethyl, propyl, isopentyl, hexyl, 2-methoxyethyl, phenyl, m-nitrophenyl, 2,4-dichlorophenyl and the like. From a viewpoint of a rate of hydrolysis and discoloration due to remaining carbon in a polyorganosiloxane film, methyl and ethyl are preferable. In addition, as a halogen, there are chlorine and bromine, and chlorine is preferable.

In addition, $R^2$ in the general formula (II) is not particularly limited as long as it is an organic group, but a shorter main chain of an organic group is preferable in that the structural strength of a polyorganosiloxane film can be maintained.

As an example of a silane compound represented by the general formula (I), there are tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide (silicon oxide hydrate), tetraisocyanatosilane, ethoxysilane triisocyanate and the like. Among them, tetramethoxysilane and tetraethoxysilane are preferable.

In addition, it is more preferable to be a low-condensate of a silane compound represented by the general formula (I), more particularly, a low-condensate obtained by partially hydrolyzing and condensing a tetramethoxysilane or tetraethoxysilane compound. These silane compounds can be used alone or in combination of two or more of them.

As an example of an organosilane compound represented by the general formula (It), there are methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltriethoxysilane, 3-aminopropyltriethoxysilane, methyltrichlorosilane, phenyltrichlorosilane, trimethylsilylisocyanate, vinylsilyltriisocyanate, phenylsilyltriisocyanate and the like. Alternatively, low-condensates of these organosilane compounds may be used.

Among those organosilane compounds, vinyltrimethoxysilane, vinyltriethoxysilane, vinyltrichlorosilane, vinyl(β-methoxyethoxy)silane, γ-methacryloyloxypropyltrimethoxysilane, γ-glycidoxypropyltrimethoxysilane, γ-mercaptopropyltrimethoxysilane, γ-aminopropyltrimethoxysilane and the like are preferable, and γ-methacryloyloxypropyltrimethoxysilane is more preferable. These organosilane compounds may be used alone or in combination of two or more of them.

In addition, as a metal compound, there can be used, without any limitation, a metal compound which alone is hydrolyzed or partially hydrolyzed and condensed to form a skeleton of a polyorganosiloxane film, and a metal compound which makes a modificatory contribution to a skeleton in the presence of another compound forming a skeleton of a polyorganosiloxane film. As an example of those metal compounds, there are metal halide, metal nitrate, metal sulfate, metal ammonium salt, organometal compound, alkoxy metal compound and derivatives of these metal compounds. The metal compounds may be used alone or in combination of two or more of them. As metal elements which constitute these compounds, there are respective elements of Periodic Table Group I~Group V. Among these metal compounds, metal compounds are preferable which comprise metal elements of Periodic Tables Group III–Group V which can alone be hydrolyzed and condensed to form a three dimensional skeleton. Metal compounds comprising Zr or Ti are more preferable. When a modified filler of the present invention obtained by forming polyorganosiloxane in the presence of a metal compound comprising these two kinds of metal elements are used as a filler for a dental composition, the radiopacity can be imparted to the composition. As a metal compound comprising Zr or Ti, there can be exemplified titanium tetrachloride, titanyl sulfate, methyltrichlorotitanium, dimethyldichlorotitanium, tetramethoxytitanium, tetraethoxytitanium, tetraisopropoxytitanium, tetraisobutoxytitanium, tetrakis(2-ethylhexyloxy)titanium, diethoxydibutoxytitanium, isopropoxytitanium trioctarate, diisopropoxytitanium diacrylate, tributoxytitanium stearate, zirconium tetrachloride, zirconium oxychloride, zirconium acetate, zirconium lactate, tetramethoxyzirconium, tetraethoxyzirconium, tetraisopropoxyzirconium, tetrabutoxyzirconium and the like. Alternatively, derivatives of the aforementioned metal compounds may be used. As a derivative of a metal compound, there can be exemplified a metal compound in which a part of a hydrolyzable group such as halogen, $NO_3$, $SO_4$ alkoxy group, acyloxy group and the like is substituted with a group which can form a chelating compound such as dicarboxylic acid group, oxycarboxylic acid group, β-diketone group, β-ketoester group, β-diester group, alkanolamine group and the like. Alternatively, a low-condensed metal compound (oligomer or polymer) obtained by partially hydrolyzing and low-condensing a metal compound may be used.

Hydrolysis or partial hydrolysis of a compound added to the aforementioned aqueous dispersion is performed under stirring at a relatively low speed. A stirring temperature is in a range of 10 C to 100 C, more preferably in a range of 25 C to 50 C and there is no limitation as long as it is a temperature below a boiling point of an aqueous medium. A stirring time is in a range of a few minutes to a few hours, more preferably in a range of 30 minutes to 24 hours, and can be adjusted by a kind and an amount of a compound to be added, a kind, an average particle size of an inorganic fine particle and a proportion of an inorganic fine particle occupied in its aqueous dispersion, a kind of an inorganic fine particle and a proportion of an aqueous medium occupied in its aqueous dispersion and the like. Stirring does not need a special process but can be performed by adopting an equipment normally employed in the art. For example, stirring may be performed using a stirring machine which can stir a slurry such as a universal mixer, a planetary mixer and the like.

In addition, in order to control a rate of hydrolysis or partial hydrolysis and co-condensation, a sol-gel catalyst such as an acid, an alkali, an organometal compound, a metal alkoxide, a metal chelating compound and the like is preferably added. As an embodiment of a catalyst, there are an inorganic acid such as hydrochloric acid, acetic acid, nitric acid, formic acid, sulfuric acid, phosphoric acid and the like, an organic acid such as para-toluenesulfonic acid, benzoic acid, phthalic acid, maleic acid and the like, an alkali catalyst such as potassium hydroxide, sodium hydroxide, ammonia and the like. In addition, as an aqueous medium used in a step of forming a polyorganosiloxane film, water and/or an organic solvent miscible with water can be used without any limitation. Particularly preferably, an aqueous solvent can be appropriately selected from alcohols, ketones and ethers. These solvents have the great effects that they not only improve misciblity of a variety of compounds used in a step of forming polyorganosiloxane but also decrease the aggregability of particles in a heat-treating step and improve the disintegrability. As an embodiment of these solvents, there are alcohols such as ethyl alcohol, n-propyl alcohol, isopropyl alcohol, t-butyl alcohol, isobutyl alcohol and the like, ethers such as tetrahydrofuran, dioxane and the like, and ketones such as acetone and the like. These solvents may be used alone or in combination of two or more of them. Preferably, ethyl alcohol, n-propyl alcohol and isopropylalcohol are suitably used.

An amount of a silane compound and that of an organosilane compound to be added are not particularly limited, but can be appropriately selected depending upon a processes of forming a film, and a kind and an average particle size of an inorganic fine particle, and is in a range of 0.1 to 20 parts by weight in terms of $SiO_2$ amount (a total amount of a silane compound and an organosilane compound) relative to 100 parts by weight of an inorganic fine particle. Preferably, the amount is in a range of 0.1 to 10 parts by weight, more preferably in a range of 0.1 to 5 parts by weight. In addition, a ratio of a silane compound and an organosilane compound present in a polyorganosiloxane film is 99:1~20:80, preferably 99:1~30:70, more preferably 99:1~40:60, in terms of $SiO_2$ amount by weight.

In addition, when a polyorganosiloxane film is formed in the presence of a metal compound, a metal compound can be present in a range of 0.1~500 parts by weight, more preferably 0.1~200 parts by weight in terms of metal oxide amount relative to 100 parts by weight in terms of $SiO_2$ amount.

Further, in the step of forming polyorganosiloxane film, as mentioned above, a catalyst may be added to the aqueous medium, and the amount to be added is preferably 0~10.0 parts by weight, more preferably 0~5.0 parts by weight relative to 100 parts by weight of the compound to be added.

Next, a system in such the state is heat-treated and an aqueous medium is removed to solidify from an aqueous dispersion. Heat-treatment consists of two stages of aging and sintering, and the former is aimed at growing a polyorganosiloxane film and the latter is aimed at structural strengthening. The former needs to be performed by allowing to stand, so as not to impart distortion to the film structure and to remove an aqueous medium, and a equipment such as a box-type heat dryer and the like are preferable. An aging temperature is a range of room temperature to 100 C, more preferably in a range of 40 C~80 C. When the temperature is below this range, removed of an aqueous medium is insufficient. When the temperature is above this range, rapid volatilization is caused, and there is a possibility that a defect is produced in a polyorganosiloxane film, and peeling from the surface of an inorganic particle is caused. Since an aging time depends upon the ability of a dryer, it is not limited as long as it is a time for sufficiently removing an aqueous medium. On the other hand, a sintering step consists of temperature rising and holding. In the former, it is better to gradually raise a temperature to a goal temperature for a longer period of time. Rapid temperature rising is not preferable because distortion is produced in a polyorganosiloxane film. The latter is a sintering at a constant temperature and its time is 10 hours to 100 hours, more preferably 10 hours to 50 hours. A sintering temperature is in a range of 100~350 C, more preferably 100~200 C. This temperature must be appropriately selected to an extent that does not render a porous polyorganosiloxane film nonporous. After an aqueous medium was removed by heat-treatment as described above, a shrank and solidified material was obtained. Although a solidified material is in the state of aggregation of an inorganic fine particle, it is not a mere aggregate of inorganic fine particles but a polyorganosiloxane film formed by co-condensation intervenes, on a boundary plane of an individual fine particle. Therefore, when this solidified material is disintegrated, to an extent of an inorganic fine particle before formation of a polyorganosiloxane film, an individual inorganic fine particle having the surface covered with polyorganosiloxane, that is, a modified filler of the present invention is obtained. As used herein, the term "disintegrated to an extent of an inorganic fine particle before formation of a polyorganosiloxane film" refers to disintegration to inorganic fine particles. The different point from the original inorganic fine particles is that an individual inorganic fine particle is covered with polyorganosiloxane. However, a secondary aggregate may be contained to a non-problematic extent. Disintegration can be easily performed by applying a shearing force or an impact force and, for example, disintegration can be performed using a Henschel mixer, a cross rotary mixer, a supermixer or the like.

The modified filler of the present invention thus obtained has an average particle size of 0.01~5 $\mu$m and the surface thereof is covered with polyorganosiloxane. An average particle size and particle size distribution can be confirmed by a laser diffraction particle size measuring machine. As a result, it is recognized that a modified filler of the present invention is powdered in the uniform dispersion state because it has the same average particle size and monodisperse particle size distribution as those in the state where inorganic fine particles are dispersed uniformly. On the other hand, an average particle size of an inorganic fine particle which is not covered with polyorganosiloxane is shifted to a larger side and polydispersed particle size distribution is shown due to the presence of an aggregate. Alternatively, these dispersion states can be confirmed by observation with an electron microscope. In addition, a specific surface area of a modified filler of the present invention can be measured by BET method and it is recognized that a specific surface area of the modified filler is increased due to formation of a polyorganosiloxane film. In addition, although a large number of OH groups are present on the film surface, the fluidity and the dispersibility of a filler are better. This is considered to be resulted from the fact that contact between fine particles is point contact due to the irregular parts of the film surface. The thickness of a polyorganosiloxane film is influenced by an amount of a silane compound and that of an organosiloxane compound to be added and is 500 $\mu$m or less, more preferably 100 $\mu$m or less. In addition, when this modified filler is used in a dental composition, a resin component is penetrated into the irregular parts of the surface of a polyorganosiloxane film and it is recognized that the mechanical properties are improved by the fitting effect. And at the same time, it is recognized that the polishability is improved. In addition, in order to pack this modified filler at a large amount, it is effective to further treat a polyorganosiloxane film with an organosilane compound represented by the general formula (II):

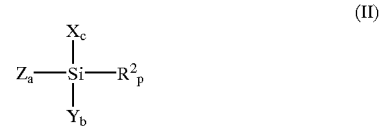

(II)

wherein Z is $R^1O$— or OCN—, X is halogen, Y is —OH, $R^1$ is an organic group having a carbon number of 8 or less, $R^2$ is an organic group, p is an integer of 1~ to 3, and a, b and c are all an integer of 0~ to 3, provided that a+b+c+p=4. As a result, packing at a large amount becomes possible and various properties necessary as a dental composition can be satisfied.

Among the aforementioned organosilane compounds, a silane coupling agent which is known in the dental field is effective and examples thereof are vinyltrimethoxysilane, vinyltriethoxysilane, vinyltrichlorosilane, vinyltri($\beta$-methoxyethoxy)silane, $\gamma$-methacryloyloxypropyltrimethoxysilane, $\gamma$-glycidoxypropyltrimethoxysilane, $\gamma$-mercaptopropyltrimethoxysilane, $\gamma$-aminopropyltriethoxysilane and the like. $\gamma$-methacryloyloxypropyltrimethoxysilane is more preferable. These organosilane compounds can be used alone or a plurality of them can be used.

The affinity with a resin component is enhanced by these organosilane compounds because the surface of an organosilane compound is effectively and uniformly treated by a reaction with a large number of OH groups present on a polyorganosiloxane film.

Another aspect of the present invention is a dental composition containing the aforementioned modified filler of the present invention, in particular, a dental composition containing (a) a modified filler of the present invention, (b) a polymerizable monomer and (c) a polymerization initiator.

A modified filler of the present invention has the characteristics that it can be uniformly dispersed in a composition in the non-aggregated state due to the presence of a polyorganosiloxane harbored on its surface and at the same time a cured composition manifests the excellent physical properties due to the high affinity with an organic matrix. Further, a cured dental composition containing a modified filler of the present invention as a filler can afford the original excellent glossiness after polishing due to fineness of a filler and, additionally, it has the excellent wear resistance in spite of such the fine filler. It is considered that this excellent wear resistance is imparted by a filler having interaction with a matrix with the strong affinity by an action of a polyorganosiloxane film present on the surface of a modified filler and an organosilane compound which is added upon dispersion into a matrix, and the fitting effect of a matrix penetrated into a polyorganosiloxane film.

A polymerizable monomer which can be used in a dental composition together with a modified filler of the present invention, an organic compound filler, a modified filler and a coloring filler, can be used by selecting from the known monofunctional and multifunctional polymerizable monomers which are generally used as a dental composition.

Representative examples which are generally used suitably are polymerizable monomers having an acryloyl group and/or a methacryloyl group. In the present invention, (meth)acrylate or (meth)acryloyl represented inclusively both acryloyl group-containing polymerizable monomers and methacryloyl group-containing polymerizable monomers.

Embodiments thereof are as follows:

As polymerizable monomers having no acidic group, monofunctional monomer: (meth)acrylic acid esters such as methyl(meth)acrylate, ethyl (meth)acrylate, butyl(meth)acrylate, hexyl(meth)acrylate, tetrahydrofurfuryl (meth) acrylate, 2-hydroxyethyl(meth)acrylate, grycidyl(meth)acrylate, lauryl(meth)acrylate, cyclohexyl(meth)acrylate, allyl(meth)acrylate, 2-ethoxyethyl(meth)acrylate, methoxy polyethylene glycol(meth)acrylate, glycerol(meth)acrylate, isobonyl(meth)acrylate and the like, silane compounds such as γ-(meth)acryloyloxypropyltrimethoxysilane, γ-(meth)acryloyloxypropyltriethoxysilane and the like, nitrogen-containing compounds such as 2-(N,N-dimethylamino)ethyl (meth)acrylate, N-methylol(meth)acrylamide, diacetone (meth)acrylamide and the like, Aromatic Bifunctional Monomer:
2,2-bis(4-(meth)acryloyloxyphenyl)propane,
2,2-bis(4-(3-(meth)acryloyloxy-2-hydroxypropoxy)phenyl)propane,
2,2-bis(4-(meth)acryloyloxyethoxyphenyl)propane,
2,2-bis(4-(meth)acryloyloxydiethoxyphenyl)propane,
2,2-bis(4-(meth)acryloyloxytetraethoxyphenyl)propane,
2,2-bis(4-(meth)acryloyloxypentathoxyphenyl)propane,
2,2-bis(4-(meth)acryloyloxydipropoxyphenyl)propane,
2,2-bis(4-(meth)acryloyloxyethoxyphenyl)-2-(4-(meth)acryloyloxydiethoxyphenyl)propane,
2-(4-(meth)acryloyloxydiethoxyphenyl)-2-(4-(meth)acryloyloxytriethoxyphenyl)propane,
2-(4-(meth)acryloyloxydipropoxyphenyl)-2-(4-(meth)acryloyloxytriethoxyphenyl)propane,
2,2-bis(4-(meth)acryloyloxypropoxyphenyl)propane,
2,2-bis(4-(meth)acryloyloxyisopropoxyphenyl)propane and the like, Aliphatic Bifunctional Monomer:
2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol(meth)acrylate, 1,6-hexanediol (meth)acrylate, glycerin di(meth)acrylate and the like, trifunctional monomer:
trimethylolpropane tri(meth)acrylate, treimethylolethane tri(meth)acrylate, trimethylolmethane tri(meth)acrylate, pentaerythritol tri(meth)acrylate and the like, Tetrafunctional Monomer:
pentaerythritol tetra(meth)acrylate, ditrimethylolporpane tetra(meth)acrylate and the like.

In addition, embodiments of an urethane system polymerizable monomer are di(meth)acrylates having a bifunctiorial or trifunctional or more-functional urethane linkage which are derived from an adduct of a polymerizable monomer having a hydroxy group such as 2-hydroxyethyl(meth)acrylate, 2-hydroxypropyl(meth)acrylate and 3-chloro-2-hydroxypropyl(meth)acrylate and a diisocyanate compound such as methylcyclohexane diisocyanate, methylene bis(4-cyclohexyl isocyanate), isophorone diisocyanate, diisocyanate methylbenzene and, 4,4-diphenylmethane diisocyanate.

In addition to the aforementioned (meth)acrylate system polymerizable monomers, other polymerizable monomers, for example, a monomer, an oligomer or a polymer having at least one polymerizable group in the molecule may be used depending upon the purpose of a dental composition without any limitation. In addition, there is no problem that the polymerizable monomers have a substituent such as an acidic group, a fluoro group and the like.

In the present invention, a polymerizable monomer includes not only a single component but also a mixture of a plurality of polymerizable monomers.

In addition, when a polymerizable monomer has the extremely high viscosity at room temperature or when a polymerizable monomer is a solid at room temperature, it is preferably used as a mixture of polymerizable monomers by combining with a polymerizable monomer having the low viscosity. This combination may comprise not only two kinds but also three kinds or more.

In addition, since a polymer comprising only monofunctional polymerizable monomers has no cross-linking structure, it generally has a tendency to be inferior in the mechanical strength of a polymer.

For that reason, when a polymerizable monomer is used, it is preferable that it is used with a polyfunctional polymerizable monomer. The most preferable combination of polymerizable monomers is a manner of combining an aromatic compound of a bifunctional polymerizable monomer as a main component with an aliphatic compound of a bifunctional polymerizable monomer.

More particularly, there is a combination of 2,2-bis(4-(3-methacryloyloxy-2-hydroxypropoxy)phenyl)propane (Bis-GMA) and triethylene glycol dimethacrylate (TEGDMA).

When a teeth substance and a nonprecious metal adhering property is imparted to a dental composition containing a modified filler of the present invention, it is effective to use a polymerizable monomer containing an acid group such as a phosphoric acid group, a carboxylic acid group, a sulfonic acid group or the like in the molecule as a part or the whole of a polymerizable monomer.

In addition, in order to enhance a precious metal adhering property, it is also effective to the present invention to use those polymerizable monomers containing a sulfur atom in the molecule. Embodiments of these polymerizable monomers having the adhering ability are as follows:

Carboxylic acid group-containing polymerizable monomer:

(meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 2-(meth)acryroyloxybenzoic acid, β-(meth)acryroyloxyethyl hydrogen succinate, β-(meth)acryroyloxyethyl hydrogen maleate, 11-(meth)acryloyloxy-1,1-undecanedicarboxylic acid, p-vinylbenzoic acid and the like, Phosphate Group-containing Monomer:

2-(meth)acryloyloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl)hydrogen phosphate, 2-(meth)acryloyloxyphenyl hydrogen phosphate and the like, Sulfonic Group-containing Monomer:

2-(meth)acrylamide-2-methylpropanesulfonic acid, 4-(meth)acryloyloxybenzenesulfonic acid, 3-(meth)acryloyloxypropanesulfonic acid and the like, Sulfur Atom-containing Monomer:

(meth)acrylate having a triazinethiol group, (meth)acrylate having a mercapto group, (meth)acrylate having a polysulfide group, (meth)acrylate having a thiophosphate group, (meth)acrylate having a disulfide group, (meth)acrylate having a mercaptodithiazole group, (meth)acrylate having a thiouracil group, (meth)acrylate having a thiirane group and the like.

These polymerizable monomers are used alone or as a mixture of two or more without any problem.

A polymerization initiator which can be used with a modified filler of the present invention in a dental composition is not particularly limited and the known radical generator can be used without any limitation.

Polymerization initiators are generally classified into initiators which initiate polymerization by mixing prior to use (chemical polymerization initiator), initiators which initiate polymerization by heating or warming (thermal polymerization initiator, and initiators which initiate polymerization by light irradiation (photoinitiators).

As a chemical polymerizable initiator, there are polymerizable initiator systems of a redox type comprising an organic peroxide/an amine compound or an organic peroxide/an amine compound/a sulfinic acid salt, or an organic peroxide/an amine compound/a borate compound, and organometal type initiator system which initiates polymerization by a reaction with oxygen or water. Further, sulfinic acid salts and borate compounds can also initiate polymerization by a reaction with a polymerizable monomer having an acidic group.

Embodiments of the aforementioned organic peroxide are benzoylperoxide, parachlorobenzoylperoxide, 2,4-dichlorobenzoyl peroxide, 2,5-dihydroperoxy-2,5-dimethylhexane, methyl ethyl ketone peroxide, tertiary-butyl peroxide benzoate and the like.

As the aforementioned amine compound, a secondary or tertiary amine in which an amine group is bound to an aryl group is preferable and embodiments thereof are p-N,N-dimethyltoluidine, N,N-dimethylaniline, N-β-hydroxyethylamine, N,N-di(β-hydroxyethyl)aniline, p-N,N-di(β-hydroxyethyl)toluidine, N-methylaniline, p-N-methyltoluidine and the like.

Embodiments of the aforementioned sulfmic acid salt are sodium benzenesulfinate, lithium benzenesulfinate, sodiump-toluenesulfinate and the like.

As the aforementioned borate compound, there are trialkylphenylboron, and sodium salt, lithium salt, potassium salt, magnesium salt, tetrabutyl ammonium salt, tetramethyl ammonium salt of trialkyl(p-fluorophenyl)boron (wherein alkyl group is n-butyl group, n-octyl group, n-dodecyl group or the like). In addition, as the aforementioned organometal type polymerizable initiator, there are organic boron compounds such as triphenylborane, tributylborane, partial oxide of tributylborane and the like. In addition, as a thermal polymerization initiator by heating or warming, azo compounds such as azobisisobutyronitrile, methyl azobisisobutyrate, azobiscyano valeric acid and the like ate suitably used.

On the other hand, as a photoinitiator, there are a photoinitiator comprising a photosensitizer, a photosensitizer/a photopolymerization promotor and like.

Embodiments of the aforementioned photosensitizer are α-diketones such as benzil, camphorquinone, α-naphtil, acetonaphtone, p,p'-dimethoxybenzil, pentandione, 1,2-phenanthrenquinone, 1,4-phenanthrenquinone, 3,4-phenanthrenquinone, 9,10-phenanthrenquinone, naphthoquinone and the like benzoin alkyl ethers such as benzoin, benzoin methyl ether, benzoin ethyl ether and the like, thioxanthones such as thioxanthone, 2-chlorothioxanthone, 2-methylthioxanthone, 2-hydroxythioxanthone, 2,4-diethylthioxanthone, 2,4-diisopropylthioxanthone and the like, benzophenones such as benzophenone, p-chlorobenzophenone, p-methoxybenzophenone and the like, acylphosphineoxides such as 2,4,6-trimethylbenzoyl diphenylphosphineoxide, bis(2,6-dimethoxybenzoyl)-2,4,4-trimethylpentylphosphineoxide and the like, α-aminoacetophenones such as 2-benzyldimethylamino-1-(4-morpholinophenyl)butanone-1,2-benzyl-diethylamin o-1-(4-morpholinophenyl)propanone-1 and the like, ketals such as benzyldimethylketal, benzyldiethylketal, benzyl(2-methoxyethylketal) and the like, titanocenes such as bis (cyclopentadienyl)-bis[2,6-difluoro-3-(1-pyrolyl)phenyl] titanium, bis(cyclopentadienyl)-bis(pentanefluorophenyl) titanium, bis(cyclopentadienyl)-bis(2,3,5,6-tetrafluoro-4-disiloxyphenyl)-titanium and the like.

Embodiments of the aforementioned photopolymerization promoters are tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 2-dimethylaminopyridine, N,N- dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, 2,2'-(n-butylimino)diethanol and the like, secondary amines such as N-phenylglycine and the like, barbituric acid such as 5-butylbarbituric acid, 1-benzyl-5-phenylbarbituric acid and the like, tin compounds such as dibutyltin diacetate, dibutyltin dilaurate, dioctyltin dilaurate, dioctyltin diperacetate, dioctyltin bis(mercaptoacetic acid isooctyl ester) salt, tetramethyl-1,3-diacetoxydistannoxane and the like, aldehyde compounds such as laurylaldehyde, terephthalaldehyde and the like, sulfur-containing compounds such as dodecylmercaptan, 2-mercaptobenzoxazole, 1-decanethiol, thiosalicylic acid and the like.

In addition, for improving the photopolymerization promoting ability, the additions of oxycarboxylic acids such as citric acid, maleic acid, tartaric acid, glycolic acid, gluconic acid, α-oxyisobutyric acid, 2-hydroxypropioic acid, 3-hydroxybutanoic acid, 4-hydroxybutanoic acid, dimethylolpropioic acid and the like is effective besides the additions of the aforementioned photopolymerization promoters.

Those polymerization initiators may be used alone or as a mixture of two or more of them. In addition, they can be used in a combination irrespective of a polymerization form and a kind of a polymerization initiator.

An amount of a polymerization initiator to be added may be appropriately selected depending upon the use. In general, the amount may be selected from a range of 0.1~10 parts by weight relative to a polymerizable monomer.

Among the aforementioned polymerization initiators, it is preferable to use a photopolymerization initiator which generates a radical by light irradiation and such the initiator is most suitably used in that a dental composition can be polymerized in the state where an air is mixed therein at a small amount. In addition, among photopolymerization initiators, a combination of α-diketone and tertiary amine is preferable and a combination of camphorquinone with an aromatic amine having an amino group directly bound to a benzene ring such as ethyl p-N,N-dimethylaminobenzoate and the like or an aliphatic amine having a double bond in the molecule such as N,N-dimethylaminoethyl methacrylate is most preferable.

In addition, sensitizing pigments such as coumarin, cyanine, thiazine and the like, a light acid generator which produces Bronsted acid or Lewis acid by light irradiator such as a s-triazine derivative substituted which a halomethyl group, diphenyl iodonium salt compound and the like, quaternary ammonium halides, transition metal compound are also suitably used depending upon the use.

Another filler which can be used in a dental composition in combination with modified fillers of the present invention is not particularly limited, but the known filler, for example, an inorganic filler and/or an organic filler and/or an organic-inorganic compound filler, can be used without any limitation. A shape of such a filler is not particularly limited, but particle shapes such as of sphere, needle, plate, crushed and flake may be taken. Also, a kind of the filler is not particularly limited.

Examples of an inorganic filler include quartz, amorphous silica, aluminium silicate, aluminium oxide, titanium oxide, zirconium oxide, various glasses (including a glass prepared by a melting process, a synthetic glass prepared by a sol-gel process, a glass produced by a vapor phase process), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite and the like. Among them, preferred are an aluminosilicate glass, a borosilicate glass, an aluminoborate glass, a boroaluminosilicate glass and the like, which contain heavy metals such as sodium, strontium, barium and lanthanum and/or fluoride. An average particle size of the inorganic filler is not particularly limited, but it is preferably in a range of 0~10 μm, and more preferably in a range of 0~5 μm.

In addition, ultrafine particle inorganic fillers such as Aerosil produced by a vapor phase process or a particle of silica-zirconia oxide produced from a solution by a sol-gel process can be used. In addition, an aggregated inorganic filler in which such the ultrafine particle is aggregated may be used without anyproblem.

In addition, an organic filler can be prepared by polymerizing a monomer having a polymerizable group, and a kind thereof is not particularly limited. Examples of an organic filler include fillers prepared by (co)polymerizing a polymerizable monomer, alone or in combination, such as unsaturated aromatic compounds such as styrene, α-methylstyrene, halogenated styrene and divinylbenzene; unsaturated esters such as vinyl acetate and vinyl propionate; unsaturated nitrites such as acrylonitrile; and butadiene and isoprene. Particularly preferred is a filler prepared by polymerizing the above polymerizable monomer which is known in the dental field. A process for producing an organic filler is also not particularly limited, but processes such as emulsion polymerization, suspension polymerization and dispersion polymerization, or a process of grinding a preformed polymer bulk can be employed.

Alternatively, an organic-inorganic compound filler containing an inorganic particle in an organic polymer can be used. An inorganic particle to be contained in an organic polymer is not particularly limited, but the known inorganic particle, for example, the aforementioned inorganic filler can be contained. A process for producing an organic-inorganic compound filler is also not particularly limited, but any process can be adopted. Examples of such the process include a process for micro-encapsulating an inorganic particle with an organic material or grafting the surface of an inorganic particle with an organic material, a process for radical-polymerizing a polymerizable functional group or a polymerizable initiation group on the surface of an inorganic particle after introducing it to the surface, a process for grinding a polymer bulk containing inorganic particles which have been produced in advance, and the like.

An average particle size of an organic or organic-inorganic compound filler is preferably in a range of 1~100 μm, more preferably in a range of 3~50 μm, and most preferably within a range of 5~30 μm. These inorganic, organic and organic-inorganic compound fillers can be used alone or in combination thereof.

Fillers such as inorganic, organic and organic-inorganic compound fillers can be used for a dental composition, after the surface of a particle thereof is treated with, for example, surfactants, fatty acids, organic acids, inorganic acids, silane coupling agents, titanate coupling agents, polysiloxane or the like. These surface treating processes are preferable in that these can enhance the wettability between a resin component and the filler surface and can impart various excellent properties to a dental composition, and these can be arbitrarily selected depending upon the required properties. Moreover, in order to multi-functionalize these fillers, surface treatment with special surface treating agents and/or by a special process of surface treatment can be conducted without any limitation.

A proportion of such the filler in a dental composition may be optionally selected depending upon material property required for a dental composition.

An filling amount of low-viscous materials such as sealants, bonding materials, primers, tooth surface treating agents, opacifying agents and cements generally used in the dental field should be set at a relatively small level since higher fluidity required as material property is required for these materials. Therefore, the amount is preferably in a range of 5.0~80.0 parts by weight, more preferably in a range of 30.0~70.0 parts by weight relative to the whole component of a dental composition.

In addition, an filling amount of high-viscous materials such as a composite resin and a beneer crown resin should be set at a relatively high level since, as the required material property, such the shapability is required that does not cause deformation after shape adjustment. Accordingly, the amount is preferably in a range of 50.0~98.0 parts by weight, more preferably in a range of 75.0~98.0 parts by weight relative to the whole component of a dental composition.

In addition, if needed, components such as ultraviolet absorbing agents such as 2-hydroxy-4-methylbenzophenone, polymerization inhibitors such as hydroquinone, hydroquinone monomethyl ether and 2,5-di (tertiary-butyl)-4-methylphenol, anti-discoloring agents, antimicrobial agents, and other conventional known additives may be optionally added to a dental composition.

A packing type of the dental composition of the present invention is not particularly limited, but it may be any one of one-package type, two-package type and the like depending upon a kind of a polymerization initiator or a purpose of use, and it may be appropriately selected depending upon the application.

The coloring filler of the fifth aspect of the present invention is a filler in which an inorganic particle and a coloring particle are mixed and dispersed uniformly, and the surfaces of these particles are covered with poly(organo) siloxane. A kind of an inorganic particle which can be used in the present coloring filler is not particularly limited, but any kinds of inorganic particles can be used without any limitation. Specifically, such inorganic particles includes, for example, quartz, amorphous silica, aluminium silicate, aluminium oxide, titanium oxide, zirconium oxide, various glasses (including a glass by a melting process, and a synthesized glass made by a sol-gel process), calcium carbonate, talc, kaolin, clay, mica, aluminium sulfate, calcium sulfate, barium sulfate, calcium phosphate, hydroxyapatite, silicon nitride, aluminium nitride, titanium nitride, silica carbide, boron carbide, calcium hydroxide, strontium hydroxide, zeolite, but is not limited to them. Preferred are glasses such as an aluminosilicate glass, a borosilicate glass, an aluminoborate glass, a boroaluminosilicate glass comprising a heavy metal such as sodium, strontium, barium, lanthanum and/or fluoride. In addition, inorganic superfine particles may be used, for example, Aerosil formed by a vapor phase process or a silica-zirconia oxide particle formed from a solution for a sol-gel reaction and the like. Further, for example, aggregated inorganic particle in which these ultrafine particles are aggregated can be used without any problems. These inorganic particles may be used alone or in combination of two or more of them. The shape of these inorganic particles is not particularly limited, but any arbitrary particle shapes such as spherical, needle, plate, crushed, or flake may be used without any limitation. Further, there is no particular limitation in an average particle size of these inorganic particles, but a preferred range is 0.01~50 μm, and a more preferred range is 0.01~30 μm. A most preferred range is 0.01~5.0 μm.

Further, as far as the properties of the coloring filler are not deteriorated, in addition to the inorganic particle, an organic particle and/or an organic-inorganic compound particle can be contained without no limitation.

As the inorganic fine particle used in the present invention, a conmmercially available raw inorganic particle, which is generally used as a filler material, may be used without any processing. In addition, when a desired average particle size is required, it can be obtained by grinding. Grinding does not require a specific process, but it may be performed by adopting a process commonly used in the art, whether a wet process or a dry process. Examples are a high-speed rotation mill such as a hammer mill and a turbo mill, a container-driven medium mill such as a ball mill and a oscillating mill, a grinding medium agitaing mill such as a sand grinder and an attritor, and a jet mill and the like, and they can be appropriately selected depending upon the desired average particle size of the inorganic particle. In order to obtain an inorganic particle having a small average particle size, a wet-grinding in an aqueous medium is a preferred mode. As the aqueous medium used in this case, water may be used alone or in combination of alcohols, ethers, ketones and the like which are miscible with water. Although the conditions for the wet-grinding vary depending upon a size, a hardness or an amount of an inorganic particle to be added and a kind and an amount of an aqueous medium to be added, the conditions, including grinding conditions may be appropriately selected depending upon the required average particle size of the inorganic particle.

A kind of a coloring particle which can be used in the present coloring filler is not particularly limited, but an inorganic pigment and/or an organic pigment can be used depending upon the intended color tone of a coloring filler without any limitation. The shape of the coloring particle is not particularly limited, but any arbitrary shapes such as spherical, needle, plate, crushed or flake can be used without any limitation. Specifically, the inorganic pigments include, for example, chromates such as chrome yellow, zinc yellow, barium yellow; fepnocyanides such as Prussian blue; sulfides such as vermilion, cadmium yellow, zinc sulfide, antimony white, cadmium red; sulfates such as barium sulfate, zinc sulfate and strontium sulfate; oxides such as zinc white, titanium white, blood red, black iron oxide, chromium oxide; hydroxides such as aluminium hydroxide; silicates such as calcium silicate, ultramarine; carbons such as carbon block, graphite.

Specifically, the organic pigments include, for example, nitroso nitroso pigments such as Naphthol Green B, Naphthol Green Y; nitro pigments such as Naphthol S, Lithol Fast Yellow 2G, insoluble azo pigments such as Permanent Red 4R, Brilliant Fast Scarlet, Hanza Yellow, Benzidine Yellow; poorly-soluble azo pigments such as Lithol Red, Lake Red C, Lake Red D; soluble azo pigments such as Brilliant Caramine 6B, Permanent Red F5R, Pigment Scarlet 3B, Bordeaux 10B; phthalocyanine pipments such as Phthalocyanine Blue, Phthalocyanine Green, Sky Blue; basic dye pigments such as Rhodamine Lake, Malachite Green Lake, Methyl Violet Lake; acidic dye pigments such as Peacock Blue Lake, Eosin Lake, Quinoline Yellow Lake.

These pigments may be used alone or in combination of two or more of them.

Among these pigments, more preferred are inorganic pigments which are superior to organic pigments in the heat resistance, the light resistance and the like, for example, titanium white, blood red, black iron oxide, yellow iron oxide.

Next, processes for obtaining a mixed particle by uniformly mixing and dispersing an inorganic particle and a coloring particle may be carried out by any process such as a dry process and a wet process without any limitation. However, in order to mix and disperse each particle more uniformly, it is a more preferable aspect to mix and disperse them in the presence of an aqueous medium. In addition, a process for preparing an aqueous dispersion containing a mixed particle in which an inorganic particle and a coloring particle are dispersed uniformly is a more preferable aspect since it is easy to proceed to the subsequent step of forming a poly(organo)siloxane film. As a process of preparing this aqueous medium, any processes may be used without any problems, for example, a process in which an inorganic particle and a coloring particle are separately dispersed to prepare an aqueous dispersion, then, the two dispersions are mixed uniformly, and a process in which an inorganic particle and a coloring particle are simultaneously dispersed to prepare an aqueous dispersion.

A wet dispersing process does not require a special process, and may be performed by adopting a process generally used in the art. For example, a sand mill, a bead mill, an attritor, a colloid mill, a ball mill, an ultrasonic crusher, a homomixer, a dissolver, and a homogenizer may be used for dispersion.

The dispersion conditions vary depending upon a size, a hardness and an amount of the inorganic particle and coloring particle to be added, a kind and an amount of the aqueous medium to be added, a type of a dispersing machine, but the dispersion conditions, such as a dispersing time, a stirring machine and a rotation number may be appropriately selected depending upon the dispersion state of these particles. As the aqueous medium used in the wet dispersion, water and/or alcohols, ethers and ketones and the like which are miscible with water may be used. In addition, in order to improve the dispersibility further, a surfactant and a polymer auxiliary may be added without any limitation.

A mixing ratio of a coloring particle to an inorganic particle in the mixed particle is preferably 0.0001~25.0 parts by weight, more preferably 0.0001~10.0 parts by weight relative to 100 parts by weight of the inorganic particle.

In the next step, a poly(organo)siloxane film is formed on the surface of the mixed particle in which the inorganic particle and the coloring particle are mixed and dispersed uniformly. A process of forming a poly(organo)siloxane film may be perforated by either a wet process or a dry process without no limitation, but a wet process is a more preferred aspect because a uniform poly(organo)siloxane film can be formed.

At a point when the mixed particle is mixed and dispersed uniformly in the aqueous medium, to the aqueous dispersion containing the mixed particle, a silane compound represented by the general formula (I):

(I)

wherein Z is RO— or OCN—, X is halogen, Y is —OH, R is an organic group having a carbon number of 8 or less, and n, m and L are an integer of 0~ to 4, provided that n+m+L=4, and/or a low-condensate of the silane compound is added, then this is hydrolyzed or partially hydrolyzed in the system, which is condensed to form a poly(organo)siloxane film.

Alternatively, the silane compound represented by the general formula (I) and/or the low-condensate of the silane compound is hydrolyzed or partially hydrolyzed in the system, in the presence of at least one of an organosilane compound represented by the general formula (II):

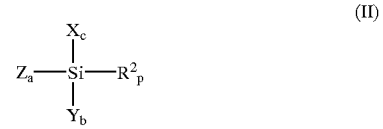

(II)

wherein Z is $R^1O$— or OCN—, X is halogen, Y is —OH, $R^1$ is an organic group having a carbon number of 8 or less, $R^2$ is an organic group, p is an integer of 1 to 3, and a, b and c are an integer of 0~ to 4, provided that a+b+c+p=4, a low-condensate of the organosilane compound and a metal compound, and co-condensed to form a poly(organo)siloxane.

Thereby, this system becomes in the state that the inorganic particle and the coloring particle are fine-dispersed uniformly without aggregating in an aqueous dispersion in which the condensed (organo)silane, that is, poly(organo)siloxane is dispersed.

A form of a compound to be added in the step of forming the above poly(organo)siloxane film is not particularly limited, but any forms may be used, for example, a monomer, a low-(co-)condensate (oligomer) in which a monomer is partially hydrolyzed and is low-(co-)condensed and a mixture thereof.

A process of adding to an aqueous dispersion is not particularly limited, but the compounds to be added may be added separately or after pre-mixed, and may be added in one portion or intermittently in a divided manner, but in order to improve uniformity of the addition, it is preferred that the compound to be added is diluted with an organic solvent miscible with an aqueous dispersion, which is added intermittently in a divided manner.

In addition, when a low-(co-)condensate is used to form a poly(organo)siloxane film, the shape is not particularly limited, but a linear shape is more preferable than a three-dimensional shape. Further, when a degree of polymerization is too large, the (co-)condensation reactivity with each of the surfaces of the inorganic particle and the coloring particle is inferior, and it is possible that the formation of a poly(organo)siloxane is deteriorated.

In addition, another process of forming a poly(organo)siloxane film may be performed without any limitation by using, for example, a process in which a solution containing a precursor of the above poly(organo)siloxane film is prepared in advance, and to the solution is added the resulting aqueous dispersion in which an inorganic particle and coloring particle aremixed and dispersed uniformly, then, a film is formed in the state where they are uniformly dispersed.

Z in the general formula (I) and the general formula (II) represents RO group, $R^1O$ group or OCN group which can generate a silanol group by hydrolysis, X represents halogen, and Y represents OH group. R and $R^1$ are an organic group having a carbon number of 8 or less and, more particularly, there can exemplified alkyl group or alkyl derivative such as methyl, ethyl, 2-chloroethyl, alkyl, aminoethyl, propyl, isopentyl, hexyl, 2-methoxyethyl, phenyl, m-nitrophenyl, 2,4-dichlorophenyl and the like. From a viewpoint of a rate of hydrolysis and discoloration due to remaining carbon in a poly(organo)siloxane film, methyl and ethyl are preferable. In addition, as a halogen, there are chlorine and bromine, and chlorine is preferable.

In addition, $R^2$ is not particularly limited as long as it is an organic group, but a shorter main chain of an organic group is preferable in that the structural strength of a poly(organo)siloxane film can be maintained.

As an example of a silane compound represented by the general formula (I), there are tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide (silicon oxide hydrate), tetraisocyanatosilane, ethoxysilane triisocyanate and the like. Among them, tetramethoxysilane and tetraethoxysilane are preferable.

In addition, it is more preferable to be a low-condensate of a silane compound represented by the general formula (I), more particularly, a low-condensate obtained by partially hydrolyzing and condensing tetramethoxysilane or tetraethoxysilane compound. These silane compounds can be used alone or in combination of two or more of them.

As an example of an organosilane compound represented by the general formula (II), there are methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltriethoxysilane, 3-aminopropyltriethoxysilane, methyltrichlorosilane, phenyltrichlorosilane, trimethylsilyl isocyanate, vinylsilyl triisocyanate, phenylsilyl triisocyanate and the like. Alternatively, low-condensates of these organosilane compounds may be used.

Among those organosilane compounds, vinyltrimethoxysilane, vinyltriethoxysilane, vinyltrichlorosilane, vinyl(β-methoxyethoxy)silane, γ-methacryloyloxypropyltrimethoxysilane, γ-glycidoxypropyltrimethoxysilane, γ-mercaptopropyltrimethoxysilane, γ-aminopropyltrimethoxysilane and the like are preferable, and γ-methacryloyloxypropyltrimethoxysilane is more preferable. These organosilane compounds may be used alone or in combination of two or more of them.

In addition, as a metal compound, there can be used, without any limitation, a metal compound which is hydrolyzed or partially hydrolyzed and condensed alone to form a skeleton of a poly(organo)siloxane film, a metal compound which makes a modificatory contribution to a skeleton in the presence of another compound forming a skeleton of a poly(organo)siloxane film. As an example of those metal compounds, there are metal halide, metal nitrate, metal sulfate, metal ammonium salt, organometal compound, alkoxy metal compound and derivatives of these metal compounds. The metal compounds may be used alone or in combination of two or more of them. As metal elements which constitute these compounds, there are respective elements of Periodic Table Group I–Group V. Among these metal compounds, metal compounds are preferable which comprise metal elements of Periodic Tables Group III~Group V which can be hydrolyzed and condensed alone to form a three dimensional skeleton are preferable. Metal compounds comprising Zr or Ti are more preferable. When a coloring filler of the present invention obtained by forming poly(organo)siloxane in the presence of a metal compound comprising these two kinds of metal elements is used as a filler for a dental composition, the radioapcity can be imparted to the composition. As a metal compound comprising Zr or Ti, there can be exemplified titanium tetrachloride, titanyl sulfate, methyltrichlorotitanium, dimethyldichlorotitanium, tetramethoxytitanium, tetraethoxytitanium, tetraisopropoxytitanium, tetraisobutoxytitanium, tetrakis(2-ethylhexyloxy)titanium, diethoxydibutoxytitanium, isopropoxytitanium trioctarate, diisopropoxytitanium diacrylate, tributoxytitanium stearate, zirconium tetrachloride, zirconium oxychloride, zirconium acetate, zirconium lactate, tetramethoxyzirconium, tetraethoxyzirconium, tetraisopropoxyzirconium, tetrabutoxyzirconium and the like. Alternatively, derivatives of the aforementioned metal compounds may be used. As a derivative of a metal compound, there can be exemplified a metal compound in which a part of a hydrolyzable group such as halogen, $NO_3$, $SO_4$ alkoxy group, acyloxy group and the like is substituted with a group which can form a chelating compound such as dicarboxylic acid group, oxycarboxylic acid group, β-diketone group, β-ketoester group, β-diester group, alkanolamine group and the like. Alternatively, a low-condensed metal compound (oligomer or polymer) obtained by partially hydrolyzing and low-condensing a metal compound may be used.

Hydrolysis or partial hydrolysis of a compound added to the aforementioned aqueous dispersion is performed under stirring at a relatively low speed. A stirring temperature is in a range of 10 C to 100 C, more preferably in a range of 25 C to 50 C and there is no limitation as long as it is a temperature below a boiling point of an aqueous medium. A stirring time is in a range of a few minutes to a few hours, more preferably in a range of 30 minutes to 24 hours, and can be adjusted by a kind and an amount of a compound to be added, a kind, an average particle size and a proportion occupied in its aqueous dispersion of an inorganic fine particle and the coloring particle, a kind and a proportion occupied in its aqueous dispersion of an aqueous medium and the like. Stirring does not need a special process but can be performed by adopting an equipment normally employed in the art. For example, stirring may be performed using a stirring machine which can stir a slurry such as a universal mixer, a planetary mixer and the like.

In addition, in order to control a rate of hydrolysis or partial hydrolysis and co-condensation, a sol-gel catalyst such as an acid, an alkali, an organometal compound, a metal alkoxide, a metal chelating compound and the like is preferably added. As an embodiment of a catalyst, there are an inorganic acid such as hydrochloric acid, acetic acid, nitric acid, formic acid, sulfuric acid, phosphoric acid and the like, an organic acid such as para-toluenesulfonic acid, benzoic acid, phthalic acid, maleic acid and the like, an alkali catalyst such as potassium hydroxide, sodium hydroxide, ammonia and the like. In addition, as an aqueous medium used in a step of forming a poly(organo)siloxane film, water and/or an organic solvent miscible with water can be used without any limitation. Particularly preferably, an aqueous solvent can be appropriately selected from alcohols, ketones and ethers. These solvents have the great effects that they not only improve compatibility of a variety of compounds used in a step of forming poly(organo)siloxane but also decrease the aggregability of particles in a heat-treating step and improve disintegrating property. As an embodiment of these solvents, there are alcohols such as ethyl alcohol, n-propyl alcohol, isopropyl alcohol, t-butyl alcohol, isobutyl alcohol and the like, ethers such as tetrahydrofuran, dioxane and the like. These solvents may be used alone or in combination of two or more of them. Preferably, ethyl alcohol, n-propyl alcohol and isopropylalcohol are suitably used.

An amount of a compound to be added for forming a poly(organo)siloxane film is not particularly limited, but can be appropriately selected depending upon a process of forming a poly(organo)siloxane film, a kind and an average particle size of an inorganic particle and a coloring particle in a mixed particle, and it is in a rage of 0.1~20.0 parts by weight in terms of $SiO_2$ amount relative to 100 parts by weight of the mixed particle, more preferably 0.1~5 parts by weight.

In addition, when a poly(organo)siloxane film is formed in the presence of a metal compound, the metal compound may be present in a range of 0.1~300 parts by weight, more preferably 0.1~100 parts by weight in terms of a metal oxide amount, relative to 100 parts by weight in terms of $SiO_2$ amount.

Next, a system in such the state is heat-treated and an aqueous medium is removed to solidify from an aqueous dispersion. Heat-treatment consists of two stages of aging and sintering, and the former is aimed at growing a poly(oragano)siloxane film and the latter is aimed at structural strengthening. The former needs to be performed by allowing to stand, so as not to impart distortion to the film structure and to remove an aqueous medium, and an equipment such as a box-type heat dryer and the like are preferable. An aging temperature is in a range of room temperature to 100 C, more preferably in a range of 40 C 80 C. When the temperature is below this range, removed of an aqueous medium is insufficient. When the temperature is above this range, rapid volatilization is caused, and there is a possibility that a defect is produced in a poly(organo)siloxane film, and peeling from the surface of a mixed particle is caused. Since an aging time depends upon the ability of a dryer, it is not limited as long as it is a time for sufficiently removing an aqueous medium. On the other hand, a sintering step consists of temperature rising and holding. In the former, it is better to gradually raise a temperature to a goal temperature for a longer period of time. Rapid temperature rising is not preferable because distortion is produced in a poly(organo)siloxane film. The latter is a sintering at a constant temperature and its time is 10 hours to 100 hours, more preferably 10 hours to 50 hours. A sintering temperature is in a range of 100~350 C, more preferably 100~200 C. This temperature must be appropriately selected to an extent that does not render a porous poly(organo)siloxane film non-porous. After an aqueous medium was removed by heat-treatment as described above, a shrank and solidified material was obtained. Although a solidified material is in the state of aggregation of a mixed particle, it is not a mere aggregate of mixed particles but a poly(organo)siloxane film formed by condensation intervenes, on an interface of an individual mixed particle. Therefore, when this solidified material is disintegrated to an extent of mixed particles before formation of a poly(organo)siloxane film, an individual mixed particle having the surface covered with poly(organo)siloxane, that is, a coloring filler of the present invention is obtained. As used herein, the term "disintegrated to an extent of an mixed particle before formation of a poly(organo)siloxane film" refers to disintegration to mixed particles. The different point from the original mixed particles is that an individual mixed particle is covered with poly(organo)siloxane. However, a secondary aggregate may be contained to a non-problematic extent. Disintegration can be easily performed by applying a shearing force or an impact force and, for example, disintegration can be performed using a Henschel mixer, a crossrotary mixer, a supermixer or the like.

The coloring filler of the present invention thus obtained has the surface covered with poly(organo)siloxane. An average particle size and particle size distribution of the coloring filler having the surface covered with poly(organo)siloxane, can be confirmed by a laser diffraction particle size measuring machine. As a result, it is recognized that the coloring filler of the present invention is powdered in the uniform dispersion state because it has the same average particle size and monodisperse particle size distribution as those in the state where mixed particles are dispersed uniformly. On the other hand, an average particle size of a mixed particle which is not covered with poly(organo)siloxane is shifted to a larger side and polydisperse particle size distribution is shown due to the presence of an aggregate. Alternatively, these dispersion states can be confirmed by observation with an electron microscope. In addition, a specific surface area of the coloring filler of the present invention can be measured by BET method and it is recognized that a specific surface area thereof is increased due to formation of a poly(organo)siloxane film. In addition, although a large number of OH groups are present on the film surface, the fluidity and the dispersibility of a filler are better. This is considered to be resulted from the fact that contact between particles is point contact due to the irregular parts of the film surface. The thickness of a poly(organo)siloxane film is influenced by an amount of an (organo)siloxane compound to be added and is 500 $\mu$m or less, more preferably 100 $\mu$m or less. In addition, when this coloring filler is used in a dental composition, a resin component is penetrated into the irregular parts of the surface of a poly(organo)siloxane film and it is recognized that the mechanical properties are improved by the fitting effect.

In addition, in order to pack this coloring filler at a large amount, it is effective to further treat a poly(organo)siloxane film with an organosilane compound represented by the general formula (II):

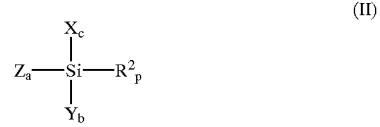

(II)

wherein Z is $R^1O-$ or $OCN-$, X is halogen, Y is $-OH$, $R^1$ is an organic group having a carbon number of 8 or less, $R^2$ is an organic group, p is an integer of 1 to 3, and a, b and c are all an integer of 0~ to 3, provided that a+b+c+p=4. As a result, packing at a large amount becomes possible and various properties necessary as a dental composition can be satisfied.

Among the aforementioned organosilane compounds, a silane coupling agent which is known in the dental field is effective and examples thereof are vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltriethoxysilane and the like. γ-methacryloyloxypropyltrimethoxysilane is more preferable. These organosilane compounds can be used alone or in combination of two or more of them.

The affinity with a resin component is enhanced by these organosilane compounds because the surface of an organosilane compound is effectively and uniformly treated by a reaction with a large number of OH groups present on a poly(organo)siloxane film.

Another aspect of the present invention is a dental composition containing the coloring filler of the present invention. Specifically, it is a dental composition containing (a)

the coloring filler of the present invention, (b) a polymerizable monomer, and (c) a polymerization initiator. Further, it is a dental composition containing (a) the coloring filler of the present invention, (b) a polymerizable monomer, (c) a polymerization initiator and (d) a filler.

The coloring filler of the present invention, due to the presence of a poly(organo)siloxane film on the surface thereof, can be dispersed uniformly in the state of non-aggregate in a resin matrix of a polymerizable monomer and the like, which are a constituent in the dental composition, and can endow the dental composition with clear and elegant color. Further, the high affinity with a resin matrix stabilizes the characteristics of a paste thereof and, furthermore, it allows the cured composition to exhibit the excellent properties.

A polymerizable monomer which can be used in a dental composition together with a coloring filler of the present invention, can be used by selecting from the known monofunctional and multifunctional polymerizable monomers which are generally used as a dental composition.

Representative examples which are generally used suitably are polymerizable monomers having an acryloyl group and/or a methacryloyl group. In the present invention, (meth)acrylate or (meth)acryloyl represented inclusively both acryloyl group-containing polymerizable monomers and methacryloyl group-containing polymerizable monomers.

Embodiments thereof are as follows:

As polymerizable monomers having no acidic group, monofunctional monomer: (meth)acrylic acid esters such as methyl(meth)acrylate, ethyl (meth)acrylate, butyl(meth)acrylate, hexyl(meth)acrylate, tetrahydrofurfuryl(meth)acrylate, 2-hydroxyethyl(meth)acrylate, grycidyl(meth)acrylate, lauryl(meth)acrylate, cyclohexyl(meth)acrylate, allyl(meth)acrylate, 2-ethoxyethyl(meth)acrylate, methoxy polyethylene glycol(meth)acrylate, glycerol(meth)acrylate, isobonyl(meth)acrylate and the like, silane compounds such as γ-(meth)acryloyloxypropyltrimethoxysilane, γ-(meth)acryloyloxypropyltriethoxysilane and the like, nitrogen-containing compounds such as 2-(N,N-dimethylamino)ethyl (meth)acrylate, N-methylol(meth)acrylamide, diacetone (meth)acrylamide and the like, Aromatic Bifunctional Monomer:

2,2-bis(4-(meth)acryloyloxyphenyl)propane,
2,2-bis(4-(3-(meth)acryloyloxy-2-hydroxypropoxy) phenyl)propane,
2,2-bis(4-(meth)acryloyloxyethoxyphenyl)propane,
2,2-bis(4-(meth)acryloyloxydiethoxyphenyl)propane,
2,2-bis(4-(meth)acryloyloxytetraethoxyphenyl)propane,
2,2-bis(4-(meth)acryloyloxypentathoxyphenyl)propane,
2,2-bis(4-(meth)acryloyloxydipropoxyphenyl)propane,
2,2-bis(4-(meth)acryloyloxyethoxyphenyl)-2-(4-(meth) acryloyloxydiethoxyphenyl)propane,
2-(4-(meth)acryloyloxydiethoxyphenyl)-2-(4-(meth) acryloyloxytriethoxyphenyl)propane,
2-(4-(meth)acryloyloxydipropoxyphenyl)-2-(4-(meth) acryloyloxytriethoxyphenyl)propane,
2,2-bis(4-(meth)acryloyloxypropoxyphenyl)propane,
2,2-bis(4-(meth)acryloyloxyisopropoxyphenyl)propane and the like, Aliphatic Bifunctional Monomer:

2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol(meth)acrylate, 1,6-hexanediol (meth)acrylate, glycerin di(meth)acrylate and the like, Trifunctional Monomer:

trimethylolpropane tri(meth)acrylate, treimethylolethane tri(meth)acrylate, trimethylolmethane tri(meth) acrylate, pentaerythritol tri(meth)acrylate and the like, Tetrafunctional Monomer:

pentaerythritol tetra(meth)acrylate, ditrimethylolporpane tetra(meth)acrylate and the like.

In addition, embodiments of an urethane system polymerizable monomer are di(meth)acrylates having a bifunctional or trifunctional or more-functional urethane linkage which are derived from an adduct of a polymerizable monomer having a hydroxy group such as 2-hydroxyethyl(meth) acrylate, 2-hydroxypropyl(meth)acrylate and 3-chloro-2-hydroxypropyl(meth)acrylate and a diisocyanate compound such as methylcyclohexane diisocyanate, methylene bis(4-cyclohexyl isocyanate), isophorone diisocyanate, diisocyanate methylbenzene and, 4,4-diphenylmethane diisocyanate.

In addition to the aforementioned (meth)acrylate system polymerizable monomers, other polymerizable monomers, for example, a monomer, an oligomer or a polymer having at least one polymerizable group in the molecule may be used depending upon the purpose of a dental composition without any limitation. In addition, there is no problem that the polymerizable monomers have a substituent such as an acidic group, a fluoro group and the like.

In the present invention, a polymerizable monomer includes not only a single component but also a mixture of a plurality of polymerizable monomers.

In addition, when a polymerizable monomer has the extremely high viscosity at room temperature or when a polymerizable monomer is a solid at room temperature, it is preferably used as a mixture of polymeuizable monomers by combining with a polymerizable monomer having the low viscosity. This combination may comprise not only two kinds but also three kinds or more.

In addition, since a polymer comprising only monofunctional polymerizable monomers has no cross-linking structure, it generally has a tendency to be inferior in the mechanical strength of a polymer.

For that reason, when a polymerizable monomer is used, it is preferable that it is used with a polyfunctional polymerizable monomer. The most preferable combination of polymerizable monomers is a manner of combining an aromatic compound of a bifunctional polymerizable monomer as a main component with an aliphatic compound of a bifunctional polymerizable monomer.

More particularly, there is a combination of 2,2-bis(4-(3-methacryloyloxy-2-hydroxypropoxy)phenyl)propane (Bis-GMA) and triethylene glycol dimethacrylate (TEGDMA).

When a teeth substance and a nonprecious metal adhering property is imparted to a dental composition containing coloring fillers of the present invention, it is effective to use a polymerizable monomer containing an acid group such as a phosphoric acid group, a carboxylic acid group, a sulfonic acid group or the like in the molecule as a part or the whole of a polymerizable monomer.

In addition, in order to enhance a precious metal adhering property, it is also effective to the present invention to use those polymerizable monomers containing a sulfur atom in the molecule. Embodiments of these polymerizable monomers having the adhering ability are as follows:

Carboxylic acid group-containing polymerizable monomer:
(meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 2-(meth)acryroyloxybenzoic acid, β-(meth)acryroyloxyethyl hydrogen succinate, β-(meth)acryroyloxyethyl hydrogen maleate, 11-(meth)acryloyloxy-1,1-undecanedicarboxylic acid, p-vinylbenzoic acid and the like, Phosphate Group-containing Monomer:
2-(meth)acryloyloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl)hydrogen phosphate, 2-(meth)acryloyloxyphenyl hydrogen phosphate and the like, Sulfonic Group-containing Monomer:
2-(meth)acrylamide-2-methylpropanesulfonic acid,
4-(meth)acryloyloxybenzenesulfonic acid,
3-(meth)acryloyloxypropanesulfonic acid and the like, Sulfur Atom-containing Monomer:
(meth)acrylate having a triazinethiol group, (meth)acrylate having a mercapto group, (meth)acrylate having a polysulfide group, (meth)acrylate having a thiophosphate group, (meth)acrylate having a disulfide group, (meth)acrylate having a mercaptodithiazole group, (meth)acrylate having a thiouracil group, (meth)acrylate having a thiirane group and the like.

These polymerizable monomers are used alone or as a mixture of two or more without any problem.

A polymerization initiator which can be used with coloring fillers of the present invention in a dental composition is not particularly limited and the known radical generator can be used without any limitation.

Polymerization initiators are generally classified into initiators which initiate polymerization by mixing prior to use (chemical polymerization initiator), initiators which initiate polymerization by heating or warming (thermal polymerization initiator), and initiators which initiate polymerization by light irradiation (photoinitiators).

As a chemical polymerizable initiator, there are polymerizable initiator systems of a redox type comprising an organic peroxide/an amine compound or an organic peroxide/an amine compound/a sulfinic acid salt, or an organic peroxide/an amine compound/a borate compound, and organometal type initiator system which initiates polymerization by a reaction with oxygen or water. Further, sulfinic acid salts and borate compounds can also initiate polymerization by a reaction with a polymerizable monomer having an acidic group.

Embodiments of the aforementioned organic peroxide are benzoylperoxide, parachlorobenzoylperoxide, 2,4-dichlorobenzoyl peroxide, 2,5-dihydroperoxy-2,5-dimethylhexane, methyl ethyl ketone peroxide, tertiary-butyl peroxide benzoate and the like.

As the aforementioned amine compound, a secondary or tertiary amine in which an amine group is bound to an aryl group is preferable and embodiments. thereof are p-N,N-dimethyltoluidine, N,N-dimethylaniline, N-β-hydroxyethylamine, N,N-di(β-hydroxyethyl)aniline, p-N,N-di(β-hydroxyethyl)toluidine, N-methylaniline, p-N-methyltoluidine and the like.

Embodiments of the aforementioned sulfinic acid salt are sodium benzenesulfinate, lithium benzenesulfinate, sodiump-toluenesulfinate and the like.

As the aforementioned borate compound, there are trialkylphenylboron, and sodium salt, lithium salt, potassium salt, magnesium salt, tetrabutyl ammonium salt, tetramethyl ammonium salt of trialkyl (p-fluorophenyl)boron (wherein alkyl group is n-butyl group, n-octyl group, n-dodecyl group or the like). In addition, as the aforementioned organornetal type polymerizable initiator, there are organic boron compounds such as triphenylborane, tributylborane, partial oxide of tributylborane and the like. In addition, as a thermal polymerization initiator by heating or warming, azo compounds such as azobisisobutyronitrile, methyl azobisisobutyrate, azobiscyano valeric acid and the like are suitably used.

On the other hand, as a photoinitiator, there are a photoinitiator comprising a photosensitizer, a photosensitizer/a photopolymerization promotor and like.

Embodiments of the aforementioned photosensitizer are α-diketones such as benzil, camphorquinone, α-naphtil, acetonaphtone, p,p'-dimethoxybenzil, pentandione, 1,2-phenanthrenquinone, 1,4-phenanthrenquinone, 3,4-phenanthrenquinone, 9,10-phenanthrenquinone, naphthoquinone and the like benzoin alkyl ethers such as benzoin, benzoin methyl ether, benzoin ethyl ether and the like, thioxanthones such as thioxanthone. 2-chlorothioxanthone, 2-methylthioxanthone, 2-hydroxythioxanthone, 2,4-diethylthioxanthone, 2,4-diisopropylthioxanthone and the like, benzophenones such as benzophenone, p-chlorobenzophenone, p-methoxybenzophenone and the like, acylphosphineoxides such as 2,4,6-trimethylbenzoyl diphenylphosphineoxide, bis(2,6-dimethoxybenzoyl)-2,4,4-trimethylpentylphosphineoxide and the like, α-aminoacetophenones such as 2-benzyldimethylamino-1-(4-morpholinophenyl)butanone-1,2-benzyl-diethylamino-1-(4-morpholinophenyl)propanone-1 and the like, ketals such as benzyldimethylketal, benzyldiethylketal, benzyl(2-methoxyethylketal) and the like, titanocenes such as bis (cyclopentadienyl)-bis[2,6-difluoro-3-(1-pyrolyl)phenyl] titanium, bis(cyclopentadienyl)-bis(pentanefluorophenyl) titanium, bis(cyclopentadienyl)-bis(2,3,5,6-tetrafluoro-4-disiloxyphenyl)-titanium and the like.

Embodiments of the aforementioned photopolymerization promoters are tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 2-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, 2,2'-(n-butylimino)diethanol and the like, secondary amines such as N-phenylglycine and the like, barbituric acid such as 5-butylbarbituric acid, 1-benzyl-5-phenylbarbituric acid and the like, tin compounds such as dibutyltin diacetate, dibutyltin dilaurate, dioctyltin dilaurate, dioctyltin diperacetate, dioctyltin bis(mercaptoacetic acid isooctyl ester) salt, tetramethyl-1,3-diacetoxydistannoxane and the like, aldehyde compounds such as lauryladehyde, terephthalaldehyde and the like, sulfur-containing compounds such as dodecylmercaptan, 2-mercaptobenzoxazole, 1-decanethiol, thiosalicylic acid and the like.

In addition, for improving the photopolymerization promoting ability, the additions of oxycarboxylic acids such as citric acid, maleic acid, tartaric acid, glycolic acid, gluconic acid, α-oxyisobutyric acid, 2-hydroxypropioic acid, 3-hydroxybutanoic acid 4-hydroxybutanoic acid, dimethylolpropioic acid and the like is effective besides the additions of the aforementioned photopolymerization promoters.

Those polymerization initiators may be used alone or as a mixture of two or more of them. In addition, they can be used in a combination irrespective of a polymerization form and a kind of a polymerization initiator.

An amount of a polymerization initiator to be added may be appropriately selected depending upon the use. In general, the amount may be selected from a range of 0.1~10 parts by weight relative to a polymerizable monomer.

Among the aforementioned polymerization initiators, it is preferable to use a photopolymerization initiator which generates a radical by light irradiation and such the initiator is most suitably used in that a dental composition can be polymerized in the state where an air is mixed therein at a small amount. In addition, among photopolymerization initiators, a combination of α-diketone and tertiary amine is preferable and a combination of carnphorquinone with an aromatic amine having an amino group directly bound to a benzene ring such as ethyl p-N,N-dimethylaminobenzoate and the like or an aliphatic amine having a double bond in the molecule such as N,N-dimethylaminoethyl methacrylate is most preferable.

In addition, sensitizing pigments such as coumarin, cyanine, thiazine and the like, a light acid generator which produces Bronsted acid or Lewis acid by light irradiator such as a s-triazine derivative substituted which a halomethyl group, diphenyl iodonium salt compound and the like, quaternary ammonium halides, transition metal compound are also suitably used depending upon the use.

Another filler which can be used in a dental composition in combination with coloring fillers of the present invention is not particularly limited, but the known filler, for example, an inorganic filler and/or an organic filler and/or an organic-inorganic compound filler, can be used without any limitation. A shape of such a filler is not particularly limited, but particle shapes such as of sphere, needle, plate, crushed and flake may be taken. Also, a kind of the filler is not particularly limited.

Examples of an inorganic filler include quartz, amorphous silica, aluminium silicate, aluminium oxide, titanium oxide, zirconium oxide, various glasses (including a glass prepared by a melting process, a synthetic glass prepared by a sol-gel process, a glass produced by a vapor phase process), calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide, zeolite and the like. Among them, preferred are an aluminosilicate glass, a borosilicate glass, an aluminoborate glass, a boroaluminosilicate glass and the like, which contain heavy metals such as sodium, strontium, barium and lanthanum and/or fluoride. An average particle size of the inorganic filler is not particularly limited, but it is preferably in a range of 0~10 $\mu$m, and more preferably in a range of 0~5 $\mu$m.

In addition, ultrafine particle inorganic fillers such as Aerosil produced by a vapor phase process or a particle of silica-zirconia oxide produced from a solution by a sol-gel process can be used. In addition, an aggregated inorganic filler in which such the ultrafine particle is aggregated may be used without any problem.

In addition, an organic filler can be prepared by polymerizing a monomer having a polymerizable group, and a kind thereof is not particularly limited. Examples of an organic filler include fillers prepared by (co)polymerizing a polymerizable monomer, alone or in combination, such as unsaturated aromatic compounds such as styrene, α-methylstyrene, halogenated styrene and divinylbenzene; unsaturated esters such as vinyl acetate and vinyl propionate; unsaturated nitrites such as acrylonitrile; and butadiene and isoprene. Particularly preferred is a filler prepared by polymerizing the above polymerizable monomer which is known in the dental field. A process for producing an organic filler is also not particularly limited, but processes such as emulsion polymerization, suspension polymerization and dispersion polymerization, or a process of grinding a preformed polymer bulk can be employed.

Alternatively, an organic-inorganic compound filler containing an inorganic particle in an organic polymer can be used. An inorganic particle to be contained in an organic polymer is not particularly limited, but the known inorganic particle, for example, the aforementioned inorganic filler can be contained. A process for producing an organic-inorganic compound filler is also not particularly limited, but any process can be adopted. Examples of such the process include a process for micro-encapsulating an inorganic particle with an organic material or grafting the surface of an inorganic particle with an organic material, a process for radical-polymenzing a polymerizable fuinctional group or a polymerizable initiation group on the surface of an inorganic particle after introducing it to the surface, a process for grinding a polymer bulk containing inorganic particles which have been produced in advance, and the like.

An average particle size of an organic or organic-inorganic composite compound filler is preferably in a range of 1~100 $\mu$m, more preferably in a range of 3~50 $\mu$m, and most preferably within a range of 5~30 $\mu$m. These inorganic, organic and organic-inorganic compound fillers can be used alone or in combination thereof.

Fillers such as inorganic, organic and organic-inorganic compound fillers can be used for a dental composition, after the surface of a particle thereof is treated with, for example, surfactants, fatty acids, organic acids, inorganic acids, silane coupling agents, titanate coupling agents, polysiloxane or the like. These surface treating processes are preferable in that these can enhance the wettability between a resin component and the filler surface and can impart various excellent properties to a dental composition, and these can be arbitrarily selected depending upon the required properties. Moreover, in order to multi-functionalize these fillers, surface treatment with special surface treating agents and/or by a special process of surface treatment can be conducted without any limitation.

A proportion of such the filler in a dental composition may be optionally selected depending upon material property required for a dental composition.

An filling amount of low-viscous materials such as sealants, bonding materials, primers, tooth surface treating agents, opacifying agents and cements generally used in the dental field should be set at a relatively small level since higher fluidity required as material property is required for these materials. Therefore, the amount is preferably in a range of 5.0~80.0 parts by weight, more preferably in a range of 30.0~70.0 parts by weight relative to the whole component of a dental composition.

In addition, an filling amount of high-viscous materials such as a composite resin and a beneer crown resin should be set at a relatively high level since, as the required material property, such the shapability is required that does not cause deformation after shape adjustment. Accordingly, the amountis preferably in a range of 50.0~98.0 parts by weight, more preferably in a range of 75.0~98.0 parts by weight relative to the whole component of a dental composition.

In addition, if needed, components such as ultraviolet absorbing agents such as 2-hydroxy-4-methylbenzophenone, polymerization inhibitors such as hydroquinone, hydroquinone monomethyl ether and 2,5-di (tertiary-butyl)-4-methylphenol, anti-discoloring agents, antimicrobial agents, and other conventional known additives may be optionally added to a dental composition.

A packing type of the dental composition of the present invention is not particularly limited, but it may be any one of one-package type, two-package type and the like depending upon a kind of a polymerization initiator or a purpose of use, and it may be appropriately selected depending upon the application.

EXAMPLES

The following Examples further illustrate the present invention in more detail and specifically, but the present invention is not limited thereto.

The methods for evaluating the performance of a dental composition which were adopted in the following Examples are as follows.

(1) A Toothbrush Abrasion Wear Test

An Object of Evaluation

To evaluate abrasive wear resistance of a dental composition test sample.

A Method of Evaluation

A dental composition prepared was filled in four stainless molds (rectangular molds of 15×15×2.6 mm and 25×15×2.6 mm) separately for a toothbrush wear test). Glass covers were placed on the both sides and it was pressed by with a glass plate, then a dental composition was cured by irradiating with the light at six positions per sample for 30 seconds using a photopolymerization irradiating machine (Griplight II: manufactured by Shofu Inc.). After curing, a cured product was removed from the mold, and polished successively with sandpaper of #600 and #1200 to adjust the thickness thereof to 2.5 mm, which was used as a test sample (rectangular samples of 15×15×2.5 mm and 25×15×2.5 mm). Then, the surface of the test sample was planished by buffing, and followed by measuring the weight thereof. After that, the test sample was mounted on a toothbrush abrasion wear test machine to perform a toothbrush abrasion wear test of 30,000 cycles (about 3 hours) using a toothbrush (Perio H: manufactured by Sunstar Inc.) and a toothpaste (White: manufactured by Sunstar Inc.).

(2) A Polishability Test

An Object of Evaluation

To evaluate the smoothness and glossiness of a dental composition test sample.

A Method of Evaluation

A dental composition prepared was filled in a stainless mold (4φ×6 mm: cylindrical shape). Glass covers were placed on both sides of the mold and pressed with a glass plate, then the dental composition was cured by irradiating with the light from the both sides mold using a photopolymerization irradiating machine (Griplight II: manufactured by Shofu Inc.). After curing, the cured product was removed from the mold, and the state of the polished surface Dias v isually observed using ten samples, which was used as a test sample. Then, the test sample was polished using successively Silicon Point (manufactured by Shofu Inc.) and One Gloss Super Buff (manufacture by Shofu Inc.), and the situation of the polished surface was evaluated with naked eyes. The test was performed by using ten samples and evaluated comprehensively.

(3) A coloring Resistance Test

An Object of Evaluation

To evaluate the coloring resistance of a dental composition test sample and surface treated fillers prepared in Examples A-4~A-6 and Comparative Examples A-4~A-6.

A Method of the Evaluation

1) A dental composition prepared was filled in a stainless mold (15φ×1 mm: disc shape). Glass covers were placed on both sides and pressed with a glass plate, then the dental composition was cured by irradiating with the light at six positions per sample for 30 seconds using a photopolymerization irradiating machine (Griplight II: manufactured by Shofu Inc.). After curing, the cured product was removed from the mold and both sides thereof were slightly polished with sandpaper of #1200 to remove a resin layer, which was used as a test sample. Thereafter, the color of the test sample was measured using a spectrocoloiimeter (CM-2000, manufactured by Minolta), and immersed into a 5.0% aqueous solution of instant coffee (Nescafe) at 37 C for 24 hours. After immersed for 24 hours, the test sample was removed, washed with water, and the color was measured again. Color difference (E*ab) was calculated by measured color values before and after immersion. The test was carried out on five samples and evaluated using an average of five measurements.

2) Each 5 g of the surface treated fillers prepared in Examples A-4~A-6 and Comparative Examples A-4~A-6 was immersed in a 5.0% aqueous solution of instant coffee (Nescafe) at 37 C for 24 hours. After inunersion for 24 hours, the filler the surface-treated inorganic filler was filtrated, and a degree of coloration was evaluated based on the following criteria.

O: Slightly colored

Δ: Heavily colored

X: Remarkably colored (4) A bending Test

An Object of Evaluation

To evaluate the bending strength of a dental composition test sample.

A Method of Evaluation

A dental composition prepared was filled in a stainless mold (25×2×2 mm: rectangular parallelepiped-shape). Then, glass covers were placed on both sides of the mold and was pressed with a glass plate, then the dental composition was cured by irradiating with the light at five positions per sample for 30 seconds using a photopolymerization irradiating machine (Griplight II: manufactured by Shofu Inc.). After curing, the cured product was removed from the mold and the other side was irradiated with the light similarly which was used as a test sample. After the test sample was immersed in water at 37 C for 24 hours, a bending test was carried out at a distance between supports of 20 mm and a crosshead speed of 1 mm/minute using an Instron type universal tester (Instron 5567, manufactured by Instron Inc.). Additionally the test was performed by using ten samples and evaluated with an average value of the ten samples.

Example A of an Inorganic Filler of the Present Invention (Production of a Raw Material Inorganic Particle)

Respective raw materials were sufficiently mixed at a proportion of 43 parts by weight of silica, 20 parts by weight of aluminium oxide, 5 parts by weight of sodium fluoride, 10 parts by weight of calcium fluoride, 5 parts by weight of calcium phosphate and 17 parts by weight of strontium carbonate, and the mixture was placed in a high-temperature electronic furnace at 1400 C and the temperature was held for 5 hours to melt the raw materials. After melting, cooling afforded a glass as a raw material for a filler. The produced glass was ground by a ball mill for 12 hours and passed through a #200 mesh sieve to obtain a raw material inorganic particle for wet-grinding. An average particle size of the raw material inorganic particle was approximately 10 $\mu$m.

Example A-1

Preparation of a Polysiloxane-covered Inorganic Filler "Inorganic Filler 1"

(Wet-grinding)

After 4 kg of alumina boulder having a diameter of 6 $\mu$m $\phi$ was placed in an alumina pot of a tetraplex oscillating mill (internal volume 3.6 L), 540 parts by weight of a raw material inorganic particle obtained above and 1,000 parts by weight of ion exchanged water were added therein, respectively, and the mixture was wet-ground for 40 hours. After grinding, an average particle size and a particle size distribution of the ground slurry were measured by a laser diffraction particle size measuring machine ("Microtrack SPA" manufactured by Nikkiso Inc.). The results of the measuremhent showed an average particle size of 1.2 $\mu$m and monodisperse particle size distribution. Furthennore, after grinding, the alumina boulder and the ground slurry in the alumina pot were separated to obtain "ground slurry 1".

(Polysiloxane Treatment)

1,500 parts by weight of "ground slurry 1" and 54.1 parts by weight of a low-condensed product of a silane compound "MS51SG1" (SiO$_2$ content 16%, degree of polymerization 2~6; manufactured by.Mitsubishi Chemical Inc.) were added to a universal mixer and mixed for approximately 90 minutes. After mixed for the predetermined period of time, the treated slurry obtained was aged in a heat dryer at 50 C for 40 hours and, thereafter, a temperature was raised to 150 C and held for 6 hours, followed by cooling to obtain the heat-treated solidified material. The heat-treated solidified material obtained was placed in a Henschel mixer and disintegrated at 1800 rpm for 5 minutes. After disintegration, "inorganic filler 1" having the better fluidity and having the surface covered with pglysiloxane (SiO$_2$ 1.65%) was obtained. A particle size and a particle size distribution of the filler were measured by a laser diffraction particle size measuring machine "Microtrack SPA" and the results showed an average particle size of 1.2 $\mu$m and monodisperse particle size distribution.

Example A-2

Preparation of a Polysiloxane-covered Inorganic Filler "Inorganic Filler 2"

After 4 kg of alumina boulder having a diameter of 6 mm 0 was placed in an alumina pot of a tetraplex oscillating mill (internal volume 3.6 L), 540 parts by weight of a raw material inorganic particle obtained above and 1,000 parts by weight of ion exchanged water were added therein, respectively, to wet-grind for 15 hours. After grinding, an average particle size and a particle size distribution of the ground slurry were measured by a laser diffraction particle size measuring machine ("Microtrack SPA" manufactured by Nikkiso Inc.). The results showed an average particle size of 3.2 $\mu$m and monodisperse particle size distribution. Furthermore, after grinding, the alumina bolder and the ground slurry in the alumina pot were separated to obtain "ground slurry 2".

(Polysiloxane Treatment)

1,500 parts by weight of "ground slurry 2" and 21.7 parts by weight of a low-condensed product of a silane compound "MS51SG1" (SiO$_2$ content 16%, degree of polymerization 2~6; manufactured by Mitsubishi Chemical Inc.) were added to a universal mixer to mix for approximately 90 minutes. After mixed for the predetermined period of time, the treated slurry obtained was aged in a heat dryer at 50 C for 40 hours and, thereafter, a temperature was raised to 150 C and held for 6 hours, followed by cooling to obtain the heat-treated solidified material. The heat-treated solidified material obtained was placed in a Henschel mixer and disintegrated at 1800 rpm for 5 minutes. After disintegration, "inorganic filler 2" having the better fluidity and having the surface covered with polysiloxane (SiO$_2$ 0.66%) was obtained. A particle size and a particle size distribution of this filler were measured by a laser diffraction particle size measuring machine "Microtrack SPA" and the results showed an average particle size of 3.2 $\mu$m and monodisperse particle distribution.

Example A-3

Preparation of a Polysiloxane-covered Inorganic Filler "Inorganic Filler 3"

After 4 kg of alumina boulder having a diameter of 6 mm $\phi$ was placed in an alumina pot of a tefraplex oscillating mill (internal volume 3.6 L), 540 parts by weight of a raw material inorganic particle obtained above and 1,000 parts by weight of ion exchanged water were added therein, respectively, to wet-grind for 8 hours. After grinding, an average particle size and a particle size distribution of the ground slurry were measured by a laser diffraction particle size measuring machine ("Microtrack SPA" manufactured by Nikkiso Inc.). The results showed an average particle size of 7.5 $\mu$m and monodisperse particle size distribution. Furthermore, after grinding, the alumina bounder and the ground slurry in the alumina pot were separated to obtain "ground slurry 3".

(Polysiloxane Treatment)

1,500 parts by weight of "ground slurry 3" and 10.8 parts by weight of a low-condensed product of a silane compound "MS51SG1" (SiO$_2$ content 16%, degrees of polymerization 2~6; manufactured by Mitsubishi Chemical Inc.) were added to a universal mixer to mix for approximately 90 minutes. After mixed for the predetermined period of time, the treated slurry obtained was aged in a heat dryer at 50 C for 40 hours and, thereafter, a temperature was raised to 150 C and held for 6 hours, followed by cooling to obtain the heat-treated solidified material. The heat-treated solidified material obtained was placed in a Henschel mixer and disintegrated at 1800 rpm for 5 minutes. After disintegration, "inorganic filler 3" having the better fluidity and having the surface covered with polysiloxane (SiO$_2$ 0.33%) was obtained. A particle size and a particle size distribution of this filler were measured by a laser diffraction particle size measuring machine "Microtrack SPA" and the results showed an average particle size of 7.5 µm and monodisperse particle distribution.

Comparative Examples A-1~A-3

Each ground slurry obtained by wet-grinding in Examples A-1~A-3 was aged in a heat dryer at 50 C for 40 hours without conducting the polysiloxane treatment, then a temperature was raised to 150 C and held for 6 hours, followed by cooling to obtain the heat-treated solidified material. The heat-treated solidified material obtained was placed in a Henschel mixer and disintegrated at 1800 rpm for 5 minutes to obtain inorganic particles 1~3 without polysiloxane treatment. The results of the fluidity and particle size measurement of each particle after disintegration are shown in Table A-1.

TABLE A-1

| Comparative Example No. | Average particle size (µm) | Fluidity | Particle size distribution |
|---|---|---|---|
| A-1 | 4.0 | Worse | Broad- and poly-dispersion |
| A-2 | 5.6 | Worse | Broad- and poly-dispersion |
| A-3 | 7.5 | Better | Broad- and mono-dispersion |

Example A-4

Preparation of a Silane-treated Inoraranic Filler With Polysiloxane Treatment "Silane-treated Inorganic Filler 1"

500 parts by weight of the above "inorganic filler 1" was placed in a Henschel mixer to stir, and a solution prepared by dissolving 60 parts by weight of a silane coupling agent, γ-methacryloyloxypropyltrimethoxysilane in 60 parts by weight of ethanol was sprayed thereto under stirring. After spraying, the filler was removed firom a Henschel mixer and heat-treated in a heat dryer at 100 C for 3 hours to obtain s a silane-treated inorganic filler 1.

Example A-5

Preparation of a Silane Treated Silane-treated Inorganic Filler With Polysiloxane Treatment "Silane-treated Inorganic Filler 2"

500 parts by weight of the above "inorganic filler 2" was placed in a Henschel mixer to stir, and a solution prepared by dissolving 45 parts by weight of γ-methacryloyloxypropyltrimethoxysilane in 60 parts by weight of ethanol was sprayed thereto under stirring. After spraying, the filler was removed from a Henschel mixer and heat-treated in a heat dryer at 100 C for 3 hours to obtain Silane treated a silane-treated inorganic filler 2.

Example A-6

Preparation of a Silane-treated Inorganic Filler With Polysiloxane Treatment "Silane-treated Inorganic Filler 3"

500 parts by weight of the above "inorganic filler 3" was placed in a Henschel mixer to stir, and a solution prepared by dissolving 30 parts by weight of γ-methacryloyloxy- propyltrimethoxysilane in 60 parts by weight of ethanol was sprayed thereto under stirring. After spraying, the filler was removed from a Henschel mixer and heat-treated in a heat dryer at 100 C for 3 hours to obtain a silane-treated inorganic filler 3.

Comparative Example A-4

Preparation of a Silane-treated Inorganic Particle 1 Without Polysiloxane Treatment The inorganic particle 1 without polysiloxane treatment obtained in Comparative Example A-1 was treated with a silane coupling agent according to the same manner as that of Example A-4 to obtain a silane-treated inorganic particle 1 without polysiloxane treatment.

Comparative Example A-5

Preparation of a Silane-treated Inorganic Particle 2 Without Polysiloxane Treatment The inorganic particle 2 without polysiloxane treatment obtained in Comparative Example A-2 was treated with a silane coupling agent according to the same manner as that of Example A-5 to obtain a silane-treated inorganic particle 2 without polysiloxane treatment.

Comparative Example A-6

Preparation of a Silane-treated Inorganic Particle 3 Without Polysiloxane Treatment The inorganic particle 3 without polysiloxane treatment obtained in Comparative Example A-3 was treated with a silane coupling agent according to the same manner as that of Example A-6 to obtain a silane-treated inorganic particle 3 without polysiloxane treatment.

Examples A-7~A-9 and Comparative Examples A-7~A-9

Composition A was prepared according to the following formulation.
[Composition A]

| | |
|---|---|
| 2,2-bis(4-(3-methacryloyloxy-2-hydroxypropoxy) phenyl)propane (Bis-GMA) | 60 parts by weight |
| Triethyleneglycol dimethacrylate (TEGDMA) | 40 parts by weight |
| Camphorquinone | 1 part by weight |
| Ethyl p-N,N-dimethylaminobenzoate | 1 part by weight |
| Ultrafine particle silica (resin component-viscosity increasing agent) | 8 parts by weight |

Each 350 parts by weight of the silane-treated inorganic filler 1 obtained in Example A-4 or the silane-treated inorganic particle 1 without polysiloxane treatment obtained in Comparative Example A-4 was mixed with 100 parts by weight of the composition A to prepare dental compositions A-1 and A-4, respectively.

Separately, each 426 parts by weight of the silane-treated inorganic filler 2 obtained in Example A-5, the silane-treated inorganic filler 3 obtained in Example A-6, the silane-treated inorganic particle 2 without polysiloxane treatment obtained in Comparative Example A-5 or the silane-treated inorganic particle 3 without polysiloxane treatment obtained in Comparative Example A-6 was mixed with 100 parts by weight of the composition A to prepare dental compositions. A-2, A-3, A-5 and A-6, respectively.

A toothbrush wear test a polishability test, a coloring resistance test and a bending test were performed using each of the dental compositions A-1 to A-6. The results are shown in Table A-2

TABLE A-2

| Example No. | Dental compositions No. | Kind of surface treatment | Average particle size (μm) | Wear weight loss (wt %) | Polish-ability | Coloring resistance (E*ab) | Bending strength (MPa) |
|---|---|---|---|---|---|---|---|
| Example A-7 | A-1 | PS treatment + silane treatment | 1.2 | 0.98 | Better | 4.2 | 129 |
| Example A-8 | A-2 | PS treatment + silane treatment | 3.2 | 0.38 | Better | 4.5 | 133 |
| Example A-9 | A-3 | PS treatment + silane treatment | 7.5 | 0.22 | Worse | 6.2 | 125 |
| Comparative Example A-7 | A-4 | PS non-treatment + silane treatment | 4.0 | 1.43 | Better | 9.7 | 98 |
| Comparative Example A-8 | A-5 | PS non-treatment + silane treatment | 5.6 | 0.56 | Worse | 8.2 | 102 |
| Comparative Example A-9 | A-6 | PS non-treatment + silane treatment | 7.5 | 0.22 | Worse | 7.8 | 105 |

*PS treatment: Polysiloxane treatment of the present invention.

Examples A-10~A-12 and Comparative Examples A-10~A-12

A coloring resistance test was performed using surface-treated fillers prepared in Examples A-4~A-6 and Comparative Examples A-4~A-6. The results are shown in Table A-3.

TABLE A-3

| | Example No. of Filler preparation | Kind of surface treatment | Evaluation of coloring resistance |
|---|---|---|---|
| Example A-10 | Example A-4 | PS treatment + silane treatment | ◯ |
| Example A-11 | Example A-5 | PS treatment + silane treatment | ◯ |
| Example A-12 | Example A-6 | PS treatment + silane treatment | ◯ |
| Comparative Example A-10 | Comparative Example A-4 | PS non-treatment + silane treatment | × |
| Comparative Example A-11 | Comparative Example A-5 | PS non-treatment + silane treatment | × |
| Comparative Example A-12 | Comparative Example A-6 | PS non-treatment + silane treatment | Δ |

*PS treatment: Polysiloxane treatment of the present invention.

By inclusion of the inorganic filler of the present invention as a filler in a dental composition, the excellent wear resistance and the excellent smoothness and glossiness can be imparted thereto without deteriorating other properties required as a dental composition.

(5) A Fluoride Release Test

An Object of Evaluation

To evaluate the fluoride releasability of a dental composition test sample.

A Method of Evaluation

A dental composition prepared was filled in a stainless mold (15φ×1 mm): disc shape). Glass covers were placed on both sides and it was pressed with a glass plate, then the dental composition was cured by irradiating the light at five positions per test sample for 30 seconds using a photopolymerization irradiating machine (Griplight II: manufactured by Shofu Inc.). After curing, the cured product was removed from the mold, which was used as a test sample. This test sample was placed in a plastic vessel containing 5 ml of distilled water, and was allowed to stand in a constant-temperature bath at 37 C for one day after sealed. After one-day standing, the test sample was removed and put in fresh distilled water. The aforementioned procedures were repeated for 90 days and an amount of an accumulated release value was measured. An amount of fluoride which had dissolved out was determined by using a fluoride-ion multiple electrode (Model 96-09: manufactured by Orion Research Inc.) and an ion meter (Model 720A: manufactured by Orion Research Inc.). At the measurement, 0.5 ml of TISAB III (manufactured by Orion Research Inc.) was added as an ionic strength adjusting agent. In addition, a calibration curve was made by using standard solutions at 0.02, 0.1, 1, 10, and 50 ppms.

(6) Measurement of the Light Transmitted Distribution

An Object of Evaluation

To evaluate the characteristic in diffusion distribution of the transmitted light through a dental composition test sample.

A Method of Evaluation

A dental composition prepared was filled in the stainless mold (15φ×1 mm÷: disc shape). Glass covers were placed on both sides and it was pressed with a glass plate, then the dental composition was cured by irradiating with the light at five positions per test sample for 30 seconds using a photopolymerization irradiating machine (Griplight II: manufactured by Shofu Inc.). After curing, the cured product was removed from the mold, and ground with sandpaper of #600 and #1200 to adjust the thickness to 0.8 mm, which was used as a test sample. Then, the surface of the test sample was planished by buffing and, thereafter, the test sample was set on a measuring jig for a Goniophotometer (GP-200: manufactured by Murakami Shikisai Gijutsu Laboratory) to measure a distribution of the luminous intensity of the transmitted light.

The measurement data (FIG. 1) show a distribution of the intensity of transmitted light over a range of +90 deg~−90 deg from a direction of the incident light as a center.

(7) A Bending Test

An Object of Evaluation

To evaluate the bending strength of a dental composition test sample.

A Method of the Evaluation

A dental composition prepared was filled in a stainless mold (25×2×2 mm: rectangular parallelepiped-shape). Then, glass covers were placed on both sides and it was pressed with a glass plate, then the dental composition was cured by irradiating with the light at five positions per test sample for 30 seconds using a photopolymerization irradiating machine (Griplight II: manufactured by Shofu Inc.). After curing, the cured product was removed from the mold and the other side was irradiated with the light similarly which was used as a test sample. After the test sample was immersed in water at 37 C for 24 hours a bending test was carried out at a distance between supports of 20 mm and a crosshead speed of 1 mm/minute using an Instron type universal tester (Instron 5567 manufactured by Instron Inc.).

(8) A Polishability Test

An Object of Evaluation

To evaluate the surface lubiricity of a dental composition test sample.

A Method of Evaluation

A dental composition prepared was filled in a stainless mold (4φ×6 mm: cylindrical shape). Glass covers were placed on both sides of the mold and it was pressed with a glass plate, then the dental composition was cured by irradiating with the light from both sides (one side: 30 seconds) using a photopolymerization irradiating machine (Griplight II: manufactured by Shofu Inc.). After curing, the cured product was removed from the mold, and was polished using successively Silicon Point (manufactured by Shofu Inc.) and One Gloss Super Buff (manufacture by Shofu Inc.). Then the situation of the polished surface was evaluated with naked eyes. The test was performed by using ten samples and evaluated comprehensively.

(9) A Durability Test

1. A Toothbrush Wear Test After a Long-term Immersion in Water

An Object of Evaluation

To evaluate the wear resistance of a dental composition test sample after immersed in water for a long term.

A Method of Evaluation

A dental composition prepared was packed in four stainless molds (rectangular molds of 15×15×2.6 mm and 25×15×2.6 mm) separately for a toothbrush wear test. Glass covers were placed on both sides and it was pressed by with a glass plate, then the dental composition was cured by irradiating with the light at six positions per test sample for 30 seconds using a photopolymerization irradiating machine (Griplight II: manufactured by Shofu Inc.). After curing, the cured products were removed from the molds, and sequentially polished with sandpaper of #600 and #1200 to adjust the thickness thereof to 2.5 mm, which was used as a test sample (rectangular samples of 15×15×2.5 mm and 25×15× 2.5 mm). Then, the surface of a test sample was planished by buffing, followed by immersing in water at 37 C for 3 weeks. The weight of the test samples were measured, then the test sample was set on the toothbrush wear test machine to performed the toothbrush wear test of 30000 cycles (about three hours) using a toothbrush (Perio H: manufactured by Sunstar Inc.) and toothpaste (White: manufactured by Sunstar Inc.). The weight loss (wt %) was calculated from (a weight loss of the test sample due to wear/the weight of the test sample before wear)×100. Additionally, the test was preformed with four samples and the average of the four measurements was evaluated.

2. A Bending Test After a Long-term Immersion in Water

The Object of Evaluation

To evaluate a bending strength of a dental composition test sample after immersed in water for a long term.

The Method of Evaluation

A dental composition prepared was filled in a stainless mold (25×2×2 mm: rectangular parallelepiped-shape). Then, glass covers were placed on both sides and it was pressed by with a glass plate, then the dental composition was cured by irradiating with the light at five positions per test sample for 30 seconds using a photopolymerization irradiating machine (Griplight II: manufactured by Shofu Inc.). After curing, the cured product was removed from the mold and the other side was irradiated with the light similarly, which was used as a test sample. After the test sample was immersed in water at 37 C for 3 week, a bending test was carried out at a distance between supports of 20 mm and a crosshead speed of 1 mm/minute using an Instron type universal tester (Instron 5567, manufactured by Instron Inc.). Additionally, the test was performed by using ten samples, and evaluated with an average value of the ten samples.

Example B of a Multi-functional Filler of the Present Invention (Production of a Raw Material Inorganic Particle)

Respective raw materials were sufficiently mixed at a proportion of 43 parts by weight of silica, 20 parts by weight of aluminium oxide, parts by weight of sodium fluoride, 10 parts by weight of calcium fluoride, 5 parts by weight of calcium phosphate and 17 parts by weight of strontium carbonate, and the mixture was placed in a high-temperature electronic furnace at 1400 C and a temperature was held to melt the raw materials. After melting cooling afforded a glass as a raw material for a filler, The produced glass was milled by a ball mill for 12 hours and passed through a #200 mesh sieve to obtain a raw material inorganic particle. An average particle size of the raw material inorganic particle was approximately 10 μm.

Example B-1

Preparation of "Multi-functional Filler 1"

(Wet-grinding)

After 4 kg of alumina boulder having a diameter of 6 mm φ was placed in an alumina pot of a tetraplex oscillating mill (internal volume 3.6 L), 540 parts by weigth of the above obtained raw material inorganic particle and 1,000 parts by weight of ion-exchanged water were placed therein, respectively, and the mixture was wet-ground for 15 hours. After grinding, an average particle size and a particle size distribution of the ground slurry were measured by a laser diffraction particle size measuring machine ("Microtrack SPA" manufactured by Nikkiso Inc.). The results of the measurement showed an average particle size of 3.2 μm and monodisperse particle size distribution. Furthermore, after grinding, the alumina boulder and the ground slurry in the alumina pot were separated to give "ground slurry 1".
(Polysiloxane Treatment)

1,500 parts by weight of the above obtained "ground slurry 1" and 21.7 parts by weight of a low-condensed product of a silane compound "MS51SG1" ($SiO_2$ content 16%, degree of polymerization 2~6; manufactured by Mitsubishi Chemical Inc.) were added to a universal mixer and mixed for approximately 90 minutes. After mixed for the predetermined period of time, the treated slurry obtained was aged in a heat dryer at 50 C for 40 hours and, afterward, a temperature was raised to 150 C and held for 6 hours, followed by cooling to obtain the heat-treated solidified material. The heat-treated solidified material obtained was placed in a Henschel mixer and disintegrated at 1800 rpm for 5 minutes. After disintegration, "inorganic particle 1" having a better fluidity havinaving a surface covered with polysiloxane was obtained. A An average particle size and a particle size distribution of this pounder particle were measured using a laser diffraction particle size measuring machine (Microtrack SPA: manufactured by Nikkiso Inc.) and the results showed an average particle size of 3.2 $\mu$m and monodisperse particle size distribution.

(Acidic Polymer Treatment)

2,500 parts by weight of "inorganic filler 1" obtained above was placed into a Henschel mixer, and 575 parts by weight of an aqueous poly(acryl acid) solution (polymer concentration 13 wt %, weight-average molecular weight 20,000; manufactured by Nacalai Tesque Inc.) was sprayed from the above while stirring. After spraying, the particle taken out from a Henschel mixer was heated at 100 C in a heat dryer for 3 hours. After cooling, 500 parts by weight of the resulting particle was placed into the Henschel mixer and stirred, a solution prepared by dissolving 60 parts by weight of γ-methacryloyloxypropyltrimethoxysilane, a silane coupling agent, in 60 parts by weight of ethanol was sprayed while stirring. After spraying, the particle taken out from the Henschel mixer was heated at 100 C in a heat dryer for 3 hours to give "multi-functional filler 1" treated with poly (acrylic acid), which is an inorganic filler of the present invention. A An average particle size and a particle size distribution of this filler were measured by using a laser diffraction particle size measuring machine (Micro Track; manufactured by Nikkiso Co., Ltd.) and the results showed an average particle size of 3.2 $\mu$m and a monodisperse particle size distribution.

Example B-2

Preparation of "Multi-functional Filler 2"

(Wet-grinding)

After 4 kg of alumina boulder having a diameter of 6 mm φ was placed in an alumina pot of a tetraplex oscillating mill (internal volume 3.6 L), 540 parts by weight of the above obtained raw material inorganic particle and 1,000 parts by weight of ion-exchanged water were added therein, respectively and the mixture was wet-ground for 8 hours. After grinding, an average particle size and a particle size distribution of the ground slurry were measured by a laser diffraction particle size measuring machine ("Microtrack SPA" manufactured by Nikkiso Inc.). The results of the measurement showed an average particle size of 7.3 $\mu$m and a monodisperse particle size distribution. Furthermore, after grinding, the alumina boulder and the ground slurry in the alumina pot were separated to obtain "ground slurry 2".

(Polysiloxane Treatment)

1,500 parts by weight of the above obtained "ground slurry 2" and 10.8 parts by weight of a low-condensed product of a silane compound "MS51SG1" ($SiO_2$ content 16%, degree of polymerization 2~6; manufactured by Mitsubishi Chemical Inc.) were added to a universal mixer and mixed for approximately 90 minutes. After mixed for the predetermined period of time, the treated slurry obtained was aged in a heat dryer at 50 C for 40 hours and, therefor, a temperature was raised to 150 C and held for 6 hours, followed by cooling to obtain the heat-treated solidified material The heat-treated solidified material obtained was placed in a Henschel mixer and disintegrated at 1800 rpm for 5 minutes. After disintegration, "inorganic particle 2" having a better fluidity and having a surface covered with polysiloxane was obtained. A An average particle size and a particle size distribution of this filler was measured by using a laser particle size measuring machine (Microtrack SPA: manufactured by Nikkiso Inc.) and the results showed an average particle size of 7.3 $\mu$m and a monodisperse particle size distribution.

(Acidic Polymer Treatment)

2,500 parts by weight of "inorganic particle 2" obtained above was placed in a Henschel mixer, and 575 parts by weight of an aqueous poly(acryl acid) solution (polymer concentration 13 wt %, weight-average molecular weight of 20,000; manufactured by Nacalai Tesque Inc.) was sprayed from the above while stirring. After spraying, the particle taken out from the Henschel mixer was heated at 100 C in a heat dryer for 3 hours. After cooling, 500 parts by weight of the resulting particle was placed in a Henschel mixer and stirred, and a solution prepared by dissolving 60 parts by weight of γ-methacryloyloxypropyltrimethoxysilane, a silane coupling agent, in 60 parts by weight of ethanol was sprayed while stirling. After spraying, the particle taken out from the Henschel mixer was heated at 100 C in a heat dryer for 3 hours to obtain "multi-functional filler 2" treated with poly(acrylic acid), which is an inorganic filler of the present invention. An average particle size and a particle size distribution of this powder filler were measured by using a laser diffraction particle size measuring machine (Micro Track; manufactured by Nikkiso Co., Ltd.) and the results showed an average particle size of 7.3 $\mu$m and a monodisperse particle size distribution.

Example B-3

Preparation of a Multi-functional Filler 1-Containing Composition

Resin composition A was prepared according to the following formulation:

| | |
|---|---|
| 2,2-Bis(4-(3-methacryloyloxy-2-hydroxypropoxy) phenyl)propane (Bis-GMA) | 60 parts by weight |
| Triethyleneglycol dimethacrylate (TEGDMA) | 40 parts by weight |
| Camphorquinone | 1 part by weight |
| Ethyl p-N,N-dimethylaminobenzoate | 1 part by weight |
| Ultrafine particle silica (a resin component viscosity increasing agent) | 8 parts by weight |

Figure 2:
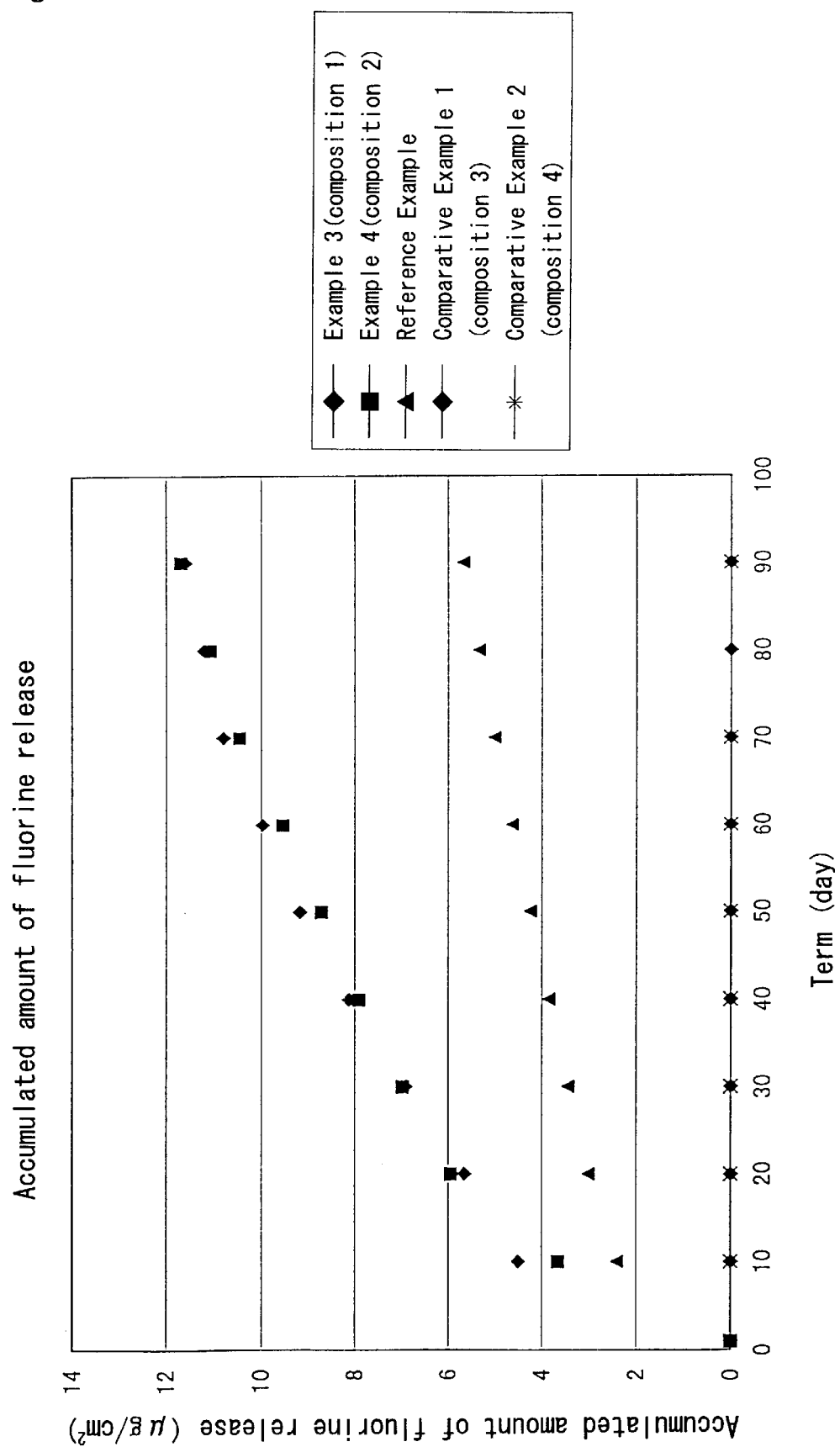
FIG. 2 is a graph showing an accumulated amount of fluoride release.

Dental composition B-1 was prepared in which 350 parts by weight of "multi-functional filler 1" obtained in Example B-1 was incorporated to 100 parts by weight of composition A. The composition B-1 was cured according to the above evaluation method, and a fluoride release test, a bending test, a polishability test, a durability test and a measurement of the light transmitted distribution were carried out. The measurement results of a distribution of the transmitted light are shown in FIG. 1(a), the results of fluoride release test are shown in FIG. 2 and the results of a bending test, a polishability test and a durability test are shown in Table B-1.

Example B-4

Preparation of a Multi-functional Filler 2-Containing Composition

Composition B-2 was prepared according to the same manner as that in Example B-3, but using "multi-functional filler 2" instead of "multi-functional filler 1". The composition B-2 was cured according to the above evaluation method, and a fluoride release test, a bending test, a polishability test, a durability test were carried out. The results of a fluoride release test are shown in FIG. 2, and the results of a bending test, a polishability test and a durability test are shown in Table B-1.

Comparative Example B-1

Composition B-3 was prepared according to the same manner as that in Example B-3, but using as a filler "inorganic particle 1" obtained by subjecting a polysiloxane—treated particle "inorganic particle 1" before treating with an acidic polymer in Example B-1, which treated with silane in Example B-1 instead of "multi-functional filler 1". A fluoride release test, a bending test, a polishability test, a durability test and a measurement of the light transmitted distribution were carried out as in composition 1 in Example B-3. The results of measurement of distribution of the transmitted light are shown in FIG. 1(b), and the results of the a fluoride release test are shown in FIG. 2, and the results of a bending test, a polishability test and a durability test are shown in Table B-1.

Comparative Example B-2

Composition B-4 was prepared according to the same manner as that in Example B-3, but using as a filler "inorganic particle 2" obtained by subjecting a polysiloxane-treated particle "inorganic particle 2" before treating with an acidic polymer in Example B-2, which was treated with silane in Example B-2 instead of "multi-functional filler 2". A fluoride release test, a bending test, a polishability test and a durability test were carried out as in composition B-2 of Example B-4, and tfie results of the fluoride release test are shown in FIG. 2, and the results of a bending test, a polishability test and a durability test are shown in Table B-1.

Reference Example

A commercially available fluoride-releasable compomer, Dyract AP (manufactured by Dentsply Ltd.) was cured according to the above evaluation method, and a fluoride release test, a bending test, a polishability test and a durability test were carried out, and the results of a fluoride release test are shown in FIG. 2, and the results of a bending test, a polishability test and a durability test are shown in Table B-1

TABLE B-1

| Example No. | Dental composition No. | Polishability test | Bending test (MPa)*1 | Durability test | |
|---|---|---|---|---|---|
| | | | | Bending test after immersed in water for a long term (MPa)*2 | Toothbrush wear test after immersed in water for a long term (weight loss %)*2 |
| Example B-3 | B-1 | Good | 133 | 125 | 0.25 |
| Example B-4 | B-2 | Good | 135 | 126 | 0.33 |
| Comparative Example B-1 | B-3 | Good | 136 | 130 | 0.58 |
| Comparative Example B-2 | B-4 | Good | 138 | 122 | 0.43 |
| Reference Example | Dyract AP (Dentsply) | Poor | 118 | 87 | 3.53 |

*1 37 C, immersed in water for 24 hours
*2 37 C, immersed in Water for 3 weeks

Inclusion of a multi-functional filler of the present invention as a filler can impart the excellent distribution of the transmitted light (a uniform directional distribution of the transmitted light) and sustained fluoride releasbility to a dental composition without deteriorating other necessary properties for a dental composition.

(10) A Bending Test

An Object of Evaluation

To evaluate the bending strength and the bending modulus of a dental composition test sample.

A Method of Evaluation

A dental composition prepared was filled in a stainless mold (25×2×2 mm; parallelepiped-shape). Then, glass coveare covers were placed on both sides and it was pressed by with a glass plate, then the dental composition was cured by irradiating with the light at five positions per sample for 30 seconds using a photopolymerization irradiating machine (Griplight II: manufactured by Shofu Inc.) After curing, the cured product was removed from the mold and the other side was irradiated with the light similarly, which was used as a test sample. The test sample was immersed in water at 37 C for 24 hours, then it was subjected to a bending test.

The measurement of the bending test was performed by Instron type universal tester (Instron 5567, manufactured by Instron Inc.) at a distance between supports of 20 mm and a crosshead speed of 1 mm/min.

Additionally, the test was performed by using 10 test samples, and evaluated with an average value of 10 samples.

(11) A Bending Test After a Long-term Immersion in Water

An Object of Evaluation

To evaluate the bending strength or both the bending strength and the bending modulus of a dental composition test sample after immersion in water for a long term.

A Method of Evaluation

A dental composition prepared was filled in a stainless mold (25×2×2 mm; rectangular parallelepiped-shape). Then, glass covers were placed on both sides and it was pressed with a glass plate, then the dental composition was cured by irradiating with the light at five positions of one side per sample for 30 seconds using a photopolymerization irradiating machine (Griplight II: manufactured by Shofu Inc.) After curing, the cured product was removed from the mold and the other side was similarly irradiated with light, which was used a test sample. The test sample was immersed in water at 37 C for one month, then it was subjected to the bending test.

The measurement of the bending test was performed by Instron type universal tester (Instron 5567, manufactured by Istron Inc.) at a distance between supports of 20 mm and a crosshead speed of 1 mm/min.

Additionally, the test was performed by using 10 test samples, and evaluated with an average value of 10 samples.

Example C of an Organic Compound Filler of the Present Invention

Example C-1
(Preparation of an Organic-inorganic Polymer Particle A)

According to the conventional process, an ultrafine particle silica (Nippon Aerosil, Inc.: Trade name: Aerosil OX-50) was treated with 8 parts by weight of γ-methacryloyloxypropyltrimethoxysilane (hereinafter abbreviated to as "γ-MPS") to form an ultra fine particle filler.

Next, 50 parts by weight of the above ultrafine particle silica was mixed with 50 parts by weight of a mixture of 70 parts by weight of N,N'-(2,2,4-trimethylhexamethylene)-bis ([2-(aminocarboxy)ethanol]methacrylate (hereinafter abbreviated to as "UDMA"), 30 parts by weight of triethyleneglycol dimethacrylate (hereinafter abbreviated to as "TEGDMA"), and 0.5 parts by weight of benzoyl peroxide (hereinafter abbreviated to as "BPO"), and the mixture was kneaded uniformly. Then, it was heated to cure at 100 C for 24 hours under a nitrogen atmosphere, and was ground and classified to give an organic-inorganic polymer particle A having an average particle size of 22 μm.
(Formation of an Inorganic Film)

After 700 parts by weight of ethanol, 100 parts by weight of distilled water and a small amount of hydrochloric acid were placed into a vessel of T. K. HIVIS MIX, 150 parts by weight of the above organic-inorganic polymer particle A was placed thereto and stirred uniformly at a temperature of 40~50 C. A 26.0 parts by weight of a low-condensed product of a silane compound (Mitsubishi Chemicals, Trade Name: MS51SG1 (SiO$_2$ content 16%, degree of polymerization 2~6)) was added thereto dropwise to react for 10 hours. After the reaction was completed, ethanol and distilled water were removed, and the residue was heated and disintegrated to give a filler. Further, the surface of this filler was treated with 3 parts by weight of γ-MPS according to the conventional process to give an organic compound filler A modified with inorganic film.
(Preparation of a Dental Composition)

65 parts by weight of organic compound filler A, and 5 parts by weight of a ultrafine particle silica as a filler were mixed with 30 parts by weight of a resin composition comprising 70 parts by weight of UDMA, 30 parts by weight of TEGDMA, 0.3 part by weight of camphorquinone (hereinafter abbreviated to as "CQ"), and 2 parts by weight of ethyl p-N,N-dimethylaminobenzoate (hereinafter abbreviated to as "DMABE"), and the mixture was kneaded to prepare a pasty dental composition C-1.

Example C-2

Organic compound filler B was obtained according to the same manner as that in Example C-1, except that upon formation of an inorganic film of Example C-1, 4.3 parts by weight of γ-MPS was added in addition to the low-condensed product of a silane compound. Further, this surface-modified organic compound filler B was used to prepare a pasty dental composition C-2 as in Example C-1.

Example C-3

Organic compound filler C was obtained according to the same manner as that in Example C-1, except that upon formation of an inorganic film of Example C-1, 10.7 parts by weight of zirconium n-propoxide (Matsumoto Seiyalcu Kogyo, Trade Name: Orgatics ZA-40 (ZrO$_2$ total content 28.0%)) was added in addition to a low condensate low-condensed product of a silane compound. Further, this surface-modified organic compound filler C was used to prepare a pasty dental composition C-3 as in Example C-1.

Example C-4
(Preparation of an Organic-inorganic Polymer Particle B)

According to the conventional process, the surface of a barium boroaluminosilicate glass having an average particle size of 1 μm (Schott Glaswerke, Mainz, Germany, Trade name: GM-27884) was treated with 9 parts by weight of γ-MPS to form a barium glass filler.

Next, 50 parts by weight of the above barium glass filler was added to 50 parts by weight of a mixture of 70 parts by weight of UDMA, 30 parts by weight of TEGDMA, and 0.5 parts by weight of BPO, and the mixture was kneaded uniformly. Then, it was heated to cure at 100 C for 24 hours under a nitrogen atmosphere, and was ground and classified to give an organic-inorganic polymer particle B having an average particle size of 22 μm.
(Formation of an Inorganic Film)

After 700 parts by weight of ethanol, 100 parts by weight of distilled water and a small amount of hydrochloric acid were placed into a vessel of T. K. HIVIS MIX, 150 parts by weight of the above organic-inorganic polymer particle B was placed thereto and stirred uniformly at a temperature of 40~50 C. 26.0 parts by weight of a low-condensed product of a silane compound (Mitsubishi Chemicals, Trade name: MS51SG1 (SiO$_2$ content 16%, degree of polymerization 2~6)) was added dropwise to react for 10 hours. After the reaction was completed, ethanol and water were removed, and the residue was heated and disintegrated to give a filler. Further, the surface of this filler was treated with 3 parts by weight of γ-MPS according to the conventional process to give an organic compound filler D.
(Preparation of a Dental Composition)

65 parts by weight of the organic compound filler D, and parts by weight of a ultrafine particle silica as filler were mixed with 30 parts by weight of a resin composition containing 60 parts by weight of 2,2-bis(4-(3-methacryloyloxy-2-hydrxypropoxy)phenyl)propane (hereinafter abbreviated to as "Bis-GMA), 40 parts by weight of TEGDMA, 0.3 parts by weight of CQ, and 2 parts by weight of DMABE, and the mixture was kneaded to prepare a pasty dental composition C-4.

Example C-5

Organic compound filler E was obtained according to the same manner as that in Example C-4, except that an amount of the silane compound used upon formation of an inorganic film of the Example C-4 was 39.0 parts by weight and that 16.1 parts by weight of zirconium n-propoxide (Matsumoto Seiyaku Kogyo, Trade Name: Orgatics ZA-40 (ZrO$_2$ total content 28.0%) was added. Further, this surface-modified organic compound filler E was used to prepare a pasty dental composition C-5 as in Example C-4.

Comparative Examples C-1 and C-2

By using the organic-inorganic polymer particles A and B prepared in Examples C-1 and C-2, surface treatment was carried out with 3 parts by weight of γ-MPS according to the conventional process to give silane-treated organic-inorglanic polymer particles 1 and 2. These fillers were used to prepare pasty dental compositions C-6 and C-7 as in Examples C-1 and C-4.

A bending test and a durability test (a bending test after immersion in water for a long term) were performed by using the pasty dental compositions C-1~C-7 prepared above. Results are shown in Table C-1.

(3) A Polishability Test

An Object of Evaluation

To evaluate the surface smootb hness and glossiness of a dental composition test sample.

A Method of Evaluation

A dental composition prepared was filled in a stainless mold (4ϕ×6 mm: cylinderical shape), glass covers were placed on the both sides and it was pressed with a glass plate. The dental composition was cured by irradiating with the light from both sides (one side: 30 seconds) using a photo-

TABLE C-1

| Example No. | Dental composition No. | The present organic compound filler No. | Bending test | | Durability test (Bending test after immersed in water for a long-term) | |
|---|---|---|---|---|---|---|
| | | | Bending strength MPa | Bending modulus GPa | Bending strength MPa | Bending modulus GPa |
| Example C-1 | C-1 | A | 115 | 9.3 | 109 | 9 |
| Example C-2 | C-2 | B | 110 | 10.0 | 103 | 9.8 |
| Example C-3 | C-3 | C | 109 | 8.9 | 108 | 8.5 |
| Example C-4 | C-4 | D | 118 | 9.8 | 115 | 9.4 |
| Example C-5 | C-5 | E | 105 | 8.0 | 99 | 7.9 |
| Comparative Example C-1 | C-6 | organic-inorganic polymer particle 1 | 60 | 4.6 | 49 | 4.0 |
| Comparative Example C-2 | C-7 | organic-inorganic polymer particle 2 | 72 | 5.1 | 55 | 4.5 |

In a dental composition, inclusion of the organic compound filler of the present invention as a filler can impart the excellent polishability, particularly the properties of the surface smoothness and glossiness and the like, as well as the excellent mechanical strength, the durability and the stable handling.

(12) A Toothbrush Wear Test

An Object of Evaluation

To evaluate wear resistance of a dental composition test sample.

A Method of Evaluation

A dental composition prepared was filled in four stainless molds (rectangular molds of 15×15×2.6 mm and 25×15×2.6 mm) separately for a toothbrush wear test. Glass covers were placed on both sides, and it was pressed with a glass plate, then the dental composition was cured by irradiating with the light at six positions per test sample for 30 seconds using a photopolymerization irradiating machine (Griplight II: manufactured by Shofu Inc.). After curing, the cured product was removed from the mold and polished successively with sandpaper of #600 and #1200 to adjust the thickness thereof to 2.5 mm, which was used as a test sample (rectangular samples of 15×15×2.5 mm and 25×15×2.5 mm). Then, the surface of the test sample was planished by buffing, followed by measuring the weight thereof. After that, the test sample was mounted on a toothbrush wear test machine to perform a toothbrush wear test of 30000 cycles (about 3 hours) using a toothbrush (Perio H: manufactured by Sunstar Inc.) and toothpaste (White: manufactured by Sunstar Inc.). A weight loss (wt %) was calculated from (a weight loss of the test sample due to wear/a weight of the test sample before wear)×100. Additionally, the test was carried out on four samples and evaluation was performed using an average of the four measurements.

polymerization irradiating machine (Griplite II: manufactured by Shofu Inc.). After curing, the cured product was removed from the mold, which was used as a test sample. The test sample was polished using successively Silicon Point (manufactured by Shofu) and a One Gloss Superbuff (manufactured by Shofu) and the situation of the polished surface was evaluated with naked eyes. The test was carried out on ten samples and evaluated comprehensively.

(14) A Coloring Resistance Test

An Object of Evaluation

To evaluate the coloring resistance of a dental composition test sample and

A method of Evaluation (1) A dental composition prepared was filled in a stainless mold (15ϕ×1 mm: disk), glass covers were placed on the both sides and it was pressed with a glass plate. The dental composition was cured by irradiating with the light at six positions for 30 seconds using a photopolymerization irradiating machine (Griplite II: manufactured by Shofu). After curing, the cured product was removed from the mold, both surfaces were slightly polished using sandpaper #1200 to remove a resin layer, which was used as a test sample. Thereafter, the color of the test sample was measured using a spectrocolorimeter (CM-2000, manufactured by Minolta), and immersed into a 5.0% aqueous solution of instant coffee (Nescafe) at 37 C for 24 hours. After immersed for 24 hours, the test sample was removed, washed with water, and the color was measured again. Color difference (E*ab) was calculated by measured color values before and after immersion. The test was carried out on five samples and evaluated using an average of five measurements.

(2) Each 5 g of the surface treated fillers prepared in Examples D-6~) D-11 and Comparative Examples D-3 and D-4 was immersed in a 5.0% aqueous solution of instant coffee (Nescafe) at 37 C for 24 hours. After immersion for 24 hours, the inorganic filler was filtrated, and a degree of coloration was evaluated based on the following criteria.

o: Slightly colored

Δ: Heavily colored

X: Remarkably colored

(15) A Bending Test

An Object of Evaluation

To evaluate the bending strength or both bending strength and bending modulus of a dental composition test sample.

A Method of Evaluation

A dental composition prepared was filled in a stainless mold (25×2×2 mm: rectangular parralleopiped), glass covers were placed on the both sides and it was pressed with a glass plate. The dental composition was cured by irradiating with the light at five positions for 30 seconds using a photopolymerization irradiating machine (Griplite II: manufactured by Shofu Inc.). After curing, the cured product was removed from the mold and the other side was irradiated with the light similarly, which was used as a test samples. After the test sample was immersed into water at 37° C. for 24 hours, a bending test was carried out. A bending test was carried out at a distance between supports of 20 mm and a crosshead speed of 1 mm/min. using an Instron test machine (Instron 5567, manufactured by Instron). Additionally, the test was performed by using 10 samples, and evaluated with an average value of the 10 samples.

Example D of a Modified Filler of the Present Invention (Preparation of a Raw Material Inorganic Particle)

Respective raw materials were mixed well at a proportion of 43 parts by weight of silica, 20 parts by weight of aluminium oxide, 5 parts by weight of sodium fluoride, 10 parts by weight of calcium fluoride, 5 parts by weight of calcium phosphate and 17 parts by weight of strontium carbonate, the mixture was placed in a high temperature electric furnace at 1400° C. and the temperature held for 5 hours to melt raw materials. After melted, cooling afforded a glass as a raw material for a filler. The prepared glass was ground for 12 hours with a ball mill, and passed through a #200 mesh sieve to obtain a raw material inorganic particle for wet-grinding. An average particle size of a raw material inorganic particle was about 10 μm.

Example D-1

Preparation of Polyorganosiloxane-covered Inorganic Filler "Silane-treated Modified Filler 1"

(Wet-grinding)

After 4 kg of alumina boulder having a diameter of 6 mm φ was placed in an alumina pot of a tetraplex oscillating mill (internal volume 3.6 L), 540 parts by weight of a raw material inorganic particle obtained above and 1,000 parts by weight of ion-exchanged water were placed therein, respectively, and the mixture was wet-ground for 40 hours.

After grinding, an average particle size and a particle size distribution of the ground slurry was measured using a laser diffraction particle size measuring machine ("Microtrack SPA"; manufactured by Nikkiso). The results showed an average particle size of 1.2 μm and a monodisperse particle size distribution. After grinding, the alumina boulder and the ground slurry in the alumina pot were separated to obtain "ground slurry 1".

(Formation of a Polyorganosiloxane Film: POS Treatment)

After 1,500 parts by weight of "ground slurry 1" was placed in a container of T.K. COMBIMIX and held at 50 C, 54.1 parts by weigh of a low-condensed product of a silane compound "MS51SG1" ($SiO_2$ content 16%, polymerization degree 2~6; manufactured by Mitsubishi Chemical Inc.) and 8.7 parts by weight of γ-methacryloyloxyproplytrimethoxysilane were added, respectively, and the mixture was stirred to mix for about 90 minutes. After mixing, the resulting treated slurry was aged in a heat dryer at 50 C for 40 hours, a temperature was raised to 120° C. and held for 6 hours, which was cooled followed by cooling to obtain a heat-treated solidified material. The resulting heat-treated solidified material was placed in a Hemschel mixer and disintegrated at 1800 rpm for 5 minutes to obtain "modified filler 1" having the surface covered with polyorganosiloxane. The fluidity of modified filler 1 at this disintegration was evaluated and, at the same time, an average particle size and a particle size distribution were measured using a laser diffraction particle size measuring machine. As a result, the fluidity of a filler was better, an average particle size was 1.2 μm and a monodisperse particle size distribution was shown. The resulting "modified filler 1" covered with polyorganosiloxane was further subjected to 9 parts by weight silane-treatment using γ-methacrolyloxypropyltrimethoxysilane which is an organosilane compound to obtain "silane-treated modified filler 1".

Examples D-2 and D-3

According to the same manner as that of Example D-1 except that γ-methacryloyloxypropyltrimethoxysilane used in the POS treatment in Example D-1, was used at an amount of 17.4 parts by weight and 26.1 parts by weight, respectively, silane-treated modified fillers 2 and 3 were obtained.

Example D-4

According to the same manner as that of Example D-1 except that 14.3 parts by weight of methyltriethoxysilane was used instead of γ-methacryloyloxypropyltrimethoxysilnane used in the POS treatment in Example D-1, a silane-treated modified filler 4 was obtained.

Example D-5

Preparation of a Polyorganosilane-covered Inorganic Filler, "Silane-treated Modified Filler 5"

According to the same manner as that of Example D-1 except that a grinding time was 8 hours in wet-grinding of Example D-1, a "ground slurry 2" which is an aqueous dispersion was obtained. An average particle size and a particle size distribution were measured using a laser diffraction particle size measuring machine ("Microtrack SPA"; manufactured by Nikkiso Co. Ltd.). The results showed an average particle size of 3.2 μm and a monodispersed particle size distribution.

(Formation of a Polyorganosiloxane Film: POS Treatment)

1,500 parts by weight of a "ground slurry 2" was placed in a container of T.K. COMBIMIX and 54.1 parts by weight of a low-condensed product of a silane compound "MS51SG1" (SiO₂ content 16%, polymerization degree 2~6; manufactured by Mitsubishi Chemical Inc.) and 8.7 parts by weight of γ-methacryloyloxypropyltrimethoxysilane were added, respectively, and the mixture was stirred to mix for about 90 minutes. After mixing, the resulting treated slurry was aged in a heat dryer at 50° C. for 40 hours, a temperature was raised to 150° C. and held for 6 hours, which was followed by cooling to obtain a heat-treated solidified material. The resulting heat-treated solidified material was placed in a Henschel mixer and disintegrated at 1800 rpm for 5 minutes to obtain "modified filler 5" having a surface covered with polyorganosiloxane. The fluidity of the modified filler 5 at disintegration was evaluated and at the same time an average particle size and a particles size distribution were measured using a laser diffraction particle size measuring machine "Microtrack SPA". The results showed the fluidity of a filler was better, an average particle size was 3.3 μm and a monodispersed particle size distribution. The resulting modified filler 5 was ftherter subjected 6 parts by weight silane treatment using γ-methacryloyloyxypropyltrimethoxysilane which is an organosilane compound to obtain a silane-treated modified filler 5.

Comparative Examples D1 and D-2

Respect ive ground slurry 1 and 2 obtained by wet-grinading in Example D-1 and D-5 were aged in a heat dryer at 50° C. for 40 hours without performing the polyorganosilane treatment, a temperature was raised to 120° C. and held for 6 hours, which were followed by coolina to obtain a heat-treated solidified material. The resulting heat-treated solidified material was placed in a Henschel mixer, and disintegrated at 1800 rpm for 5 minutes to obtain inorganic particle 1 and 2 without POS treatment. The fluidity of inorganic particle 1 and 2 without POS treatment at this disintegration was evaluated and, at the same time, an average particle size and a particle size distribution were measured using a laser diffraction particle size measuring machine "Microtrack SPA". The results thereof are shown in Table D-1. The resulting respective inorganic particle were subjected to 9 parts by weight or 6 parts by weight silane treatment using γ-methacryloyloxypropytrilmethoxysilane which is an organosilane compound, to obtain silane-treated POS non-treated fillers 6 and 7.

TABLE D-1

| Example No. | POS treatment* yes or no | Kind of filler | At wet grinding Average particle size (μm) | At disintegration after POS treatment Average particle size (μm) | Fluidity | Particle size distribution |
|---|---|---|---|---|---|---|
| Example D-1 | Yes | modified filler 1 | 1.2 | 1.2 | Good | Narrow monodispersion |
| Comparative Example D-1 | No | inorganic particle 1 without POS treatment | 1.2 | 4 | Bad | Wide polydispersion |
| Example D-5 | Yes | modified filler 5 | 3.2 | 3.3 | Good | Wide polydispersion |
| Comparative Example D-2 | No | inorganic particle 2 without POS treatment | 3.2 | 4.9 | Bad | Wide polydispersion |

*POS treatment: treatment for forming a polyorganosiloxane film of the present invention.

Examples D-6~D-10 and Comparative Examples D-3 and D-4

A resin composition was prepared according to the following formulation:

| | |
|---|---|
| 2,2-bis(4-(3-methacryloyloxy-2-hydroxypropoxy) phenyl)propane (Bis-GMA) | 60 parts by weight |
| Triethyleneglycol dimethacrylate (TEGDMA) | 40 parts by weight |
| Camphorquinone | 1 part by weight |
| Ethyl p-N,N-dimethylaminobenzoate | 1 part by weight |
| Ultrafine particle silica (resin component viscosity increasing agent) | 18 parts by weight |

Each 296 parts by weight of silane-treated modified fillers 1~4 obtained in Examples D-1~D-4, and a silane-treated inorganic particle 1 without POS treatment obtained in Comparative Example D-1 were incorporated into 100 parts by weight of a resin composition, respectively, to prepare a dental composition D-1~D-4 (Examples D-6~D-9) and a dental composition D-5 (Comparative Examples D-3), respectively.

In addition, each 372 parts by weight of a silane-treated modified filler 5 obtained in Example D-5 and a silane-treated inorganic particle 2 without POS treatment obtained in Comparative Example 18 were incorporated into 100 parts by weight of a resin composition, respectively, to prepare a dental composition D-6 (Example D-10) and a dental composition D-7 (Comparative Example D-4), respectively.

A toothbrush wear test, a polishability test, a coloring resistance test and a bending test were carried out using these dental compositions and the results thereof are shown in Table D-2.

Example D-11

In addition, a dental composition D-8 was prepared at the same amount as that of Examples D-6~D-9 except that a modified filler 1 (silane non-treated) obtained in Example D-1 was used, and various tests were performed. The results thereof are shown in Table D-2.

TABLE D-2

| Example No. | Dental composition No. | Total amount of a filler to be packed (%) | Kind of Filler | Example and Comparative Example of filler preparation | Kind of surface treatment | Resistance of teethbrush wear (wt%) | Polishability | Coloring resistance (E*ab) | Bending strength MPa |
|---|---|---|---|---|---|---|---|---|---|
| Example D-6 | D-1 | 78.5 | silane-treated modified filler 1 | Example D-1 | POS treatment + silane treatment | 0.392 | Good | 4.0 | 129 |
| Example D-7 | D-2 | 78.5 | silane-treated modified filler 2 | Example D-2 | POS treatment + silane treatment | 0.249 | Good | 3.5 | 130 |
| Example D-8 | D-3 | 78.5 | silane-treated modified filler 3 | Example D-3 | POS treatment + silane treatment | 0.222 | Good | 3.2 | 120 |
| Example D-9 | D-4 | 78.5 | silane-treated modified filler 4 | Example D-4 | POS treatment + non silane treatment | 0.25 | Good | 3.0 | 128 |
| Example D-11 | D-8 | 78.5 | modified filler 1 | Example D-1 | POS non-treatment + silane treatment | 0.522 | Good | 6.2 | 98 |
| Comparative Example D-3 | D-5 | 78.5 | inorganic particle 1 without POS treatment | Comparative Example D-1 | POS non-treatment + silane treatment | 0.843 | Good | 9.9 | 98 |
| Example D-10 | D-6 | 82.0 | silane-treated modified filler 5 | Example D-5 | POS treatment + silane treatment | 0.156 | Good | 4.5 | 140 |
| Comparative Example D-4 | D-7 | 82.0 | inorganic particle 2 without POS treatment | Comparative Example D-2 | POS non-treatment + silane treatment | 0.433 | Bad | 6.3 | 119 |

POS treatment: treatment for forming a polyorganosiloxane film of the present invention.

In a dental composition, by incorporating a modified filler of the present invention as a filler, the mechanical strength, the wear resistance and the coloring resistance can be improved while maintaining the excellent optical properties such as the polishability, and the surface smoothness and glossiness.

(15) A Bending Test

An Object of Evaluation

To evaluate the bending strength or both the bending strength and the bending modulus of a dental composition test sample.

A Process of Evaluation

A dental composition prepared was filled in a stainless mold (25×2×2 mm: rectangular parallelepiiped-shape). Then, glass covers were placed on both sides and it was pressed with a glass plate, and the dental composition was cured by irradiating with the light at five positions of one side for each 30 seconds using a photopolymerization irradiating machine (Griplight II: manufactured by Shofu Inc.). After curing, the cured product was removed from the mold and the other side was similarly irradiated with the light, which was used as a test sample. The test sample was immersed in water at 37 C for 24 hours and, thereafter, a bending test was performed. The bending test was performed using an Instron type universal tester (Instron 5567, manufactured by Instron Inc.) at a distance between supports of 20 mm and a crosshead speed of 1 mm/min. Additionally, the test was performed by usin 10 test samples, and evaluated with an average of the 10 samples.

(16) A Depth of Cure Test

An Object of Evaluation

To evaluate a depth of cure of a dental composition test sample.

A Method of Evaluation

A dental composition prepared was filled in a cylindrical-shape stainless mold having a sample filling portion of 4φ×6 mm, then glass covers were placed on both sides and pressed with a glass plate, then the dental composition was cured by irradiating with the light from the upper side for 30 seconds using a photopolymerization irradiating machine (Griplight II: manufactured by Shofu Inc.). After curing, the cured product was removed from the mold, and the non-cured portion was removed to prepare a test sample. A length of the test sample was measured using a micrometer, and the measured value was considered as a depth of cure. Furthermore, each test was performed employing five samples, and evaluation was performed based on an average of five samples.

(17) A Color Tone Changing Test

An Object of Evaluation

To evaluate a color tone change of a dental composition test sample which is influenced by a kneading time.

A Method of Evaluation

A dental composition prepared was filled in a stainless mold (15φ×1 mm: disc shape), then glass covers were placed on both sides and pressed with a glass plate. Then, the dental composition was cured by irradiating with the light at six positions for each 30 seconds using a photopolymerization irradiating machine (Griplight II: Shofu Inc.). After curing, the cured product was removed from the mold, which was used as a test sample. Thereafter, the color tone of the test sample was measured using a spectrocolorimeter (Lab color specification system) (CM-2002; manufactured by Minolta Inc.). A color tone change and a color difference (ΔE*ab) of the dental composition test sample prepared at a kneading time of 2.0 or 4.0 hours relative to the dental composition test sample prepared at a kneading time of 0.5 hour as a standard were calculated and evaluated. Color measurement conditions were as follows. Light source: C light source, Field angle: 2°, Background color: white. Furthermore, each test was performed employing five samples, and evaluation was performed based on an average of five samples.

(18) A Consistency Test

An Object of Evaluation

To evaluate the consistency of a dental composition immediately after preparation and a dental composition stored at 37 C for one month after preparation.

A Method of Evaluation

Each 0.3 ml of a dental composition immediately after preparation and a dental composition stored at 37 C for one month after preparation were weighted, and placed on a glass plate. Thereafter, another glass plate and a load of 385 g were carefully loaded thereon. Long and short diameters of an extended dental composition after 60 seconds were measured through a glass using a section paper, and an arithmetic mean thereof was adopted as the consistency. Furthermore, each test was performed employing five samples, and evaluation was performed based on an average of five samples.

(Preparation of a Raw Material Inorganic Particle)

Respective raw materials were sufficiently mixed at a proportion of 43 parts by weight of silica, 20 parts by weight of aluminium oxide, 5 parts by weight of sodium fluoride, 10 parts by weight of calcium fluoride, 5 parts by weight of calcium phosphate and 17 parts by weight of strontium carbonate, and the mixture was placed in a high-temperature electronic furnace at 1400 C and the temperature was held for 5 hours to melt the raw materials. After melting, cooling afforded a glass as a raw material for a filler. The produced glass was ground by a ball mill for 12 hours and passed through a #200 mesh sieve to obtain a raw material inorganic particle for wet-grinding. An average particle size of a raw material inorganic particle was approximately 10 $\mu$m.

Example E-1

Preparation of a Coloring Filler "Red Filler"

(Preparation of an Inorganic Particle)

After 4 kg of alumina boulder having a diameter of 6 mm $\phi$ was placed in an alumina pot of a tetraplex oscillating mill (internal volume 3.6 L), 540 parts by weight of the raw material inorganic particle obtained above and 1,000 parts by weight of ion-exchanged water were placed, respectively, and the mixture was wet-ground for 40 hours. After grinding, the alumina boulder and the ground slurry in the alumina pot were separated to obtain an "aqueous dispersion containing an inorganic particle".

(Preparation of a Coloring Particle)

750.0 parts by weight of ethanol and then 15.9 parts by weight of colcothar (Tenshojirusi: manufactured by Japan Colcothar Industry Inc.) were weighted and placed in a plastic vessel (1.0 L content) and pre-stirred using a glass rod. Thereafter, a mixture was dispersed using an ultrasonic dispersing machine for 10 minutes to obtain an "aqueous dispersion containing a coloring particle 1" in which the coloring particle was uniformly dispersed.

(Formation of a Poly(organo)siloxane Film)

After 1,500 parts by weight of an "aqueous dispersion containing inorganic particle" and a total amount of an "aqueous dispersion containing a coloring particle 1" were added to a vessel of T. K. COMBIMIX, the mixture was uniformly dispersed using an ultrasonic dispersing machine for 10 minutes to obtain an "aqueous dispersion containing a mixed particle 1" in which each particle was uniformly dispersed. An average particle size and particle size distribution of the mixed particle which was dispersed in an aqueous dispersion were measured using a dynamic light scattering type particle size measuring machine "PAR-IIIs" (manufactured by Otsuka Electronics Inc.), and the results showed an average particle size of 1.2 $\mu$m and a monodisperse particle size distribution. Thereafter, 54.1 parts by weight of a low-condensed product of a silane compound "MS51SG1" ($SiO_2$ content 16%, degree of polymerization 2~6; manufactured by Mitsubishi Chemical Inc.) was added to an aqueous dispersion containing such the mixed particle, and mixed at 50 C for approximately 90 minutes. After mixing, the aqueous dispersion was aged in a heat dryer at 50 C for 40 hours, then a temperature was raised to 120 C and held for 6 hours, followed by cooling to obtain a heat-treated solidified material. The heat-treated solidified material obtained was placed in a Henschel mixer and disintegrated at 1800 rpm for 5 minutes to obtain a coloring filler having the surface covered with poly(organo)siloxane (hereinafter referred to as red filler). In addition to evaluation of the fluidity of a red filler upon disintegration, an average particle size and a particle size distribution of a red filler were measured using a dynamic light scattering type particle size measuring machine "PAR-IIIs". The results showed that the filler has the better fluidity, an average particle size of 1.2 $\mu$m and a monodisperse particle size distribution.

The resulting red filler covered with poly(organo)siloxane was further subjected to 12 parts by weight silane treatment with an organosilane compound, $\gamma$-methacryloyloxypropyltrimethoxysilane, and the treated filler was used for preparing a dental composition.

Examples E-2~E-4

Preparation of Coloring Fillers "Yellow Filler", "Black Filler" and "White Filler"

"Yellow filler", "Black filler" and "White filler" were obtained according to the same manner as that of Example E-1, except that 18.9 parts by weight of yellow iron oxide ("Bayferrox yellow BF-920", manufactured by Bayer AG), 12.6 parts by weight of black iron oxide (OBR-20B manufactured by Japan Colcothar Industry Inc.) and 25.2 parts by weight of titanium oxide (R-820 manufactured by Ishihara Industry Inc.) were used respectively, instead of 15.9 parts by weight of colcothar used in the step of preparing a coloring particle of Example E-1, and they were used for preparing a dental composition.

Comparative Example E-1

Preparation of a Diluted Colorant "Diluted Red"

A "diluted Red" was obtained according to the same manner as that of Example E-1, except that a low-condensed product of a silane compound was not added to an aqueous dispersion containing the mixed particle in a step of forming a poly(organo)siloxane film in Example E-1. In addition to evaluation of the fluidity of diluted red upon disintegration of a heat treated solidified material, an average particle size and a particle size distribution of a diluted red were measured using a dynamic light scattering type particle size measuring machine "PAR-IIIs". The results showed that the filler has the worse fluidity, an average particle size of 4.3 $\mu$m and a polydisperse particle size distribution. A diluted red was treated with silane according to the same manner as that of Example E-1 and was used for preparing a dental composition.

Comparative Examples E-2~E-4

Preparation of Diluted Colorants "Diluted Yellow", "Diluted Black" and "Diluted White"

"Diluted Yellow", "diluted Black" and "diluted White" were obtained according to the same manner as that of Examples E-2~E-4, except that a low-condensed product of a silane compound was not added into an aqueous dispersion containing the mixed particle in a step of forming a poly(organo)siloxane film, and they were used for preparing a dental composition.

Examples E-5~E-8 and Comparative Examples E-5~E-12

Preparation of a Monochromatic Dental Composition

Monochromatic dental compositions (Example E-5 and Comparative Examples E-5 and E-9 relate to a red dental composition, Example E-6 and Comparative Examples E-6 and E-10 relate to a yellow dental composition, Example E-7 and Comparative Examples E-7 and E-11 relate to a black dental composition, and Example E-8 and Comparative Examples E-8 and E-12 relate to a white dental composition) in the past state were prepared by kneading components and degassing according to a formulating proportion shown in Table E-1. Monochromatic dental compositions prepared were used to perform a bending test and a depth of cure test according to the evaluation as described above. The results are shown in Table E-1.

Examples E-9~E-11 and Comparative Examples E-13~E-18

Preparation of a Vita Shade A3 Color Dental Composition

Vita Shade A3 color dental compositions (Examples E-9~E-11 and Comparative Examples E-13~E-18) in the pasty state were prepared by kneading components and degassing according to a formulating proportion shown in Table E-2 for various kneading times. Vita Shade A3 color dental compositions prepared were used to perform a color tone changing test according to the evaluation as described above. The results are shown in Table E-3.

Example E-12 and Comparative Examples E-19~E-20

Preparation of a Light Shielding Dental Composition

Light shielding dental compositions (Example E-12 and Comparative Examples E-19~E-20) in the pasty state were prepared by kneading components and degassing according to a formulating proportion shown in Table E4. Light shielding dental compositions prepared were used to perform a consistency test according to the evaluation as described above. The results are shown in Table E-4

TABLE E-1

|  | Example E-5 | Example E-6 | Example E-7 | Example E-8 | Comparative Example E-5 | Comparative Example E-6 | Comparative Example E-7 |
|---|---|---|---|---|---|---|---|
| Red filler | 300 | — | — | — | — | — | — |
| Yellow filler | — | 300 | — | — | — | — | — |
| Black filler | — | — | 300 | — | — | — | — |
| White filler | — | — | — | 300 | — | — | — |
| Diluted Red | — | — | — | — | 300 | — | — |
| Diluted Yellow | — | — | — | — | — | 300 | — |
| Diluted Black | — | — | — | — | — | — | 300 |
| Diluted White | — | — | — | — | — | — | — |
| Red pigment[1] | — | — | — | — | — | — | — |
| Yellow pigment[2] | — | — | — | — | — | — | — |
| Black pigment[3] | — | — | — | — | — | — | — |
| White pigment[4] | — | — | — | — | — | — | — |
| Glass filler[5] | — | — | — | — | — | — | — |
| Ultrafine particle silica[6] | 10 | 10 | 10 | 10 | 10 | 10 | 10 |
| Bis-GMA[7] | 60 | 60 | 60 | 60 | 60 | 60 | 60 |
| TEGDMA[8] | 40 | 40 | 40 | 40 | 40 | 40 | 40 |
| CQ[9] | 1 | 1 | 1 | 1 | 1 | 1 | 1 |
| DMABE[10] | 1 | 1 | 1 | 1 | 1 | 1 | 1 |
| Bending strength (MPa) | 115 | 98 | 121 | 123 | 98 | 75 | 101 |
| Depth of cure (mm) | 2.3 | 2.5 | 4.3 | 5.5 | 1.5 | 1.8 | 2.5 |

|  | Comparative Example E-8 | Comparative Example E-9 | Comparative Example E-10 | Comparative Example E-11 | Comparative Example E-12 |
|---|---|---|---|---|---|
| Red filler | — | — | — | — | — |
| Yellow filler | — | — | — | — | — |
| Black filler | — | — | — | — | — |
| White filler | — | — | — | — | — |
| Diluted Red | — | — | — | — | — |
| Diluted Yellow | — | — | — | — | — |
| Diluted Black | — | — | — | — | — |

TABLE E-1-continued

| | | | | | |
|---|---|---|---|---|---|
| Diluted White | 300 | — | — | — | — |
| Red pigment[1] | — | 7.7 | — | — | — |
| Yellow pigment[2] | — | — | 9.2 | — | — |
| Black pigment[3] | — | — | — | 6.2 | — |
| White pigment[4] | — | — | — | — | 12.1 |
| Glass filler[5] | — | 292.3 | 290.8 | 293.8 | 287.9 |
| Ultrafine particle silica[6] | 10 | 10 | 10 | 10 | 10 |
| Bis-GMA[7] | 60 | 60 | 60 | 60 | 60 |
| TEGDMA[8] | 40 | 40 | 40 | 40 | 40 |
| CQ[9] | 1 | 1 | 1 | 1 | 1 |
| DMABE[10] | 1 | 1 | 1 | 1 | 1 |
| Bending strength (MPa) | 105 | could not measured not cured | could not measured not cured | 95 | 93 |
| Depth of cure (mm) | 3.5 | 1.0 | 1.5 | 2.0 | 2.5 |

[1])Colcothar (12 weight parts silane-treated product)
[2])Yellow iron oxide (12 weight parts silane-treated product)
[3])Black iron oxide (12 weight parts silane-treated product)
[4])Titanium oxide (12 weight parts silane-treated product)
[5])Glass filler covered with poly(organo)siloxane without coloring particle in Example E-1 (12 weight parts silane-treated product)
[6])R-97
[7])2,2-bis(4-(3-methacryloyloxy-2-hydroxypropoxy)phenyl)propane
[8])Triethyleneglycol dimethacrylate
[9])dl-camphorquinone
[10])Ethyl p-N,N-dimethylaminobenzoate

TABLE E-2

| | Examples E-9~E-11 | Comparative Examples E-13~E-15 | Comparative Examples E-16~E-18 |
|---|---|---|---|
| Red filler | 15.1 | — | — |
| Yellow filler | 19.1 | — | — |
| Black filler | 2.5 | — | — |
| White filler | 7.8 | — | — |
| Diluted Red | — | 15.1 | — |
| Diluted Yellow | — | 19.1 | — |
| Diluted Black | — | 2.5 | — |
| Diluted White | — | 7.8 | — |
| Red pigment[1] | — | — | 0.4 |
| Yellow pigment[2] | — | — | 0.6 |
| Black pigment[3] | — | — | 0.1 |
| White pigment[4] | — | — | 0.3 |
| Glass filler[5] | 358.4 | 358.4 | 358.4 |
| Superfine particle silica[6] | 10 | 10 | 10 |
| Bis-GMA[7] | 60 | 60 | 60 |
| TEGDMA[8] | 40 | 40 | 40 |
| CQ[9] | 1 | 1 | 1 |
| DMABE[10] | 1 | 1 | 1 |
| Kneading time (hrs) | 0.5 (Example E-9) | 0.5 (Comparative Example E-13) | 0.5 (Comparative Example E-16) |
| | 2.0 (Example E-10) | 2.0 (Comparative Example E-14) | 2.0 (Comparative Example E-17) |
| | 4.0 (Example E-11) | 4.0 (Comparative Example E-15) | 4.0 (Comparative Example E-18) |

[1])Colcothar (12 weight parts silane-treated product)
[2])Yellow iron oxide (12 weight parts silane-treated product)
[3])Black iron oxide (12 weight parts silane-treated product)
[4])Titanium oxide (12 weight parts silane-treated product)
[5])Glass filler covered with poly(organo)siloxane without a coloring particle in Example E-1 (12 weight parts silane-treated product)
[6])R-972
[7])2,2-bis(4-(3-methacryloyloxy-2-hydroxypropoxy)phenyl)propane
[8])Triethyleneglycol dimethacrylate
[9])dl-camphorquinone
[10])Ethyl p-N,N-dimethylaminobenzoate

TABLE E-3

| | Kneading time (hrs) | Color difference (Δ E*ab) |
|---|---|---|
| Example E-9 | 0.5 | — |
| Example E-10 | 2.0 | 1.3 |
| Example E-11 | 4.0 | 1.4 |
| Comparative Example E-13 | 0.5 | — |
| Comparative Example E-14 | 2.0 | 4.5 |
| Comparative Example E-15 | 4.0 | 7.8 |
| Comparative Example E-16 | 0.5 | — |
| Comparative Example E-17 | 2.0 | 8.9 |
| Comparative Example E-18 | 4.0 | 12.5 |

TABLE E-4

| | Example E-12 | Comparative Example E-19 | Comparative Example E-20 |
|---|---|---|---|
| Red filler | 8 | — | — |
| Yellow filler | 50 | — | — |
| Black filler | 41 | — | — |
| White filler | 200 | — | — |
| Diluted Red | — | 8 | — |
| Diluted Yellow | — | 50 | — |
| Diluted Black | — | 41 | — |
| Diluted White | — | 200 | — |
| Red pigment[1] | — | — | 0.2 |
| Yellow pigment[2] | — | — | 1.5 |
| Black pigment[3] | — | — | 0.8 |
| White pigment[4] | — | — | 8 |
| Glass filler[5] | — | — | 288.5 |
| Superfine particle silica[6] | 10 | 10 | 10 |
| Bis-GMA[7] | 60 | 60 | 60 |
| TEGDMA[8] | 40 | 40 | 40 |
| 4-AET[9] | 10 | 10 | 10 |
| CQ[10] | 1 | 1 | 1 |

TABLE E-4-continued

|  |  | Example E-12 | Comparative Example E-19 | Comparative Example E-20 |
|---|---|---|---|---|
| DMABE[11] |  | 1 | 1 | 1 |
| Consistency | Immediately after preparation | 35.8 | 33.0 | 31.0 |
|  | After storage at 37 C. for one month | 35.0 | 28.5 | 25.5 |

[1] Colcothar (12 weight parts silane-treated product)
[2] Yellow iron oxide (12 weight parts silane-treated product)
[3] Black iron oxide (12 weight parts silane-treated product)
[4] Titanium oxide (12 weight parts silane-treated product)
[5] Glass filler covered with poly(organo)siloxane without a coloring particle in Example E-1 (12 weight parts silane-treated product)
[6] R-972
[7] 2,2-bis(4-(3-methacryloyloxy-2-hydroxypropoxy)phenyl)propane
[8] Triethyleneglycol dimethacrylate
[9] 4-acryloyloxyethylltrimelleric acid
[10] 4-dl-camphorquinone
[11] Ethyl p-N,N-dimethylaminobenzoate The coloring filler of the present invention has the excellent dispersibility and the color developing properties, and can impart the stable color tone in a dental composition. Furthermore, it can impart stable paste, mechanical property and optical properties.

What is claimed is:

1. An inorganic filler which comprises an inorganic fine particle having an average particle size of 0.01~5 µm, in which the surface of the inorganic fine particle is covered with polysiloxane, wherein the polysiloxane is a condensate obtained by hydrolysis or partial hydrolysis of a silane compound represented by the general formula (I):

(I)

wherein Z is RO— or OCN—, X is halogen, Y is —OH, R is an organic group having a carbon number of 8 or less, and n, m and L are an integer of 0 to 4, provided that n+m+L=4, wherein the inorganic fine particle is at least one selected from the group consisting of quartz, amorphous silica, aluminium silicate, aluminium oxide, titanium oxide, zirconium oxide, glasses, calcium carbonate, talc, kaolin, clay, mica, aluminium sulfate, calcium sulfate, barium sulfate, calcium phosphate, hydroxyapatite, silicon nitride, aluminium nitride, titanium nitride, silicon carbide, boron carbide, calcium hydroxide, strontium hydroxide and zeolite and wherein the glasses are selected from the group consisting of a glass prepared by a melting process, a synthetic glass prepared by a sol-gel process, and a glass produced by a vapor phase process.

2. The inorganic filler according to claim 1, wherein the polysiloxane is a condensate of a low-condensed silane compound and the low-condensed silane compound being prepared by partially hydrolyzing the silane compound represented by the general formula (I) and then low-condensing.

3. A process for producing the inorganic filler as defined in claim 1 or 2, which comprises:
   (1) a wet-grinding step of fine-grinding a raw material inorganic particle into an inorganic fine particle having an average particle size of 0.01 to 5 µm; and
   (2) a step of forming a polysiloxane film on the surface of the resulting inorganic fine particle.

4. A process for producing the inorganic filler as defined in claim 1 or 2, which comprises:
   (1) a wet-dispersing step of disintegrating an aggregate of inorganic fine particles into primary particles, the primary particle having an average particle size of 0.01~5 µm; and
   (2) a step of forming a polysiloxane film on the surface of the resulting inorganic fine particle which is a primary particle.

5. A process for producing the inorganic filler as defined in claim 1 or 2, which comprises:
   (1) a wet-grinding step of fine-grinding a raw material inorganic particle into an inorganic fine particle having an average particle size of 0.01 to 5 µm. and
   (2) a step of forming a polysiloxane film on the surface of the resulting inorganic fine particle, wherein the step of forming a polysiloxane film comprises:
      (2-1) a step of at least partially hydrolyzing a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, in the presence of the inorganic fine particle which is dispersed in an aqueous medium, and then condensing the resulting silanol compound;
      (2-2) a step of drying the resulting aqueous dispersion; and
      (2-3) a step of disintegrating the dried material into primary particles.

6. The process according to claim 3, wherein the wet-grinding step is performed in an aqueous medium containing water as a main component.

7. The process according to claim 4, wherein the wet-dispersing step is performed in an aqueous medium containing water as a main component.

8. A dental composition which comprises the inorganic filler as defined in claim 1 or 2 in the state where the surface of the inorganic filler has been treated with an organosilane compound represented by the general formula (II):

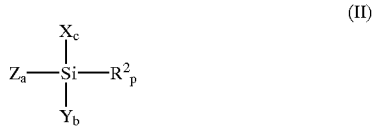
(II)

wherein Z is $R^1O$— or OCN—, X is halogen, Y is —OH, $R^1$ is an organic group having a carbon number of 8 or less, $R^2$ is an organic group, p is an integer of 1 to 3, and a, b and c are each independently an integer of 0 to 3, provided that a+b+c+p=4.

9. The dental composition according to claim 8, wherein the inorganic filler is dispersed and contained in the non-aggregated state.

10. The dental composition according to claim 8, which further comprises a polymerizable monomer and a polymerization initiator.

11. A multi-functional filler which comprises an inorganic fine particle containing an acid reactive element and a fluoride, wherein a cement reactive phase is formed on the surface of the inorganic fine particle, and the cement reactive phase is further covered with polysiloxane.

12. The multi-functional filler according to claim 11, wherein the inorganic fine particle is a fluoride-containing glass.

13. The multi-functional filler according to claim 12, wherein the inorganic fine particle is selected from the group consisting of sodium fluoride, strontium fluoride, lanthanum fluoride, ytterbium fluoride, yttrium fluoride, a calcium-containing fluoroaluminosilicate glass, a lanthanum-containing fluoroaluminosilicate glass, and a strontium-containing fluoroaluminosilicate glass.

14. The multi-functional filler according to claim 11, wherein the acid reactive element is selected from the group consisting of elements belonging to Groups I, II and III in the Periodic Table.

15. A process for producing the multi-functional filler as defined in any of claims 12 to 14, which comprises: reacting an acidic polymer with an acid reactive element-containing inorganic fine particle covered with polysiloxane.

16. The process according to claim 15, wherein the acid reactive element-containing inorganic fine particle covered with polysiloxane is obtained by at least partially hydrolyzing, in an aqueous medium containing the acid reactive element-containing inorganic fine particle, a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, and then condensing the resulting silanol compound.

17. The process according to claim 15, wherein the acid reactive element-containing inorganic particle covered with polysiloxane is obtained by condensing a low-condensed silane compound obtained by partially hydrolyzing, in an aqueous dispersion containing the acid reactive element-containing inorganic fine particle, a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, followed by partially condensing.

18. The process according to claim 15, wherein a reaction of the acid reactive element-containing inorganic fine particle covered with polysiloxane, with an acidic polymer is carried out by impregnating the inorganic fine particle with a solution of the acidic polymer.

19. A dental composition which comprises the multi-functional filler as defined in any one of claims 11 to 14, in the state where the surface of the multi-functional filler is treated with an organosilane compound represented by the general formula (II):

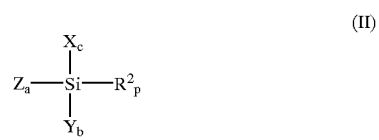
(II)

wherein Z is $R^1O$— or OCN—, X is halogen, Y is —OH, $R^1$ is an organic group having a carbon number of 8 or less, $R^2$ is an organic group, p is an integer of 1 to 3, and a, b and c are each independently an integer of 0 to 3, provided that a+b+c+p=4.

20. The dental composition according to claim 19, wherein the multi-functional filler is dispersed and contained in the non-aggregated state.

21. The dental composition according to claim 19, which further comprises a polymerizable monomer, and a polymerization initiator.

22. An organic compound filler, which comprises an organic-inorganic polymer particle or an organic polymer particle, wherein the surface of the organic-inorganic polymer particle or the organic polymer particle is covered with a poly(organo)siloxane film, wherein the poly(organo)siloxane film is (1) a condensate obtained at least partially hydrolyzing a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound:

(2) a co-condensate obtained by at least partially hydrolyzing the silane compound represented by the general formula (I) and/or the low-condensate of the silane compound in the presence of an organosilane compound represented by the general formula (II):

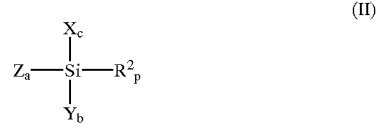
(II)

wherein Z is $R^1O$— or OCN—, X is halogen, Y is —OH, $R^1$ is an organic group having a carbon number of 8 or less, $R^2$ is an organic group, a, b and c are each independently an integer of 0 to 3, and, is an integer of 1 to 3, provided that a+b+c+p=4, and/or a low-condensate of the organosilane compound, (3) a co-condensate obtained by at least partially hydrolyzing the silane compound represented by the general formula (I) and/or the low-condensate of the silane compound in the presence of a metal compound, or (4) a co-condensate obtained by at least partially hydrolyzing the silane compound represented by the general formula (I) and/or the low-condensate of the silane compound in the presence of the orpanosilane compound represented by the general formula (II) and/or the low-condensate of the organosilane compound and a metal compound, wherein the poly(organo)siloxane film is at least one selected from the group consisting of (2) a co-condensate obtained by at least partially hydrolyzing the silane compound represented by the general formula (I), the low-condensate of the silane compound in the presence of the organosilane compound represented by the general formula (II), and the low-condensate of the organosilane compound.

23. An organic compound filler, which comprises an organic-inorganic polymer particle or an organic polymer particle, wherein the surface of the organic-inorganic polymer particle or the organic polymer particle is covered with a poly(orpano)siloxane film, wherein the poly(orpano)siloxane film is (1) a condensate obtained at least partially hydrolyzing a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound, (2) a co-condensate obtained by at least partially hydrolyzing the silane compound represented by the general formula (I) and/or the low-condensate of the silane compound in the presence of an organosilane compound represented by the general formula (II):

(II)

wherein Z is $R^1O$— or OCN—, X is halogen, Y is —OH, $R^1$ is an organic group having a carbon number of 8 or less, $R^2$ is an organic group, a, b and c are each independently an integer of 0 to 3, and p is an integer of 1 to 3, provided that a+b+c+p=4, and/or a low-condensate of the organosilane compound, (3) a co-condensate obtained by at least partially hydrolyzing the silane compound represented by the general formula (I) and/or the low-condensate of the silane compound in the presence of a metal compound: or (4) a co-condensate obtained by at least partially hydrolyzing the silane compound represented by the general formula (I) and/or the low-condensate of the silane compound in the presence of the organosilane compound represented by the general formula (II) and/or the low-condensate of the organosilane compound and a metal compound, wherein the poly(organo)siloxane film is (3) a co-condensate obtained by at least partially hydrolyzing the silane compound represented by the general formula (I) and/or the low-condensate of the silane compound in the presence of a metal compound.

24. An oroanic compound filler, which comprises an organic-inorganic polymer particle or an organic polymer particle, wherein the surface of the organic-inorganic polymer particle or the organic polymer particle is covered with a poly(organo)siloxane film, wherein the poly(organo)siloxane film is (1) a condensate obtained at least partially hydrolyzing a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound;

(2) a co-condensate obtained by at least partially hydrolyzing the silane compound represented by the general formula (I) and/or the low-condensate of the silane compound in the presence of an organosilane compound represented by the general formula (II):

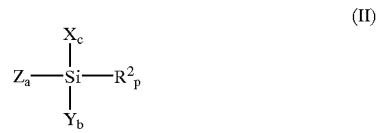

(II)

wherein Z is $R^1O$— or OCN—, X is halogen, Y is —OH, $R^1$ is an organic group having a carbon number of 8 or less, $R^2$ is an organic group, a, b and c are each independently an integer of 0 to 3, and p is an integer of 1 to 3, provided that a+b+c+p=4, and/or a low-condensate of the organosilane compound;

(3) a co-condensate obtained by at least partially hydrolyzing the silane compound represented by the general formula (I) and/or the low-condensate of the silane compound in the presence of a metal compound; or (4) a co-condensate obtained by at least partially hydrolyzing the silane compound represented by the general formula (I) and/or the low-condensate of the silane compound in the presence of the organosilane compound represented by the general formula (II) and/or the low-condensate of the organosilane compound and a metal compound, wherein the poly(organo)siloxane film is (4) a co-condensate obtained by at least partially hydrolyzing the silane compound represented by the general formula (I) and/or the low-condensate of the silane compound in the presence of the organosilane compound represented by the general formula (II) and/or the low-condensate of the organosilane compound and a metal compound.

25. A process for producing an organic compound filler, which comprises an organic-inorganic polymer particle or an organic polymer particle, wherein the surface of the organic-inorganic polymer particle or the organic polymer particle is covered with a poly(organo)siloxane film, wherein the poly(organo)siloxane film is (1) a condensate obtained at least partially hydrolyzing a silane compound represented by the general fonnula (I):

(I)

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound;

(2) a co-condensate obtained by at least partially hydrolyzin the silane compound represented by the general formula (I) and/or the low-condensate of the silane compound in the presence of an organosilane compound represented by the general formula (II):

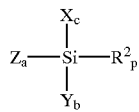

wherein Z is R¹O— or OCN—, X is halogen, Y is —OH, R¹ is an organic group having a carbon number of 8 or less, R² is an organic group, a, b and c are each independently an integer of 0 to 3, and p is an integer of 1 to 3, provided that a+b+c+p=4, and/or a low-condensate of the organosilane compound;

(3) a co-condensate obtained by at least partially hydrolyzing the silane compound represented by the general formula (I) and/or the low-condensate of the silane compound in the presence of a metal compound; or (4) a co-condensate obtained by at least partially hydrolyzing the silane compound represented by the general formula (I) and/or the low-condensate of the silane compound in the presence of the organosilane compound represented by the general formula (II) and/or the low-condensate of the organosilane compound and a metal compound, which comprises: (1) a step of preparing a dispersion by dispersing an organic-inorganic polymer particle or an organic polymer particle in an aqueous medium, (2) a step of forming a poly(organo)siloxane film on the surface of the particle in the resulting dispersion, (3) a step of heat-treating the particle having the poly(organo)siloxane film formed thereon to form a heat-treated granule after separating the particle or without separating the particle, and (4) a step of disintegrating the heat-treated granule to a primary particle.

26. The process according to claim 25, wherein the step of forming a poly(organo)siloxane film comnprises: at least partially hydrolyzing a silane compound represented by the general formula (I):

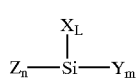

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound in the presence of an organic-inorganic polymer particle or an organic polymer particle dispersed in an aqueous medium, followed by condensing.

27. The process according to claim 25, wherein the step of forming the poly(organo)siloxane film comprises: at least partially hydrolyzing the silane compound represented by the general formula (I) and/or the low-condensate of the silane compound in the presence of an organosilane compound represented by the general formula (II):

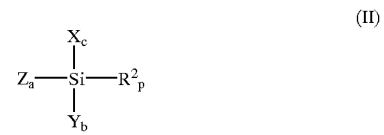

wherein Z is R¹O— or OCN—, X is halogen, Y is —OH, R¹ is an organic group having a carbon number of 8 or less, R² is an organic group, a, b and c are each independently an integer of 0 to 3, and p is an integer of 1 to 3, provided that a+b+c+p=4, and/or a low-condensate of the organosilane compound, followed by co-condensing.

28. The process according to claim 25, wherein the step of forming the poly(organo)siloxane film comprises: at least partially hydrolyzing the silane compound represented by the general formula (I) and/or the low-condensate of the silane compound in the presence of a metal compound, followed by co-condensing.

29. The process according to claim 25, wherein the step of forming the poly(organo)siloxane film comprises: at least partially hydrolyzing the silane compound represented by the general formula (I) and/or the low-condensate of the silane compound in the presence of the organosilane compound represented by the general formula (II) and/or the low-condensate of the organosilane compound and a metal compound, followed by co-condensing.

30. A dental composition, which comprises (a) the organic compound fillers as defined in any one of claims 22 to 24, (b) a polymerizable monomer, and (c) a polymerization initiator.

31. A modified filler which comprises an inorganic fine particle having an average particle size of 0.01~5 μm, wherein the surface of said inorganic fine particle is covered with polyorganosiloxane and the polyorganosiloxane is at least one selected from the group consisting of:

(1) a co-condensate obtained by hydrolysis or partial hydrolysis of a silane compound represented by the general formula (I):

wherein Z is RO— or OCN—, X is halogen, Y is —OH, R is an organic group having a carbon number of 8 or less, and n, m and L are an integer of 0 to 4, provided that n+m+L=4, and/or a low condensate of the silane compound, and an organosilane compound represented by the general formula (II):

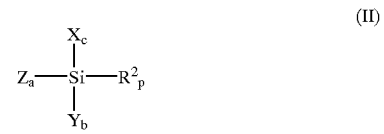

wherein Z is R¹O— or OCN—, X is halogen, Y is —OH, R¹ is an organic group having a carbon number of 8 or less, R² is an organic group, p is an integer of 1 to 3, and a, b and c are each independently an integer of 0 to 3, provided that a+b+c+p=4, and/or a low condensate of the organosilane compound, and (2) a co-condensate obtained by at least partial hydrolysis of a silane compound represented by the general formula (I) and/or a low-condensate of the silane compound and an organosilane compound represented by the general formula (II) and/or a low condensate of the organosilane compound in the presence of a metal compound.

32. The modified filler according to claim 31, wherein the polyorganosiloxane is a co-condensate obtained by at least partial hydrolysis of a silane compound represented by the general formula (I) and/or a low-condensate of the silane compound and an organosilane compound represented by the general formula (II) or a low condensate of the organosilane compound.

33. The modified filler according to claim 31 or 32, wherein the polyorganosiloxane is a co-condensate obtained by at least partial hydrolysis of a silane compound represented by the general formula (I) and/or a low condensate of the silane compound and an organosilane compound represented by the general formula (II) or a low condensate of the organosilane compound in the presence of a metal compound.

34. A process for producing the modified filler as defined in claim 31, which comprises:
  (1) a wet-grinding step of finely-grinding a raw material inorganic particle into an inorganic fine particle having an average particle size of 0.01~5 μm, or a wet-dispersing step of disintegrating an inorganic fine particle aggregate into a primary particle, said primary particle having an average particle size of 0.01~5 μm, and (2) a step of covering the inorganic fine particle with a polyorganosiloxane film on the surface of the resulting inorganic fine particle.

35. A process for producing the modified filler as defined in according to claim 31, which comprises:
  (1) a wet-grinding step of finely-grinding a raw material inorganic particle into an inorangic fine particle having an average particle size of 0.01~5 μm, or a wet-dispersing step of disintegrating an inorganic fine particle aggregate into primary particles, said primary particles having an average size of 0.01~5 μm, and
  (2) a step of forming a polyorganosiloxane film on the surface of the resulting inorganic fine particle, wherein the step of forming a polyorganosiloxane film comprises:
    (2-1) a step of at least partially hydrolysing a silane compound represented by the general formula (I):

wherein Z is RO— or OCN—, X is halogen, Y is —OH, R is an organic group having a carbon number of 8 or less, and n, m and L are each independently an integer of 0 to 4, provided that n+m+L=4, and/or a low condensate of the silane compound, and an organosilane compound represented by the general formula (II):

wherein Z is $R^1O$— or OCN—, X is halogen, Y is —OH, $R^1$ is an organic group having a carbon number of 8 or less, $R^2$ is an organic group, p is an integer of 1 to 3, and a, b and c are each independently an integer of 0 to 3, provided that a+b+c+p=4, and/or a low condensate of the organosilane compound in the presence of the inorganic fine particle dispersed in an aqueous medium and, then, co-condensing the resulting silanol compounds, (2-2) a step of heat-treating the resulting aqueous dispersion, and (2-3) a step of disintegrating the heat-treated solidified material into primary particles.

36. The process according to claim 34, wherein the step of covering the inorganic fine particle with the polyorganosiloxane film comprises (2-1)' a step of at least partially hydrolysing a silane compound represented by the general formula (I) and/or a low-condensate of the silane compound and an organosilane compound represented by the general formula (II) and/or a low-condensate of the organosilane compound in the presence of a metal compound and, then, co-condensing the resulting silanol compound, (2-2)' a step of heat-treating the resulting aqueous dispersion, and (2-3)' a step of disintegrating the heat-treated solidified material into primary particles.

37. A dental composition, which comprises (a) the modified fillers as defined in any one of claims 31 to 32, (b) a polymerizable monomer, and (c) a polymerization initiator.

38. The dental composition according to claim 37, wherein the modified filler is dispersed and contained in the non-aggregated state.

39. A dental coloring filler, which comprises an inorganic particle and a coloring particle, wherein the inorganic particle and the coloring particle are uniformly mixed and dispersed, the surfaces of these particles are covered with poly(organo)siloxane, and the poly(organo)siloxane is
  (1) a condensate obtained by at least partially hydrolyzing a silane compound represented by the general formula (I):

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound;
  (2) a co-condensate obtained by at least partially hydrolyzing the silane compound represented by the general formula (I) and/or the low-condensate of the silane compound in the presence of an organosilane compound represented by the general formula (II):

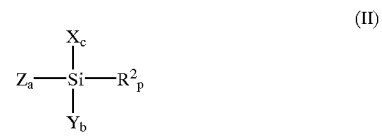

wherein Z is $R^1O$— or OCN—, X is halogen, Y is —OH, $R^1$ is an organic group having a carbon number of 8 or less, $R^2$ is an organic group, p is an integer of 1 to 3, and a, b and c are each independently an integer of 0 to 3, provided that a+b+c+p=4, and/or a low-condensate of the organosilane compound;

(3) a co-condensate obtained by at least partially hydrolyzing the silane compound represented by the general formula (I) and/or the low-condensate of the silane compound in the presence of a metal compound; or (4) a co-condensate obtained by at least partially hydrolyzing the silane compound represented by the general formula (I) and/or the low-condensate of the silane compound in the presence of the organosilane compound represented by the general formula (II) and/or the low-condensate of the organosilane compound and a metal compound.

40. The dental coloring filler according to claim 39, wherein the poly(organo)siloxane is (1) a condensate obtained by at least partially hydrolyzing the silane compound represented by the general formula (I) and/or the low-condensate of the silane compound.

41. The dental coloring filler according to claim 39, wherein the poly(organo)siloxane is (2) a co-condensate obtained by at least partially hydrolyzing the silane compound represented by the general formula (I) and/or the low-condensate of the silane compound in the presence of the organosilane compound represented by the general formula (II) or the low-condensate of the organosilane compound.

42. The dental coloring filler according to claim 39, wherein the poly(organo)siloxane is (3) a co-condensate obtained by at least partially hydrolyzing the silane compound represented by the general formula (I) and/or the low-condensate of the silane compound in the presence of a metal compound.

43. The dental coloring filler according to claim 39, wherein the poly(organo)siloxane is (4) a co-condensate obtained by at least partially hydrolyzing the silane compound represented by the general formula (I) and/or the low-condensate of the silane compound in the presence of the organosilane compound represented by the general formula (II) and/or the low-condensate of the organosilane compound and a metal compound.

44. A process for producing the dental coloring filler as defined in claim 39, which comprises: (1) a step of preparing a mixed particle by uniformly mixing and dispersing an inorganic particle and a coloring particle, and (2) a step of forming a poly(organo)siloxane film on the surface of the resulting mixed particle.

45. The process according to claim 44, wherein the step of forming the poly(organo)siloxane film comprises: (2-1) in the presence of a mixed particle which is uniformly mixed and dispersed, at least partially hydrolyzing a silane compound represented by the general formula (I):

(I)

wherein Z is RO— or OCN—, X is halogen, Y is —OH, R is an organic group having a carbon number of 8 or less, and n, m and L are each independently an integer of 0 to 4, provided that n+m+L=4, and/or a low-condensate of the silane compound, followed by condensing.

46. The process according to claim 44, wherein the step of forming the poly(organo)siloxane film comprises: (2-1) in the presence of a mixed particle which is uniformly mixed and dispersed, at least partially hydrolyzing the silane compound represented by the general formula (I) and/or the low-condensate of the silane compound in the presence of an organosilane compound represented by the general formula (II):

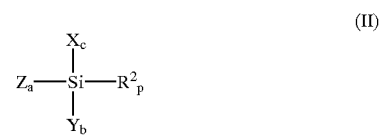

(II)

wherein Z is $R^1O$— or OCN—, X is halogen, Y is —OH, $R^1$ is an organic group having a carbon number of 8 or less, $R^2$ is an organic group, p is an integer of 1 to 3, and a, b and c are each independently an integer of 0 to 3, provided that a+b+c+p=4, and/or a low-condensate of the organosilane compound, followed by co-condensing.

47. The process according to claim 44, wherein the step of forming the poly(organo)siloxane film comprises: (2-1) in the presence of a mixed particle which is uniformly mixed and dispersed, at least partially hydrolyzing the silane compound represented by the general formula (I) and/or the low-condensate of the silane compound in the presence of a metal compound, followed by co-condensing.

48. The process according to claim 44, wherein the step of forming the poly(organo)siloxane film comprises: (2-1) in the presence of a mixed particle which is uniformly mixed and dispersed, at least partially hydrolyzing the silane compound represented by the general formula (I) and/or the low-condensate of the silane compound in the presence of the organosilane compound represented by the general formula (II) and/or the low-condensate of the organosilane compound and a metal compound, followed by co-condensing.

49. A dental composition, which comprises (a) the dental coloring filler as defined in any one of claims 39 to 45, (b) a polymerizable monomer, and (c) a polymerization initiator.

50. The denal composition according to claim 49, which further comprises (d) a filler.

* * * * *